US008105634B2

(12) United States Patent
Liu et al.

(10) Patent No.: US 8,105,634 B2
(45) Date of Patent: Jan. 31, 2012

(54) UMBILICAL CORD BIOMATERIAL FOR MEDICAL USE

(75) Inventors: Qing Liu, Hillsborough, NJ (US); Henry Rendon Barragan, Little Ferry, NJ (US); George Matcham, Cranbury, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 1178 days.

(21) Appl. No.: 11/893,409

(22) Filed: Aug. 15, 2007

(65) Prior Publication Data

US 2008/0069895 A1    Mar. 20, 2008

Related U.S. Application Data

(60) Provisional application No. 60/838,132, filed on Aug. 15, 2006.

(51) Int. Cl.
*A61K 35/50*    (2006.01)

(52) U.S. Cl. .................. 424/583; 424/93.7

(58) Field of Classification Search .............. None
See application file for complete search history.

(56) References Cited

U.S. PATENT DOCUMENTS

| | | | |
|---|---|---|---|
| 3,157,524 A | 11/1964 | Artandi | |
| 3,800,792 A | 4/1974 | McKnight et al. | |
| 4,060,081 A | 11/1977 | Yannas et al. | |
| 4,240,794 A * | 12/1980 | Holman et al. | 8/94.11 |
| 4,320,201 A | 3/1982 | Berg et al. | |
| 4,361,552 A | 11/1982 | Baur, Jr. | |
| 4,420,339 A | 12/1983 | Kato | |
| 4,599,226 A | 7/1986 | Fox, Jr. et al. | |
| 4,704,131 A | 11/1987 | Noishiki et al. | |
| 4,772,284 A | 9/1988 | Jefferies et al. | |
| 4,801,299 A | 1/1989 | Brendel et al. | |
| 4,837,285 A | 6/1989 | Berg et al. | |
| 4,973,493 A | 11/1990 | Guire | |
| 5,028,695 A | 7/1991 | Eckmayer et al. | |
| 5,036,056 A | 7/1991 | Kludas | |
| 5,116,620 A | 5/1992 | Chvapil et al. | |
| 5,141,747 A | 8/1992 | Scholz | |
| 5,230,693 A | 7/1993 | Williams et al. | |
| 5,308,889 A | 5/1994 | Rhee et al. | |
| 5,428,022 A | 6/1995 | Palefsky et al. | |
| 5,436,135 A | 7/1995 | Tayot | |
| 5,486,359 A | 1/1996 | Caplan | |
| 5,523,291 A | 6/1996 | Janzen et al. | |
| 5,607,590 A | 3/1997 | Shimizu | |
| 5,612,028 A | 3/1997 | Sackier et al. | |
| 5,618,312 A | 4/1997 | Yui et al. | |
| 5,635,517 A | 6/1997 | Muller | |
| 5,639,796 A | 6/1997 | Lee | |
| 5,656,478 A | 8/1997 | Tanagho et al. | |
| 5,658,582 A | 8/1997 | Dorigatti et al. | |
| 5,686,425 A | 11/1997 | Lee | |
| 5,698,579 A | 12/1997 | Muller | |
| 5,705,488 A | 1/1998 | Janzen et al. | |
| 5,720,777 A | 2/1998 | Jaffe et al. | |
| 5,723,010 A | 3/1998 | Yui et al. | |
| 5,739,113 A | 4/1998 | Lee | |
| 5,763,399 A | 6/1998 | Lee | |
| 5,798,368 A | 8/1998 | Muller | |
| 5,814,328 A | 9/1998 | Gunasekaran | |
| 5,830,548 A | 11/1998 | Andersen et al. | |
| 5,837,278 A | 11/1998 | Geistlich et al. | |
| 5,874,448 A | 2/1999 | Muller | |
| 5,876,451 A | 3/1999 | Yui et al. | |
| 5,877,200 A | 3/1999 | Muller | |
| 5,916,266 A | 6/1999 | Yui et al. | |
| 5,929,117 A | 7/1999 | Muller | |
| 5,932,205 A | 8/1999 | Wang et al. | |
| 5,939,323 A | 8/1999 | Valentini et al. | |
| 5,955,476 A | 9/1999 | Muller | |
| 5,993,844 A | 11/1999 | Abraham et al. | |
| 6,093,417 A | 7/2000 | Petrus | |
| 6,113,932 A | 9/2000 | Hoath et al. | |
| 6,124,259 A | 9/2000 | Delmage et al. | |
| 6,143,315 A | 11/2000 | Wang et al. | |
| 6,152,142 A | 11/2000 | Tseng | |
| 6,261,549 B1 | 7/2001 | Fernandez | |
| 6,281,230 B1 | 8/2001 | Muller | |
| 6,300,315 B1 | 10/2001 | Liu | |
| 6,316,471 B1 | 11/2001 | Muller | |
| 6,326,019 B1 | 12/2001 | Tseng | |
| 6,335,349 B1 | 1/2002 | Muller | |
| 6,371,992 B1 | 4/2002 | Tanagho et al. | |

(Continued)

FOREIGN PATENT DOCUMENTS

DE    2631909    7/1976

(Continued)

OTHER PUBLICATIONS

International Search Report and Written Opinion for PCT/US2007/018059, dated Dec. 20, 2007.
U.S. Appl. No. 11/811,447, filed Jun. 8, 2007, Heidaran.
U.S. Appl. No. 11/893,409, filed Aug. 15, 2007, Liu et al.
Akle et al., 1981, "Immunogenicity of Human Amniotic Epithelial Cells After Transplantation Into Volunteers," The Lancet, 2: 1003-1005.
Allman, 2001, "Xenogenic Extracellular Matrix Grafts Elicit a TH2-Restriced Immune Response," Transplantation, 71(11):1631-1640.
Anderson et al. , 2001, "Amniotic Membrane Transplantation After the Primary Surgical Management of Band Keratopathy," Cornea, 20(4):354-361.

(Continued)

Primary Examiner — Allison Ford
(74) Attorney, Agent, or Firm — Jones Day

(57) ABSTRACT

The present invention provides a biomaterial comprising a mammalian umbilical cord membrane. The biomaterial can additionally comprise Wharton's jelly and/or one or more umbilical cord vessels. The biomaterial is preferably dry, and can be flat, tubular, or shaped to fit a particular body structure. The invention further provides laminates comprising at least one layer of an umbilical cord membrane biomaterial. The invention further provides methods of making the biomaterial, and laminates comprising the biomaterial, and methods of using the biomaterial.

18 Claims, 5 Drawing Sheets

U.S. PATENT DOCUMENTS

| | | | |
|---|---|---|---|
| 6,379,323 B1 | 4/2002 | Patterson | |
| 6,380,239 B1 | 4/2002 | Muller | |
| 6,387,367 B1 | 5/2002 | Davis-Sproul | |
| 6,395,754 B1 | 5/2002 | Muller | |
| 6,403,613 B1 | 6/2002 | Man | |
| 6,417,166 B2 | 7/2002 | Liu | |
| 6,428,802 B1 | 8/2002 | Atala | |
| 6,432,710 B1 | 8/2002 | Boss et al. | |
| 6,432,712 B1 | 8/2002 | Wolfinbarger, Jr. | |
| 6,458,810 B1 | 10/2002 | Muller | |
| 6,476,052 B1 | 11/2002 | Muller | |
| 6,479,064 B1 | 11/2002 | Atala | |
| 6,555,554 B2 | 4/2003 | Muller | |
| 6,652,594 B2 | 11/2003 | Francis et al. | |
| 6,734,018 B2 | 5/2004 | Wolfinbarger et al. | |
| 6,753,181 B2 | 6/2004 | Atala | |
| 6,866,686 B2 | 3/2005 | Ollerenshaw et al. | |
| 6,962,814 B2 | 11/2005 | Mitchell et al. | |
| 7,045,148 B2 | 5/2006 | Hariri | |
| 7,091,353 B2 | 8/2006 | Robarge | |
| 2001/0037014 A1 | 11/2001 | Liu | |
| 2001/0038848 A1 | 11/2001 | Donda et al. | |
| 2002/0103542 A1 | 8/2002 | Bilbo | |
| 2002/0151974 A1 | 10/2002 | Bonassar et al. | |
| 2002/0197296 A1 | 12/2002 | Gen | |
| 2003/0032179 A1 | 2/2003 | Hariri | |
| 2003/0045552 A1 | 3/2003 | Robarge | |
| 2003/0143207 A1 | 7/2003 | Livesey et al. | |
| 2003/0161818 A1* | 8/2003 | Weiss et al. | 424/93.21 |
| 2003/0180269 A1 | 9/2003 | Hariri | |
| 2003/0187515 A1 | 10/2003 | Hariri et al. | |
| 2003/0235909 A1 | 12/2003 | Hariri | |
| 2004/0028660 A1 | 2/2004 | Hariri | |
| 2004/0048796 A1 | 3/2004 | Hariri | |
| 2005/0096351 A1 | 5/2005 | Jaworsky | |
| 2005/0203636 A1* | 9/2005 | McFetridge | 623/23.72 |
| 2006/0084815 A1 | 4/2006 | Muller | |
| 2007/0020225 A1 | 1/2007 | Abramson et al. | |
| 2007/0021704 A1 | 1/2007 | Hariri et al. | |
| 2007/0021762 A1 | 1/2007 | Liu et al. | |
| 2007/0202189 A1 | 8/2007 | Ahlfors | |
| 2008/0044848 A1* | 2/2008 | Heidaran | 435/29 |

FOREIGN PATENT DOCUMENTS

| | | | |
|---|---|---|---|
| EP | 214853 A2 | 3/1987 | |
| EP | 0 399 782 A2 | 11/1990 | |
| EP | 0399782 A2 | 11/1990 | |
| EP | 526756 A1 | 2/1993 | |
| EP | 637452 A1 | 2/1995 | |
| EP | 734736 A1 | 10/1996 | |
| EP | 773033 A1 | 5/1997 | |
| EP | 0 781 564 A2 | 7/1997 | |
| EP | 781564 A2 | 7/1997 | |
| EP | 1031356 A2 | 8/2000 | |
| EP | 1103277 A1 | 5/2001 | |
| FR | 2 563 727 A1 | 11/1985 | |
| FR | 2613620 A1 | 10/1988 | |
| GB | 2360789 A | 10/2001 | |
| JP | 62-268875 | 11/1987 | |
| JP | 5056987 | 3/1993 | |
| NL | 9101149 | 2/1993 | |
| SU | 1286211 | 1/1987 | |
| WO | WO 88/08305 A1 | 11/1988 | |
| WO | WO 95/07095 A1 | 3/1995 | |
| WO | WO 95/22301 A1 | 8/1995 | |
| WO | WO 96/13974 A1 | 5/1996 | |
| WO | WO 97/48405 A1 | 12/1997 | |
| WO | WO 98/03502 A1 | 1/1998 | |
| WO | WO 98/37903 | 9/1998 | |
| WO | WO 98/37903 A1 | 9/1998 | |
| WO | WO 98/54170 A1 | 12/1998 | |
| WO | WO 99/63051 A1 | 12/1999 | |
| WO | WO 99/65427 A1 | 12/1999 | |
| WO | WO 01/15750 A1 | 3/2001 | |
| WO | WO 01/66162 A1 | 9/2001 | |
| WO | WO 02/09647 A2 | 2/2002 | |
| WO | WO 02/059106 A1 | 8/2002 | |
| WO | WO 03/020297 A2 | 3/2003 | |
| WO | WO 03/087333 A2 | 10/2003 | |

OTHER PUBLICATIONS

Anderson et al., 2001, "Amniotic Membrane Transplantation for Partial Limbal Stem Cell Deficiency," British J. of Opthamology, 85:567-575.

Aplin et al., 1985, "The Extracellular Matrix of Human Amniotic Epithelium: Ultrastructure, Composition and Deposition," J. Cell Sci., 79:119-136.

Arora et al., 1994, "Controlled Comparison of Interceed and Amniotic Membrane Graft in the Prevention of Postoperative Adhesions in the Rabbit Uterine Horn Model," European Journal of Obstetrics Gynecology and Reproductive Biology, 55: 179-182.

Ashworth et al., 1986, "Vaginoplasty Using Amnion," Obstet. Gynecol., 67:443-446.

Atanassov et al., 1994, "Use of Amniotic Membranes As Biological Dressings in Contemporary Treatment of Burns," Ann. Medit. Burns Club, 7(4).

Atiyeh et al., 2002, "Management of Acute and Chronic Open Wounds: The Importance of Moist Environment in Optimal Wound Healing," Cuff. Pharm. Biotechnol., 3:179-195.

Bachinger et al., 1990, "The Relationship of the Biophysical and Biochemical Characteristics of Type VII Collagen to the Function of Anchoring Fibrils," J. Biol. Chem., 265: 0095-10101.

Badawy et al., 1989, "Evaluation of Tissue Healing and Adhesion Formation After an Intraabdominal Amniotic Membrane Graft in the Rat," J. Reprod. Med., 34(3):198-202.

Badylak, 1999, "Endothelial Cell Adherence to Small Intestinal Submucosa: An Acellular Bioscaffold," Biomaterials, 20:2257-2263.

Badylak, 2002, "The Extracellular Matrix As a Scaffold for Tissue Reconstruction," Semin. Cell Dev. Biol., 13:377-383.

Bapat et al., 1974, "Preliminary Report on Acceleration of Wound Healing by Amnion Membrane Graft," Indian J. Med. Res., 62:1342-1346.

Bari et al., 2002, "Role of Human Foetal Membranes (Amniotic Membrane) in the Management of Burn Wounds," Annals of Burns and Fire disasters, XV(4):1-8.

Barlas et al., 1992, "Human Amniotic Membrane As an Intestinal Patch for Neomucosal Growth in the Rabbit Model," J. Pediatr. Surg., 27(5):597-601.

Barton et al., 1997, "Amniotic Membrane Translplantation in Glaucoma Surgery," Investig. Opthalmology and Visual Science, Abstract Book, Part I: Annual Meeting, Ft. Lauderdale, Florida, May 11-16, 1997, 38(4):5473, Abstract 2194.

Bennett et al., 1980, "Treatment of Chronic Ulceration of the Legs With Human Amnion," Lancet, 1: 1153-1155.

Benque et al., 1997, "Combined Collagen Membrane and Hydroxyapatite/Collagen Chondroitin-Sulfate Spacer Placement in the Treatment of 2-Wall Intrabony Defects in Chronic Adult and Rapidly Progressive Periodontitis Patients," J. Clin. Periodontol., 24(8):550-556.

Black et al., 1994, "Comparative Study of Collagen and Expanded Polytetrafluoroethylene Membranes in the Treatment of Human Class II Furcation Defects," J. Periodontol., 65(6):598-604.

Bleggi-Torres et al., 1997, "Ultrastructural Study of the Neovagina Following the Utilization of Human Amniotic Membrane for Treatment of Congenital Absence of the Vagina," Brazilian Journal of Medical and Biological Research, 30: 861-864.

Blumenthal, 1993, "A Clinical Comparison of Collagen Membranes With E-PTFE Membranes in the Treatment of Human Mandibular Buccal Class II Furcation Defects," J. Periodontol., 64(10):925-933.

Boc et al., 1985, "Implications for the Use of Amnion and Chorion in Podiatric Medicine and Surgery," J. Foot Surg., 24(4):236-242.

Bose, 1979, "Burn Wound Dressing With Human Amniotic Membrane," Ann. R. Coll. Surg. Engl., 61:444-447.

Brito et al., 2003, "Effect of Topical Application of Fibronectin in Duodenal Wound Healing in Rats," Acta Cirurgica Brasileira, 18(2):97-101.

Bunyaratavej et al., 2001, "Collagen Membranes: A Review," J. Periodontol., 72(2):215-229.

Chang et al., 1994, "Frozen Preservation of Human Amnion and Its Use As a Burn Wound Dressing," Chang Gung Med. J.., 17(4):316-324.

Chaplin et al., 1999, "Use of an Acellular Dermal Allograft for Dural Replacement: An Experimental Study," Neurosurgery, 45(2):320-327.

Chen et al., 1999, "Acellular Collagen Matrix As a Possible 'Off the Shelf' Biomaterial for Urethral Repair," Urology, 54(3):407-410.

Cheng et al., 1988, "Fibronectin Enhances Healing of Excised Wounds in Rats," Arch. Dermatol., 124:221-225.

Chung, et al., 1990, "Clinical Evaluation of a Biodegradable Collagen Membrane in Guided Tissue Regeneration," J. Periodontol., 61(12):732-736.

Chvapil et al., 1973, "Medical and Surgical Applications of Collagen," Int. Rev. Connect. Tissue Res., 6:1-61.

Colocho et al., 1974, "Human Amniotic Membrane As a Physiologic Wound Dressing," Arch. Surg., 109: 370-373.

Constantino et al., 2000, "Human Dural Replacement With Acellular Dermis: Clinical Results and a Review of the Literature," Head & Neck, 22:765-771.

Davis et al., 1987, "Human Amnion Membrane Serves As a Substratum for Growing Axons In Vitro and In Vivo," Science, 236:1106-1109.

De Rotth, 1940, "Plastic Repair of Conjunctival Defects With Fetal Membranes," Arch. of Opthalm., 23(3):522-525.

Delustro et al., 1987, "Reaction to Injectable Collagen: Results in Animal Models and Clinical Use," Plast. Reconstr. Surg., 79(4):581-594.

Delustro et al.,1990, "Immune Responses to Allogeneic and Xenogeneic Implants of Collagen and Collagen Derivatives," Clin. Orthop., 260:263-279.

Demirkan et al., 2002, "The Use of Amniotic Membrane in Flexor Tendon Repair: An Experimental Model," Arch. Orthop. Trauma Surg., 122:396-399.

Dhall, 1984, "Amnion Graft for Treatment of Congenital Absence of the Vagina," Br. J. Obstet. Gynaecol., 91:279-282.

Dino et al., 1966, "Human Amnion: The Establishment of an Amnion Bank and Its Practical Applications in Surgery," J. Philipp. Med. Assoc., 42(7):357-366.

Dong et al., 2002, "Some New Aspects in Biosensors," Reviews in Mol. Biotechnol., 82:303-323.

Dua et al., 1999, "Amniotic Membrane Transplantation," Br. J. Opthalmol., 83:748-752.

Eade, 1958, "The Relationship Between Granulation Tissue, Bacteria, and Skin Grafts in Burned Patients," Plast. Reconstr. Surg., 22(1):42-55.

Eckes et al., 2000, "Fibroblast-Matrix Interactions in Wound Healing and Fibrosis," Matrix Biol., 19:325-332.

Eldad et al., 1977, "Amniotic Membranes As a Biological Dressing," S. Afr. Med. J., 51(9):272-275.

Erdener et al., 1992, "Amniotic Membrane Wrapping: An Alternative Method to the Splenorrhaphy in the Injured Spleen," Eur. J. Pediatr. Surg., 2:26-28.

Faulk et al., 1980, "Human Amnion As an Adjunct in Wound Healing," Lancet, 1:1156-1158.

Flageul et al., 1994, "Le collagène injectable: bilan après 10 ans d'utilisation en complément de las chirurgie esthétique," Annales de Chirurgie Plastique Esthétique, 39(6):765-771.

Fletcher, 2000, "The Role of Collagen in Wound Healing," Prof. Nurse, 15(8):527-530.

Friess, 1998, "Collagen—Biomaterial for Drug Delivery," Eur. J. Pharm. Biopharm., 45(2):113-136.

Fujisato et al., 1999, "Cross-Linking of Amniotic Membranes," J. Biomater. Sci. Polym. Ed., 10:1171-1181.

Gamba et al., 2000, "Experimental Abdominal Wall Defect Repaired With Acellular Matrix," Pediatr. Surg. Int., 18:327-331.

Ganatra et al., 1996, "Method of Obtaining and Preparation of Fresh Human Amniotic Membrane for Clinical Use," J. Pak. Med. Assoc., 46(6):126-128.

Gebhardt et al., 1995, "Collagen As a Delivery System for Hydrophobic Drugs: Studies With Cyclosporine," J. Ocul. Pharmacol. Ther., 11(3):319-327.

Ghalambor et al., 2000, "The Amniotic Membrane: A Suitable Biological Dressing to Prevent Infection in Thermal Burns," Medical Journal of Islamic Academy of Sciences, 13(3):115-118.

Gharib et al., 1996, "Use of Amniotic Graft in the Repair of Gastroschisis," Pediatr. Surg. Int., 11:96-99.

Goepfert, 1991, "Collagen Injections," Arch. Otolaryngol. Head Neck Surg., 117(10):1189.

Gomes et al., 1996, "Effects of Human Amniotic Membrane on Dental Socket Wound Healing Process in Rats," Journal of Dental Research, 75(5):1114, Abstract 290.

Gomes et al., 2001, "Histologic Evaluation of the Osteoinductive Property of Autogenous Demineralized Dentin Matrix on Surgical Bone Defects in Rabbit Skulls Using Human Amniotic Membrane for Guided Bone Regeneration," International Journal of Oral & Maxillofacial Implants, 16(4):563-571.

Gomes et al., 2003, "Amniotic Membrane Transplantation for Partial and Total Limbal Stem Cell Deficiency Secondary to Chemical Burn," Opthamology, 110(3):466-473.

Graham, Med. Device Tech., 9(1):18-22 (1998).

Gris et al., 2002, "Amniotic Membrane Implantation As a Therapeutic Contact Lens for the Treatment of Epithelial Disorders," Cornea, 21(1):22-27.

Gris et al., 2002, "Histologic Findings after Amniotic Membrane Graft in the Human Cornea," Opthamology, 109(3):508-512.

Gruss et al., 1978, "Human Amniotic Membrane: A Versatile Wound Dressing," Can. Med. Assoc. J., 118:1237-1246.

Guler, et al., 1993, "A Comparative Histopathological Investigation of the Effect of Lyophilized Amniotic Membrane on Wound Healing As an Allograft Material in Rats," Journal of Islamic Academy of Sciences, 6(3).

Haberal et al., 1987, "The Use of Silver Nitrate-Incorporated Amniotic Membrane As a Temporary Dressing," Burns, 13(2):159-163.

Hammer et al., 1997, "Amnion Epithelial Cells, in Contrast to Trophoblast Cells, Express All Classical HLA Class I Molecules Together With HLA-G," Am. J. Reprod. Immunol., 37:161-171.

Heiligenhaus et al., 2001, "Improvement of HSV-1 Necrotizing Keratitis With Amniotic Membrane Transplantation," Investigative Opthamology and Visual Science, 42(9):1969-1974.

Hennink et al., 2002, "Novel Crosslinking Methods to Design Hydrogels," Advanced Drug Delivery Reviews, 54:13-36.

Herne et al., 2000, "New Facial Rejuvenation Techniques," Semin. Cutan. Med. Surg., 19(4):221-231.

Hodde, 2002, "Naturally Occurring Scaffolds for Soft Tissue Repair and Regeneration," Tissue Eng., 8(2):295-308.

Honovar et al., 2000, "Amniotic Membrane Transplantation for Ocular Surface Reconstruction in Stevens-Johnson Syndrome," Opthamology, 107(5):975-979.

John et al., 2002, "Amniotic Membrane in the Surgical Management of Acute Toxic Epidermal Necrolysis," Ophthalmology, 109(2):351-360.

John, 2003, "Human Amniotic Membrane Transplantation: Past, Present, and Future," Ophthalmol. Clin. North Am., 16:43-64.

Johnson, 1937, "Insulating Patches and Absorbable Sutures Made From Fetal Membranes," New England Journal of Medicine, 216(22):978-982.

Kakishita et al., 2000, "Human Amniotic Epithelial Cells Produce Dopamine and Survive After Implantation Into the Striatum of a Rat Model of Parkinson's Disease: A Potential Source of Donor for Transplantation Therapy," Exp. Neurol., 165(1):27-34.

Kane et al., 1996, "7.10 Burn Dressings," Biomaterials Science: An Introduction to Materials in Medicine, 360-370.

Kassouf et al., 2001, "Collagen Injection for Treatment of Urinary Incontinence in Children," J. Urol., 165(5):1666-1668.

Kershen et al., 2002, "Beyond Collagen: Injectable Therapies for the Treatment of Female Stress Urinary Incontinence in the New Millennium," Urol. Clin. North Am., 29(3):559-574.

Kim et al., 1995, "Transplantation of Preserved Human Amniotic Membrane for Surface Reconstruction in Severely Damaged Rabbit Corneas," Cornea, 14(5):473-484.

Kim et al., 2000, "Amniotic Membrane Patching Promotes Healing and Inhibits Proteinase Activity on Wound Healing Following Acute Corneal Alkali Burn," Experimental Eye Research, 70: 329-337.

Kirschbaum et al., 1963, "Use of Amnion in Extensive Burns," Third International Congress of Plastic Surgery, Washington, D.C., Oct. 13-18, 1963, Abstracts of Papers, p. 21, Abstract 33.
Klein, 2001, "Skin Filling. Collagen and Other Injectables of the Skin," Dermatol. Clin., 19(3):491-508.
Klen et al., 1976, "Influence of Ionizing Sterilization on the Permeability of Human Chorio-Amniotic, Dermo-Epidermal and Fascial Grafts," Res. Exp. Med., 167(1):15-21.
Koizumi et al., 2000, "Cultivation of Corneal Epithelial Cells on Intact and Denuded Human Amniotic Membrane," Investigative Opthamology and Visual Science, 41(9):2506-2513.
Koizumi et al., 2000, "Growth Factor mRNA and Protein in Preserved Human Amniotic Membrane," Current Eye Research, 20(3): 173-177.
Kubo et al., 2001, "Immunogenicity of Human Amniotic Membrane in Experimental Xenotransplantation," Invest. Ophthalmol. Vis. Sci., 42(7):1539-1546.
Kucan et al., 1982, "Amniotic Membranes As Dressings Following Facial Dermabrasion," Ann. Plast. Surg., 8(6):523-527.
Lee et al., 1996, "Effect of Amniotic Fluid in Corneal Sensitivity and Nerve Regeneration After Excimer Laser Ablation," Cornea, 15(5):517-524.
Lee et al., 1997, "Amniotic Membrane Transplantation for Persistent Epithelial Defects With Ulceration," Am. J. Opthalm., 123(3):303-312.
Lee et al., 1998, "Mesothelial Cell Regeneration in Purified Human Amnion Membrane Grafts Implanted in Dog Pericardium," Tissue Engineering, 4(2):131-141.
Lee et al., 2001, "Biomedical Applications of Collagen," Int. J. Pharm., 221:1-22.
Lee et al., 2002, "Laminin Modified Infection-Preventing Collagen Membrane Containing Silver Sulfadiazine-Hyaluronan Microparticles," Artif. Organs, 26(6):521-528.
Lightner, 2002, "Review of the Available Urethral Bulking Agents," Curr. Opin. Urol., 12(4):333-338.
Mantovani et al., 2002, "Reconstructive Urethroplasty Using Porcine Acellular Matrix: Preliminary Results," 59th Convegno Associazione Urologi Lombardi—Milano, 26 Gennaio 2002, pp. 127-128 (Abstract in English).
Marzaro et al., 2002, "Autologous Satellite Cell Seeding Improves In Vivo Biocompatibility of Homologous Muscle Acellular Matrix Implants," International J. Mol. Med., 10:177-182.
Massee et al., 1962, "Use of Fetal Membranes As Replacement for Pelvic Peritoneum After Pelvic Exenteration in the Dog," Surg. Forum, 13:407-408.
Mattson et al., 1995, "Treatment of Intrabony Defects With Collagen Membrane Barriers," J. Periodontol., 66(7):635-645.
Mattson et al., 1999, "The Use of 2 Bioabsorbable Barrier Membranes in the Treatment of Interproximal Intrabony Periodontal Defects," J. Periodontol., 70(5):510-517.
McIndoe et al., 1938, "An Operation for the Cure of Congenital Absence of the Vagina," Journal of Obstetrics and Gynaecology, 490-494.
McPherson et al., 1986, "An Examination of the Biologic Response to Injectable Glutaraldehyde Cross Linked Collagen Implants," J. Biomed. Mater. Res., 20:93-107.
McPherson, 1992, "The Utility of Collagen-Based Vehicles in Delivery of Growth Factors for Hard and Soft Tissue Wound Repair," Clin. Mater., 9:225-234.
Meinert et al., 2001, "Proteoglycans and Hyaluronan in Human Fetal Membranes," Am. J. Obstet. Gynecol., 184(4): 679-685.
Meller et al., 2000, "Amniotic Membrane Transplantation for Symptomatic Conjunctivochalasis Refractory to Medical Treatments," Cornea, 19(6):796-803.
Meller et al., 2000, "Amniotic Membrane Transplantation for Acute Chemical or Thermal Burns," Opthamology, 107(5):980-989.
Merguerian et al., 2000, "Acellular Bladder Matrix Allografts in the Regeneration of Functional Bladders: Evaluation of Large-Segment (>24 $cm^2$) Substitution in a Porcine Model," BJU Intl., 85:894-898.
Mligiliche et al., 2002, "Extracellular Matrix of Human Amnion Manufactured Into Tubes As Conduits for Peripheral Nerve Regeneration," J. Biomed. Mater. Res., 63:591-600.

Morton et al., 1986, "Human Amnion in the Treatment of Vaginal Malformations," Br. J. Obstet. Gynaecol., 93:50-54.
Muralidharan et al., 1991, "A New Biological Membrane for Pericardial Closure," J. Biomed. Mater. Res., 25:1201-1209.
Murata et al., 1998, "Human Amniotic Membrane on Guided Bone Regeneration in Skull Defects," Journal of Dental Research, 77:840, Abstract 1668.
Nguyen et al., Biomaterials, 23(22):4307-4314 (2002).
Nisolle et al., 1992, "Vaginoplasty Using Amniotic Membranes in Cases of Vaginal Agenesis or After Vaginectomy," J. Gynecol. Surg., 8:25-30.
Oremus et al., 2002, "A Survey of Physician Efficacy Requirements to Plan Clinical Trials," Pharmacoepidemiology Drug Saf., 11(8):677-685.
Ozcan et al., 1997, "Combined Use of Root Conditioning, Fibrin-Fibronectin System and a Collagen Membrane to Treat a Localized Gingival Recession: A 10-Case Report," J. Marmara Univ. Dent. Fa., 2(4):588-598.
Ozeren et al., 1998, "The Effects of Human Amniotic Membrane and Fibrin Sealant in the Prevention of Postoperative Adhesion Formation in the Rabbit Ovary Model," Australian & New Zealand Journal of Obstetrics & Gynaecology, 38(2):207-209.
Pannek et al., 2001, "Particle Migration After Transurethral Injection of Carbon Coated Beads for Stress Urinary Incontinence," J. Urol., 166(4):1350-1353.
Parnigotto et al., 2000, "Experimental Defect in Rabbit Urethra Repaired with Acellular Aortic Matrix," Urol. Res., 28:46-51.
Patino et al., 2002, "Collagen as an Implantable Material in Medicine and Dentistry", J. Oral Implantol., 28(5):220-225.
Paul et al., 1992, "Use of a Collagen Barrier to Enhance Healing in Human Periodontal Furcation Defects," Int. J. Periodontics Restorative Dent., 12(2):123-131.
Peppas et al., Eur. J. Pharm. Biopharm., 50(1):27-46 (2000).
Piazza et al., 1992, "Neovaginoplasty With McInndoe Technic and Use of Amniotic Membrane: Study With 15 Patients," Rev. Bras. Ginecol. Obstet., 14:224-226.
Pigeon, 1960, "Treatment of Second-Degree Burns with Amniotic Membranes," Can. Med. Assoc. J., 83:844-845.
Pires et al., 1999, "Amniotic Membrane Transplantation for Symptomatic Bullous Keratopathy," Archives of Opthamology, 117:1291-1297.
Power et al., 1995, "Analysis of the Acute Ophthalmic Manifestations of the Erythema Multiforme/Stevens-Johnson Syndrome/Toxic Epidermal Necrolysis Disease Spectrum," Ophthalmology, 102(11):1669-1676.
Prabhasawat et al., 1997, "Comparison of Conjunctival Autografts, Amniotic Membrane Grafts, and Primary Closure for Pterygium Excision," Ophthalmology, 104(6):974-985.
Prabhasawat et al., 1997, "Impression Cytology Study of Epithelial Phenotype of Ocular Surface Reconstructed by Preserved Human Amniotic Membrane," Arch. Ophthalmol., 115(11):1360-1367.
Prasad et al., 1986, "Use of Amnion for the Treatment of Stevens-Johnson Syndrome," J. Trauma, 26(10):945-946.
Prathiba et al., 2000, "Cutaneous Wound Healing: Significance of Proteoglycans in Scar Formation," Current Science, 78(6):1-5.
Quinby et al., 1982, "Clinical Trials of Amniotic Membranes in Burn Wound Care," Plast. Reconstr. Surg., 70:711-717.
Quteish et al., 1992, "The Use of Irradiated-Crosslinked Human Collagen Membrane in Guided Tissue Regeneration," J. Clin. Periodontol., 19(7):476-484.
Ramakrishnan et al., 1983, "Human Amniotic Membrane as a Temporary Biologic Dressing in Complicated Burns in a Developing Country," Journal of Burn Care & Rehabilitation, 4(3):202-204.
Rao et al., 1981, "Use of Dry Human and Bovine Amnion As a Biological Dressing," Arch. Surg., 116:891-896.
Rao, 1995, "Recent Developments of Collagen-Based Materials for Medical Applications and Drug Delivery Systems," J. Biomater. Sci. Polym. Ed., 7(7):623-645.
Reddy et al., 2000, "Regeneration of Functional Bladder Substitutes Using Large Segment Acellular Matrix Allografts in a Porcine Model," J. Urol., 164:936-941.

Rennekampff et al., 1994, "Evaluation of Amniotic Membrane As Adhesion Prophylaxis in a Novel Surgical Gastroschisis Model," J. Invest. Surg., 7:187-193.

Rigal-Sastourne et al., 2002, "Brulures Corneennes Et Metalloproteases: Influence Des Greffes De Membranes Amniotiques," J. Fr. Ophtalmol., 25:685-693.

Robson et al., 1973, "Amniotic Membranes as a Temporary Wound Dressing," Surg. Gynecol. Obstet., 136: 904-906.

Robson et al., 1973, "Quantitative Comparison of Biological Dressings," J. Surg. Res., 14: 431-434.

Robson et al., 1973, "The Effect of Human Amniotic Membranes on the Bacteria Population of Infected Rat Burns," Ann. Surg., 177(2):144-149.

Robson et al., 1974, "Clinical Experiences With Amniotic Membranes As a Temporary Biologic Dressing," Conn. Med., 38(9):449-451.

Sabella, 1913, "Use of Fetal Membranes in Skin Grafting," Med. Records NY, 83:478-480.

Sakuragawa et al., 1992, "Amniotic Tissue Transplantation: Clinical and Biochemical Evaluations for Some Lysosomal Storage Diseases," Brain Dev., 14(1):7-11.

Salisbury et al., 1980, "Comparison of the Bacterial Clearing Effects of Different Biologic Dressings on Granulating Wounds Following Thermal Injury," Plast. Reconstr. Surg, 66(4):596-598.

Sawhney, 1989, "Amniotic Membrane As a Biological Dressing in the Management of Burns," Burns, 15(5):339-342.

Schiff et al., 2003, "Towards a Sutureless Vasovasostomy: Use of Biomaterials and Surgical Sealants in a Rodent Vasovasostomy Model," Fertility and Sterility, 80(Suppl. 3): S92, Abstract O-240.

Schmedlen et al., Biomaterials, 23:4325-4332 (2002).

Shieh et al., 1997,"Development and Clinical Evaluation of a Root Coverage Procedure Using a Collagen Barrier Membrane," J. Periodontol., 68(8):770-778.

Shimazaki et al., 1997, "Amniotic Membrane Transplantation for Ocular Surface Reconstruction in Patients With Chemical and Thermal Burns," Opthamology, 104(12):2068-2076.

Shimazaki et al., 2000, "Association of Preoperative Tear Function With Surgical Outcome in Severe Stevens-Johnson Syndrome," Ophthalmology, 107(8):1518-1523.

Shimazaki et al., 2002, "Transplantation of Human Limbal Epithelium Cultivated on Amniotic Membrane for the Treatment of Severe Ocular Surface Disorders," Opthamology, 109(7):1285-1290.

Shun et al., 1983, "Human Amnion in the Treatment of Chronic Ulceration of the Legs," Med. J. Aust., 2:279-283.

Silverton et al., 1979, "The Use of Amniotic Membrane in Acute Massive Full-Thickness Loss of the Abdominal Wall From Clostridial Myonecrosis," Ann. Plast. Surg., 3(6):558-566.

Singh et al., 2003, "Properties of Air Dried Radiation Processed Amniotic Membranes Under Different Storage Conditions," Cell and Tissue Banking, 4:95-100.

Skelhorne et al., Med. Device Tech., 13(9):19-23 (2002).

Solomon et al., 2002, "Amniotic Membrane Grafts for Nontraumatic Corneal Perforations, Descemetoceles, and Deep Ulcers," Opthamology, 109(4):694-703.

Sorsby et al., 1946, "Amniotic Membrane Grafts in Caustic Burns of the Eye," Br. J. Opthamlol., 30:337-345.

Spira et al., 1994, "Human Amnion Collagen for Soft Tissue Augmentation—Biochemical Characterizations and Animal Observations," J. Biomed. Mat. Res., 28:91-96.

Stern, 1913, "The Grafting of Preserved Amniotic Membrane to Burned and Ulcerated Surfaces, Substituting Skin Grafts: A Preliminary Report," Journal of the American Medical Association, LX(13):973-974.

Subrahmanyam, 1995, "Amniotic Membrane As a Cover for Microskin Grafts," British Journal of Plastic Surgery, 48:477-478.

Szabo et al., 2000, "Evaluation of Seprafilm and Amniotic Membrane As Adhesion Prophylaxis in Mesh Repair of Abdominal Wall Hernia in Rats," European Surgical Research, 32:125-128.

Talmi et al., 1990, "Use of Human Amniotic Membrane As a Biologic Dressing," European Journal of Plastic Surgery, 13:160-162.

Talmi et al., 1991, "Antibacterial Properties of Human Amniotic Membranes," Placenta, 12:285-288.

Tancer et al., 1979, "Vaginal Epithelialization with Human Amnion," Obstet. Gynecol., 54(3):345-349.

Ti et al., 2001, "Amniotic Membrane Transplantation in Entropion Surgery," Opthamology, 108(7):1209-1217.

Trelford et al., 1972, "Amnion Autografts and Allografts As a Cover for Skin Defects in Sheep," J. Med., 3:81-87.

Trelford et al., 1972, "Considerations of the Amnion As an Autograft and As an Allograft in Sheep," J. Med., 3:231-241.

Trelford et al., 1973, "The Feasibility of Making an Artificial Vagina At the Time of Anterior Exenteration," Oncology, 28:398-401.

Trelford et al., 1975, "Amnion Autografts, Permanent Structure," J. Med., 6(3&4):243-247.

Trelford et al., 1973, "Amniotic Membrane As a Living Surgical Dressing in Human Patients," Oncology, 28:358-364.

Trelford et al., 1975, "Implanted Amniotic Membrane as an Autograft and as an Allograft," J. Med., 6(2):169-180.

Trelford-Sauder et al., 1977, "Replacement of the Peritoneum With Amnion Following Pelvic Exenteration," Surg. Gynecol. Obstet., 145:699-701.

Trelford et al., 1979, "The Amnion in Surgery, Past and Present," Am. J. Obstet. Gynecol., 134(7):833-845.

Troensagaard-Hansen et al., 1950, "Amniotic Grafts in Chronic Skin Ulceration," Lancet, 1:859-860.

Tseng et al., 1997, "Amniotic Membrane Transplantation for Conjunctival Surface Reconstruction," Am. J. Ophthalmol., 124(6):765-774.

Tseng et al., 1998, "Amniotic Membrane Transplantation With or Without Limbal Allografts for Corneal Sufrace Reconstruction in Patients With Limabal Stem Cell Deficiency," Archives of Opthamology, 116:431-441.

Tseng, 2001, "Amniotic Membrane Transplantation for Ocular Surface Reconstruction," Biosci. Rep., 21(4):481-489.

Tsubota et al., 1996, "Surgical Reconstruction of the Ocular Surface in Advanced Ocular Cicatricial Pemphigoid and Stevens-Johnson Syndrome," Am. J. Ophthalmol., 122(1):38-52.

Ueta et al., 2002, "Immunosuppressive Properties of Human Amniotic Membrane for Mixed Lymphocyte Reaction," Clinical and Experimental Immunology, 129: 464-470.

Voytik-Harbin et al., 1997, "Identification of Extractable Growth Factors From Small Intestinal Submucosa," J. Cell Biochem., 67:478-491.

Wagshall et al., 2002, "Acellular Dermal Matrix Allograft in the Treatment of Muciogingival Defects in Children: Illustrative Case Report," J. Dentistry for Children, 79:39-43.

Walker et al., 1977, "Use of Fresh Amnion As a Burn Dressing," J. Pediatr. Surg., 12(3):391-395.

Wallace et al., 1988, Collagen vol. III Biotechnology, Chapter 5, 116-144.

Wang et al., 1994, "Evaluation of an Absorbable Collagen Membrane in Treating Class II Furcation Defects," J. Periodontol., 65(11):1029-1036.

Wang et al., 1997, "Corneal Haze Is Reduced by Amniotic Membrane Matrix in Excimer Laser Photoablation in Rabbits," Investig. Opthalmology and Visual Science Abstract Book Part I, Annual Meeting, Ft. Lauderdale, Florida May 11-16, 1997, 38(4):S405, Abstract 1908-B701.

Wang et al., 1999, "Clinical Comparison of Two Techniques for Treatment of Gingival Recession," J. Dent. Res., 78 (IADR Abstracts):119, Abstract 106.

Ward et al., 1984, "The Long Term Results of the Use of Human Amnion in the Treatment of Leg Ulcers," British Journal of Plastic Surgery, 37: 191-193.

Ward et al., 1989, "The Healing of Chronic Venous Leg Ulcers With Prepared Human Amnion," Br. J. Plast. Surg., 42:463-467.

Wefer et al., 2002, "Homologous Acellular Matrix Graft for Vaginal Repair in Rats: A Pilot Study for a New Reconstructive Approach," World J. Urol., 20:260-263.

Yannas et al., 1980, "Design of an Artificial Skin: Control of Chemical Composition," J. of Biomed. Mat. Res., 14:107-132.

Yarborough et al., 1991, "Collagen Injections. A Case Study in the Erosion of the Medical Profession," Arch. Otolaryngol. Head Neck Surg., 117(1):270-272.

Young et al., 1991, "The Use of an Amniotic Membrane Graft to Prevent Postoperative Adhesions," Fertil. Steril., 55(3): 624-628.

Yukna et al., 1996, "Multi-Center Evaluation of Bioabsorbable Collagen Membrane for Guided Tissue Regeneration in Human Class II Furcations," J. Periodontol., 67(7):650-657.

Zahedi et al., 1998, "A 2-Year Clinical Evaluation of a Diphenylphosphorylazide-Cross-Linked Collagen Membrane for the Treatment of Buccal Gingival Recession," J. Periodontol., 69(9):975-981.

Zimmermann et al., 2000, "Hydrogel-Based Non-Autologous Cell and Tissue Therapy," BioTechniques, 29(3):564-572, 574, 576-581.

* cited by examiner

UMBILICAL CORD BIOMATERIAL FOR MEDICAL USE

RELATED APPLICATIONS

This application claims the benefit of U.S. Provisional Application No. 60/838,132, filed Aug. 15, 2006, the contents of which are hereby incorporated by reference in its entirety.

1. FIELD OF THE INVENTION

The present invention generally relates to biomaterials derived from the umbilical cord membrane, compositions comprising the umbilical cord membrane, and methods of treatment using the compositions.

2. BACKGROUND OF THE INVENTION

The repair or treatment of various body tissues, such as skin, organs, and the like, has been accomplished using collagen compositions, including membranes comprising collagen. A need exists, however, for additional such compositions, including ones that are able to handle loads well.

3. SUMMARY OF THE INVENTION

The present invention provides biomaterials derived from umbilical cord. In certain embodiments, the biomaterial comprises an umbilical cord membrane. The present invention provides methods of making the umbilical cord biomaterial, and of using the biomaterial, e.g., to repair organs and tissues.

In one aspect, the present invention provides a biomaterial comprising an isolated mammalian umbilical cord membrane. In a specific embodiment, the biomaterial comprises at least one umbilical vessel (e.g., an umbilical artery or umbilical vein). In another specific embodiment, the biomaterial comprises Wharton's jelly. In another specific embodiment, the biomaterial comprises Wharton's jelly but lacks umbilical vessels. In another specific embodiment, the biomaterial comprises the umbilical cord membrane, Wharton's jelly, and all three umbilical vessels. The umbilical cord biomaterial is not, however, an umbilical cord that has not been processed in any manner.

In more specific embodiments of any of the above embodiments, the biomaterial comprises less water by weight than native umbilical cord membrane in vivo, e.g., the biomaterial comprises 40%, 30%, 20%, 10% or less water by weight. In other more specific embodiments, the biomaterial comprises at least 60%, at least 70%, or at least 80% water by weight. In another specific embodiment, the biomaterial is decellularized prior to use. In another specific embodiment, the biomaterial is not decellularized prior to use. In another specific embodiment, the umbilical cord membrane of the biomaterial is cut or slit longitudinally. In another specific embodiment, the biomaterial is substantially flat. In another specific embodiment, the biomaterial is substantially tubular. In another specific embodiment, the biomaterial comprises artificially crosslinked proteins.

In another specific embodiment, the umbilical cord biomaterial comprises an exogenous bioactive molecule, that is, a bioactive molecule not obtained from the umbilical cord used to make the biomaterial. In a more specific embodiment, said bioactive molecule is a cytokine or growth factor. In another more specific embodiment, said bioactive molecule is an extracellular matrix protein. In another more specific embodiment, said extracellular matrix protein is collagen, fibronectin, elastin, vitronectin, or hyaluronic acid. In a more specific embodiment, said bioactive molecule is hyaluronic acid. In an even more specific embodiment, said hyaluronic acid is crosslinked to said umbilical cord membrane. In another specific embodiment, said biomaterial comprises an exogenous polymer. In a more specific embodiment, said exogenous polymer is a synthetic biodegradable polymer or an anionic polymer. In another more specific embodiment, said synthetic biodegradable polymer is a polyhydroxyalkanoate. In a more specific embodiment, said anionic polymer is dextran sulfate or pentosan polysulfate. In another specific embodiment, the bioactive molecule is an antibiotic, a hormone, a growth factor, an anti-tumor agent, an anti-fungal agent, an anti-viral agent, a pain medication, an anti-histamine, an anti-inflammatory agent, an anti-infective agent, a wound healing agent, a wound sealant, a cellular attractant or a scaffolding reagent. In another specific embodiment, the bioactive molecule is a small molecule, e.g., a small organic molecule, e.g., a drug.

In another specific embodiment, the umbilical cord biomaterial comprises a hydrogel composition. In a more specific embodiment, said hydrogel composition comprises a polyvinyl alcohol, a polyethylene glycol, a hyaluronic acid, a dextran, or a derivative or analog thereof.

The umbilical cord biomaterial can also comprise, e.g., be seeded with, one or more types of stem and/or progenitor cells. In a specific embodiment, the biomaterial comprises an exogenous stem cell, that is, a stem cell not native to the umbilical cord from which the biomaterial is derived, or from an individual different from the umbilical cord donor. In specific embodiments, the stem cell is a placental stem cell, a mesenchymal stem cell, an embryonic stem cell, an adult stem cell, or a somatic stem cell. In a more specific embodiment, the somatic stem cell is a neural stem cell, a hepatic stem cell, a pancreatic stem cell, an endothelial stem cell, a cardiac stem cell, a stromal cell, or a muscle stem cell. In another specific embodiment, the umbilical cord biomaterial comprises an exogenous adult (e.g., fully-differentiated or committed progenitor) cell.

In another embodiment, the invention provides laminates comprising the umbilical cord biomaterial. Such laminates can comprise layers of umbilical cord biomaterial, or one or more layers of umbilical cord biomaterial layered with one or more layers of another material. The layers can be substantially aligned, or can be offset, e.g., overlapping, to form, e.g., a laminate of biomaterial longer and/or wider than an umbilical cord. Thus, in one embodiment, the invention provides a laminate comprising a plurality (e.g., 2, 3, 4, 5, 6, 7, 8, 9, 10, etc.) of layers, wherein at least one of the layers comprises an umbilical cord biomaterial. In a specific embodiment, said laminate comprises one or more layers of an amniotic membrane material. In a more specific embodiment, said amniotic membrane material is a dried amniotic membrane laminated to said umbilical cord membrane. In another more specific embodiment, said amniotic membrane material has been sonicated or otherwise disrupted. In another specific embodiment, at least some of the proteins in at least one of the layers of the laminate are artificially crosslinked, either to other proteins in the same layer, or to proteins in one or more adjoining layers.

The invention further provides laminates comprising the umbilical cord biomaterial and other useful compounds. For example, in one embodiment, the invention provides a laminate comprising umbilical cord biomaterial and an exogenous stem cell or an exogenous adult cell. In another embodiment, the laminate comprises a hydrogel composition. In a specific embodiment, said hydrogel composition comprises a polyvinyl alcohol, a polyethylene glycol, a hyaluronic acid, a dextran, or a derivative or analog thereof.

The invention also provides a method of producing a biomaterial comprising isolating and decellularizing a biomaterial comprising an umbilical cord membrane. In a specific embodiment, the biomaterial comprises Wharton's jelly, or one or more umbilical cord vessels. In another embodiment, the method comprises isolating said umbilical cord membrane from one or more umbilical cord vessels. The method may further comprise drying said biomaterial to less than 20% water by weight. In various embodiments, said biomaterial is dried at about 26° C. to about 65° C., or at about 35° C. to about 50° C. The composition can, for example, be dried with a hygroscopic compound. In another embodiment, the biomaterial is freeze dried, or dried using vacuum. Said decellularizing may, for example, comprise contacting the umbilical cord membrane with a detergent solution, for example, a solution comprising 0.01-2.0% deoxycholic acid. The detergent may be a nonionic detergent, an anionic detergent, or a combination thereof. In specific embodiments, said detergent is Triton X-100 or sodium dodecyl sulfate, or a combination thereof.

The invention further provides methods of making a laminate comprising an umbilical cord membrane biomaterial. Such a method can comprise crosslinking at least some proteins in at least one layer of said laminate. The method of making the laminate, in one embodiment, comprises layering a plurality of umbilical cord membranes in contact with each other to form a laminate. In a specific embodiment, one or more of said membranes comprise less than 20% water by weight prior to said layering. In another specific embodiment, said laminate is dried to less than 20% water by weight after said layering. In other specific embodiments, one or more of said membranes comprise at least 60%, at least 70% or at least 80% water by weight. In another specific embodiment, said laminate comprises at least 60%, at least 70%, or at least 80% water by weight.

The invention also provides for the use of the umbilical cord membrane biomaterial to deliver one or more therapeutic agents to a subject. In one embodiment, the invention provides a method of delivering a therapeutic agent to a subject comprising contacting the subject with an umbilical cord membrane biomaterial, or laminate thereof, wherein said composition or laminate comprises a therapeutic agent. In a specific embodiment, said subject is a human. In other specific embodiments, said therapeutic agent is an antibiotic, an anti-cancer agent, an anti-bacterial agent, an anti-viral agent, a vaccine, an anesthetic, an analgesic, an anti-asthmatic agent, an anti-inflammatory agent, an anti-depressant, an anti-diabetic agent, an anti-psychotic, a central nervous system stimulant, a hormone, an immunosuppressant, a muscle relaxant, or a prostaglandin.

The invention further provides a method of using an umbilical cord biomaterial, e.g., one that comprises an isolated umbilical cord membrane, in the repair of a tympanic membrane deformity, comprising contacting said tympanic membrane with such a biomaterial. In a specific embodiment, the deformity is a perforation, which may be, e.g., a central perforation or a marginal perforation. The perforation may be caused by, e.g., trauma, or as part of a surgical procedure. In a more specific embodiment, said contacting is sufficient to occlude the perforation. In another more specific embodiment, said perforation has not healed spontaneously within two months of developing the perforation. In another specific embodiment, said deformity is an atelectatic tympanic membrane, a deformity relating to a choleastoma, a retraction pocket or a deformity resulting from a tympanosclerosis.

The invention also provides for the repair of other deformities using the umbilical cord membrane biomaterial. For example, the invention provides a method of repairing a nasal septum having a perforation, comprising contacting said septum with a biomaterial comprising an umbilical cord biomaterial, e.g., one comprising an isolated mammalian umbilical cord membrane. In a more specific embodiment, said method comprises contacting cartilage within said septum with said biomaterial.

As used herein, "exogenous bioactive compound" means a molecule introduced into the biomaterial that has a detectable effect on one or more biological systems. Examples of bioactive compounds are listed, without limitation, in Section 5.1.2, below.

As used herein, "substantially flat," in reference to umbilical cord biomaterial, means that the majority of the umbilical cord biomaterial is planar, but can comprise differences in thickness, whether naturally-occurring or artificially-induced, e.g., natural variations in membrane thickness, ridges, patterns, raised areas, warps, and the like, induced, e.g., during drying on a mesh.

As used herein, "substantially tubular," in reference to umbilical cord biomaterial, means that the majority of the umbilical cord biomaterial is tubular (i.e., circular, ovoid, or irregular in cross-section, and comprising the material defining an interior or lumen). The substantially tubular biomaterial can be a closed tube or partially open tube.

As used herein, "umbilical cord biomaterial" means any biomaterial comprising an isolated umbilical cord outer membrane, particularly a biomaterial manufactured or derived from umbilical cord, and includes, e.g., dried whole umbilical cord, dried umbilical cord membrane (with or without vessels), umbilical cord membrane laminated with a second material, etc. The term does not, however, encompass an umbilical cord that has not been treated or manipulated in any manner, that is, an umbilical cord that has not been modified from an in vivo state.

4. BRIEF DESCRIPTION OF THE FIGURES

Figure 4:
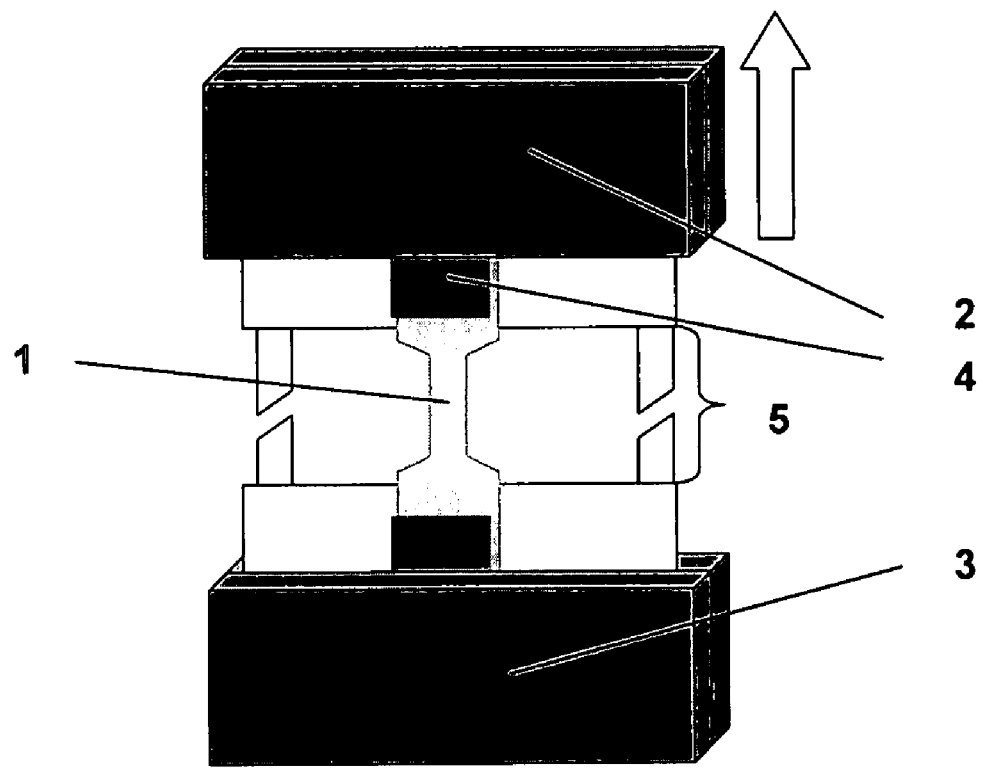

FIG. 4 depicts a schematic of tensile testing of membrane samples based on American Society for Testing and Materials (ASTM) standard D1708. A dog bone shaped sample 1 is mounted in a rectangular support of vellum paper. The membrane and the support are incubated in PBS for 1 hour at 37° C. The support keeps the membrane flat and eases loading into the mechanical tester. The tester comprises and upper grip 2 and a lower grip 3. Once the support and membrane have been secured in the grips of the mechanical tester with glue 4, the supporting struts 5 are cut and the sample can be tested with no interference from the vellum support.

Figure 5A:
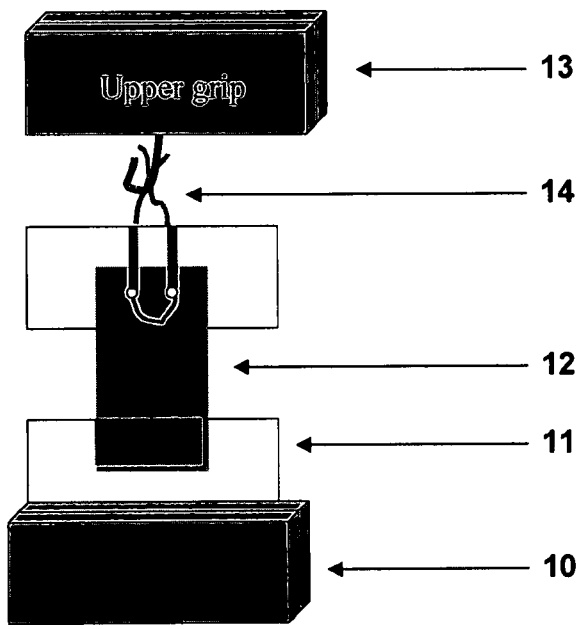
Figure 5B:
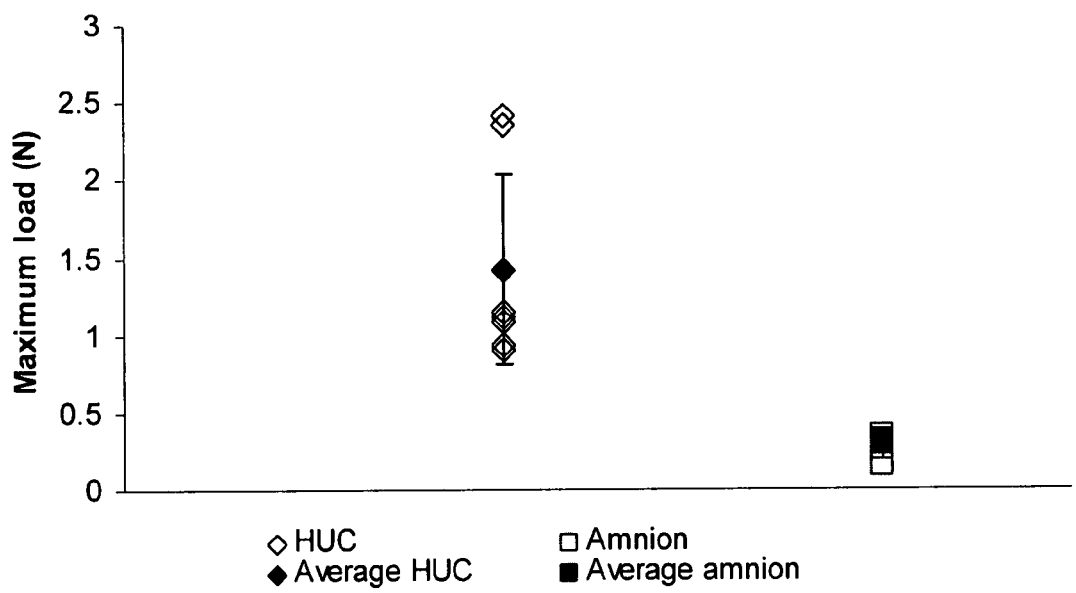

FIG. 5A depicts a suture pull-out assay apparatus with an lower grip 10 holding vellum paper 11 to which a 1×2 cm section of umbilical cord biomaterial 12 is glued, and an upper grip 13 attached to a suture 14 that passes through the umbilical cord biomaterial. Force was applied upwards throught the suture at approximately 12.7 mm/min. FIG. 5B depicts results of a comparison of the human umbilical cord biomaterial (HUC) and dried human amniotic membrane pull-out resistance in Newtons (N).

5. DETAILED DESCRIPTION OF THE INVENTION

5.1 Umbilical Cord Biomaterial
5.1.1 Description

The umbilical cord biomaterial of the invention is derived from a mammalian umbilical cord or part thereof that comprises an umbilical cord membrane (that is, the outer membrane of the umbilical cord). The umbilical cord is a substantially tubular organ, typically 10-15 cm in length, that connects the fetus to the placenta and houses the umbilical vessels. The umbilical cord comprises an outer membrane that wraps around two umbilical arteries and one umbilical vein, which are contained within a ground substance known as Wharton's jelly. The main components of Wharton's jelly are proteoglycans. Wharton's jelly also contains large, stellate fibroblasts and macrophages.

The umbilical cord membrane biomaterial of the invention typically comprises only the umbilical cord membrane, but can also comprise Wharton's jelly and/or one or more of the umbilical vessels. In one embodiment, the umbilical cord biomaterial is an umbilical cord membrane substantially isolated from the remaining umbilical cord components (e.g., Wharton's jelly and umbilical vessels). In another embodiment, the umbilical cord biomaterial comprises an umbilical cord membrane and Wharton's jelly (that is, the ground material in which the umbilical cord vessels are contained in the intact umbilical cord) that are isolated from the remaining umbilical cord components (e.g., umbilical cord vessels). In another specific embodiment, the umbilical cord membrane biomaterial comprises the membrane, Wharton's jelly and one or more umbilical cord vessels. In another embodiment, the umbilical cord biomaterial comprises an isolated umbilical cord (e.g., comprising Wharton's jelly and vessels, Wharton's jelly only, or vessels only) that has been flattened into a sheet or strip. The umbilical cord membrane biomaterial can be a substantially tubular structure from which the contents (Wharton's jelly and vessels) have been removed. The biomaterial can also comprise an umbilical cord membrane that has been slit or cut for part or all of the length of the umbilical cord to expose the contents of the umbilical cord.

In a specific embodiment, the biomaterial, comprising umbilical cord membrane and/or Wharton's jelly and/or vessels) can be decellularized. In another specific embodiment, the biomaterial comprises umbilical cord membrane-associated cells or Wharton's jelly-associated cells that have been killed. In another specific embodiment, the biomaterial comprises umbilical cord membrane-associated cells or Wharton's jelly-associated cells that have been maintained in a living state.

The umbilical cord biomaterial of the invention can be derived from the umbilical cord of any mammal, for example, from equine, bovine, porcine or catarrhine sources, but is most preferably derived from human umbilical cord.

The umbilical cord biomaterial is preferably dry or substantially dry. In a preferred embodiment, the umbilical cord biomaterial is substantially dry, i.e., is 20% or less water by weight. When dry, the umbilical cord biomaterial can be substantially flat. The dry biomaterial may, in another embodiment, substantially retain the shape of the native umbilical cord, that is, the dry membrane may be substantially tubular. The umbilical cord biomaterial can also be shaped to assume different conformations, e.g., can be curved, cut, molded, or the like, to fit to a part of the body.

In another preferred embodiment, the umbilical cord biomaterial has not been protease-treated, heat-denatured or artificially (e.g., chemically or radiologically) crosslinked. In another embodiment, the umbilical cord biomaterial comprises artificially crosslinked proteins, e.g., chemically or radiologically crosslinked collagen. In other embodiments, the umbilical cord biomaterial contains substantially no structural proteins that are artificially crosslinked. For example, in one embodiment, the umbilical cord biomaterial is not fixed. A preferred umbilical cord biomaterial is produced by the methods disclosed herein (see Section 5.1.4, below, and Examples 1 and 2).

When the umbilical cord biomaterial is substantially dry, it is typically about 0.001 g/cm$^2$ to about 0.006 g/cm$^2$. In a specific embodiment, a single layer of the acellular, dried umbilical cord biomaterial is approximately 50 microns to 250 microns in thickness, typically approximately 90 microns to 220 microns in thickness. In other specific embodiments, a single layer of the umbilical cord biomaterial is approximately 75-200 microns, 100-200 microns, 100-220 microns, 120-220 microns, or 150-250 microns in thickness in the dry state. In another embodiment, the average thickness of the umbilical cord biomaterial is about 157 microns (e.g., ±20%). In another specific embodiment, the pull out strength of the dried umbilical cord biomaterial is approximately 1.5 Newtons (N), compared to a pull out strength of a dried amniotic membrane material at approximately 0.4N.

Generally, the umbilical cord biomaterial is sided, that is, the umbilical cord biomaterial comprises an epithelial side (from the interior of the umbilical cord), and an outer, mesothelial side (from the exterior of the umbilical cord).

Generally, the umbilical cord biomaterial is non-immunogenic.

In various embodiments, the umbilical cord biomaterial comprises particular cytokines, i.e., interleukin (IL)-1b, IL-2, IL-3, IL-6, IL-7, IL-12, IL-15, IFN-α, MIP-1b, and/or MCP-1.

In one embodiment, the umbilical cord biomaterial is translucent. In other embodiments, the umbilical cord biomaterial is opaque, or is colored or dyed, e.g., permanently colored or dyed, using a medically-acceptable dyeing or coloring agent. Such an agent may be adsorbed onto the biomaterial, or the biomaterial may be impregnated or coated with such an agent. In this embodiment, any known non-toxic, non-irritating coloring agent or dye may be used.

The umbilical cord biomaterial comprises of collagen (types I, III and IV; typically about 75%-80%% of the matrix of the biomaterial), fibronectin, elastin, and may further comprise glycosaminoglycans, (GAGs, e.g., hyaluronic acid) and/or proteoglycans. Typically, laminin is not present, or is present in trace amounts (i.e., less than 0.1% of the dry weight of the biomaterial). Typically, the umbilical cord biomaterial comprises collagen types I, III, IV, V, VI and VII. In certain embodiments, the umbilical cord biomaterial can comprise non-structural components, such as, for example, one or more growth factors, e.g., platelet-derived growth factors (PDGFs), vascular-endothelial growth factor (VEGF), fibroblast growth factor (FGF), transforming growth factor-β1, and the like. In certain embodiments, the umbilical cord biomaterial comprises growth factors such as FGF, b-FGF, EGF, IGF-1, PDGF and TGF-β. The composition of the umbilical cord biomaterial may thus be ideally suited to encourage the migration of fibroblasts and macrophages, and thus, e.g., the promotion of wound healing.

In one embodiment, the invention provides an umbilical cord biomaterial wherein at least 50% of the dry weight of the biomaterial is collagen I. In various more specific embodiments, at least 55%, 60%, 65% or 70% of the dry weight of the biomaterial is collagen I. In another specific embodiment, the invention provides an umbilical cord biomaterial wherein at most 5% of the dry weight of the biomaterial is collagen III. In various more specific embodiments, at most 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0% or 2.9% of the dry weight of the biomaterial is collagen III. In another specific embodiment, the invention provides an umbilical cord biomaterial wherein at least 4% of the dry weight of the biomaterial is collagen IV. In various more specific embodiments, at least 5%, 6%, 7%, 8%, 9%, 10% or 11% of the dry weight of said biomaterial is collagen IV. In another specific embodiment, the invention provides an umbilical cord biomaterial wherein at most 4% of the dry weight of the biomaterial is elastin. In various more specific embodiments, at most 3.8%, 3.6%, 3.4%, 3.2%, 3.0%, 2.8%, 2.6%, 2.4%, 2.2%, 2.0%, or 1.8% of the dry weight of the biomaterial is elastin. In another specific embodiment, at least 4% of the dry weight of the biomaterial is glycosaminoglycan. In various more specific embodiments, at least 4.1%, 4.2%, 4.3%, 4.4%, 4.5% or 4.6% of the dry weight of said biomaterial is glycosaminoglycan.

The umbilical cord biomaterial may be used in a single-layered format, for example, as a single-layer sheet or an un-laminated membrane. Alternatively, the umbilical cord biomaterial may be used in a double-layer or multiple-layer format, e.g., the umbilical cord biomaterial may be laminated. Lamination can provide greater stiffness and durability, for example, during the healing process. The umbilical cord biomaterial may be, for example, laminated as described below (see Section 5.1.7).

The umbilical cord biomaterial may further comprise collagen from a non-umbilical cord source. For example, one or more layers of umbilical cord biomaterial may comprise, e.g., be coated or impregnated with, or layered with, purified extracted collagen. Such collagen may be obtained, for example, from commercial sources, or may be produced according to known methods, such as those disclosed in U.S. Pat. Nos. 4,420,339, 5,814,328, and 5,436,135, the disclosures of which are hereby incorporated by reference. Such collagen can also be obtained from a placental source, including a placenta obtained from the same donor as the umbilical cord biomaterial.

The umbilical cord biomaterial can comprise one or more compounds or substances that are not present in the umbilical cord material from which the biomaterial is derived. Moreover, the umbilical cord biomaterial can comprise non-naturally-occurring amounts of one or more compounds or substances that are normally present in the umbilical cord from which the biomaterial is derived. For example, the umbilical cord biomaterial can comprise, e.g., can be impregnated with, a bioactive compound, such as those listed in Section 5.1.2, below. Such bioactive compounds include, but are not limited to, small organic molecules (e.g., drugs), antibiotics (such as, for example, Clindamycin, Minocycline, Doxycycline, Gentamycin), hormones, growth factors, anti-tumor agents, anti-fungal agents, anti-viral agents, pain medications, anti-histamines, anti-inflammatory agents, anti-infectives including but not limited to silver (such as silver salts, including but not limited to silver nitrate and silver sulfadiazine), elemental silver, antibiotics, bactericidal enzymes (such as lysozyme), wound healing agents (such as cytokines including but not limited to PDGF, TGF; thymosin), hyaluronic acid as a wound healing agent, wound sealants (such as fibrin with or without thrombin), cellular attractant and scaffolding reagents (such as added fibronectin) and the like. In a specific example, the umbilical cord biomaterial may be impregnated with at least one growth factor, for example, fibroblast growth factor, epithelial growth factor, etc. The biomaterial may also be impregnated with small organic molecules such as specific inhibitors of particular biochemical processes e.g., membrane receptor inhibitors, kinase inhibitors, growth inhibitors, anticancer drugs, antibiotics, etc. Impregnating the umbilical cord biomaterial with a bioactive compound may be accomplished, e.g., by immersing the biomaterial in a solution of the bioactive compound of the desired concentration for a time sufficient to allow the biomaterial to absorb and to equilibrate with the solution. In a specific embodiment, the biomaterial so impregnated is a dried biomaterial, and the solution partially or fully re-hydrates the biomaterial, compared to an umbilical cord or umbilical cord membrane in vivo. In another embodiment, the biomaterial is impregnated prior to drying the biomaterial, e.g., to substantial dryness.

In other embodiments, the umbilical cord biomaterial may be combined with a hydrogel to form a composite. The use of any hydrogel composition known to one skilled in the art is encompassed within the invention, e.g., any of the hydrogel compositions disclosed in the following reviews: Graham, 1998, *Med. Device Technol.* 9(1): 18-22; Peppas et al., 2000, *Eur. J. Pharm. Biopharm.* 50(1): 27-46; Nguyen et al., 2002, *Biomaterials*, 23(22): 4307-14; Henincl et al., 2002*Adv. Drug Deliv. Rev* 54(1): 13-36; Skelhorne et al., 2002, *Med. Device. Technol.* 13(9): 19-23; Schmedlen et al., 2002, *Biomaterials* 23: 4325-32. In a specific embodiment, the hydrogel composition is applied on the umbilical cord biomaterial, that is, is disposed on the surface of the biomaterial. The hydrogel composition for example, may be sprayed onto the umbilical cord biomaterial or coated onto the surface of the biomaterial, or the biomaterial may, for example, be soaked, bathed or saturated with the hydrogel composition. In another specific embodiment, the hydrogel is sandwiched between two or more layers of umbilical cord biomaterial. In an even more specific embodiment, the hydrogel is sandwiched between two layers of umbilical cord biomaterial, wherein the edges of the two layers of biomaterial are sealed so as to substantially or completely contain the hydrogel.

The hydrogels useful in the methods and compositions of the invention can be made from any water-interactive, or water soluble polymer known in the art, including but not limited to, polyvinylalcohol (PVA), polyhydroxyehthyl methacrylate, polyethylene glycol, polyvinyl pyrrolidone, hyaluronic acid, alginate, collagen, gelatin, dextran or derivatives and analogs thereof.

In some embodiments, a composition comprises an umbilical cord biomaterial of the invention, one or more bioactive compounds and a hydrogel. In other embodiments, a composition comprises an umbilical cord biomaterial and a hydrogel composition that comprises one or more bioactive compounds. In yet another embodiment, a composition comprises an umbilical cord biomaterial comprising one or more bioactive compounds and a hydrogel composition comprising one or more bioactive compounds. The bioactive compounds can be, for example, one or more compounds as described in Section 5.1.2, below.

5.1.2 Bioactive Compounds

The umbilical cord biomaterial of the invention can comprise (e.g., be impregnated with or coated with) one or more bioactive or medicinal compounds, such as small organic molecules (e.g., drugs), antibiotics, antiviral agents, antimicrobial agents, anti-inflammatory agents, antiproliferative agents, cytokines, enzyme or protein inhibitors, antihistamines, and the like. In various embodiments, the umbilical cord biomaterial may be coated or impregnated with antibiotics (such as Clindamycin, Minocycline, Doxycycline, Gentamycin), hormones, growth factors, anti-tumor agents, antifungal agents, anti-viral agents, pain medications (including XYLOCAINE®, Lidocaine, Procaine, Novocaine, etc.), antihistamines (e.g., diphenhydramine, BENADRYL®, etc.), anti-inflammatory agents, anti-infectives including but not limited to silver (such as silver salts, including but not limited to silver nitrate and silver sulfadiazine), elemental silver, antibiotics, bactericidal enzymes (such as lysozome), wound healing agents (such as cytokines including but not limited to PDGF (e.g., REGRANEX®), TGF; thymosin), hyaluronic acid as a wound healing agent, wound sealants (such as fibrin with or without thrombin), cellular attractant and scaffolding reagents (such as fibronectin), and the like, or combinations of any of the foregoing, or of the foregoing and other compounds not listed. Such impregnation or coating may be accomplished by any means known in the art, and a portion or the whole of the umbilical cord biomaterial may be so coated or impregnated.

The umbilical cord biomaterial, or composites comprising umbilical cord biomaterial, may comprise any of the compounds listed herein, without limitation, individually or in any combination. Any of the biologically active compounds listed herein may be formulated by known methods for immediate release or extended release. Additionally, the umbilical cord biomaterial may comprise two or more biologically active compounds in different manners; e.g., the biomaterial may be impregnated with one biologically active compound and coated with another. In another embodiment, the umbilical cord biomaterial comprises one biologically active compound formulated for extended release, and a second biologically active compound formulated for immediate release.

Wound healing requires adequate nutrition, particularly the presence of iron, zinc, vitamin C, arginine, and the like. Thus, the umbilical cord biomaterial may comprise, e.g., be impregnated or coated with, a physiologically-available form of one or more nutrients required for wound healing. Preferably, the nutrient is formulated for extended release.

The umbilical cord biomaterial, or composite comprising umbilical cord biomaterial, may comprise an antibiotic. In certain embodiments, the antibiotic is a macrolide (e.g., tobramycin (TOBI®)), a cephalosporin (e.g., cephalexin (KEFLEX®)), cephradine (VELOSEF®)), cefuroxime (CEFTIN®, cefprozil (CEFZIL®), cefaclor (CECLOR®), cefixime (SUPRAX® or cefadroxil (DURICEF®), a clarithromycin (e.g., clarithromycin (Biaxin)), an erythromycin (e.g., erythromycin (EMYCIN®)), a penicillin (e.g., penicillin V (V-CILLINK® or PEN VEEK®)) or a quinolone (e.g., ofloxacin (FLOXIN®), ciprofloxacin (CIPRO®) ornorfloxacin (NOROXIN®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The umbilical cord biomaterial, or a composite comprising umbilical cord biomaterial, may comprise, e.g., be coated or impregnated with, an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

The umbilical cord biomaterial, or a composite comprising umbilical cord biomaterial, may comprise, e.g., be coated or impregnated with, an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, methotrexate, colchicine, allopurinol, probenecid, sulfinpyrazone and benzbromarone.

The umbilical cord biomaterial, or a composite comprising umbilical cord biomaterial, may comprise, e.g., be coated or impregnated with, an antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons.

The umbilical cord biomaterial, or a composite comprising umbilical cord biomaterial, comprises, e.g., may be coated or impregnated with, a cytokine receptor modulator. Examples of cytokine receptor modulators include, but are not limited to, soluble cytokine receptors (e.g., the extracellular domain of a TNF-α receptor or a fragment thereof, the extracellular domain of an IL-10 receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-10 antibodies, anti-IL-6 antibodies, anti-IL-8 antibodies (e.g., ABX-IL-8 (Abgenix)), and anti-IL-12 antibodies). In a specific embodiment, a cytokine receptor modulator is IL-4, IL-10, or a fragment thereof. In another embodiment, a cytokine receptor modulator is an anti-IL-1 antibody, anti-IL-6 antibody, anti-IL-12 receptor antibody, or anti-TNF-α antibody. In another embodiment, a cytokine receptor modulator is the extracellular domain of a TNF-α receptor or a fragment thereof. In certain embodiments, a cytokine receptor modulator is not a TNF-α antagonist.

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as immunomodulatory agents are human or humanized.

The umbilical cord biomaterial, or a composite comprising umbilical cord biomaterial, may also comprise, e.g., be coated or impregnated with a cytokine. Examples of cytokines include, but are not limited to, colony stimulating factor 1 (CSF-1), interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), insulin-like growth factor 1 (IGF-1), platelet derived growth factor (PDGF), erythropoietin (Epo), epidermal growth factor (EGF), fibroblast growth factor (FGF) (basic or acidic), granulocyte macrophage stimulating factor (GM-CSF), granulocyte colony stimulating factor (G-CSF), heparin binding epidermal growth factor (HEGF), macrophage colony stimulating factor (M-CSF), prolactin, and interferon (IFN), e.g., IFN-alpha, and IFN-gamma), transforming growth factor alpha (TGF-α), TGFβ1, TGFβ2, tumor necrosis factor alpha (TNF-α), vascular endothelial growth factor (VEGF), hepatocyte growth factor (HGF), etc.

The umbilical cord biomaterial may also comprise, e.g., be coated or impregnated with, a hormone. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins. Examples of β-interferons include, but are not limited to, interferon β1-a and interferon β1-b.

The umbilical cord biomaterial, or composite comprising umbilical cord biomaterial, may also comprise, e.g., be coated or impregnated with, an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The umbilical cord biomaterial, or a composite comprising umbilical cord biomaterial, may also comprise, e.g., be coated or impregnated with, an immunomodulatory agent, including but not limited to methothrexate, leflunomide, cyclophosphamide, cyclosporine A, macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. In particular, immunomodulatory agents include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. Examples of T cell receptor modulators include, but are not limited to, anti-T cell receptor antibodies (e.g., anti-CD4 antibodies (e.g., cM-T412 (Boehringer), IDEC-CE9.Is (IDEC and SKB), mAb 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131(IDEC)), anti-CD52 antibodies (e.g., CAMPATH 1H (Ilex)), anti-CD2 antibodies, anti-CD1 1a antibodies (e.g., Xanelim (Genentech)), and anti-B7 antibodies (e.g., IDEC-114) (IDEC))) and CTLA4-immunoglobulin. In a specific embodiment, a T cell receptor modulator is a CD2 antagonist. In other embodiments, a T cell receptor modulator is not a CD2 antagonist. In another specific embodiment, a T cell receptor modulator is a CD2 binding molecule, preferably MEDI-507. In other embodiments, a T cell receptor modulator is not a CD2 binding molecule.

The umbilical cord biomaterial, or composite comprising umbilical cord biomaterial, may also comprise, e.g., be coated or impregnated with a class of immunomodulatory compounds known as IMIDS®. As used herein and unless otherwise indicated, the term "IMID®" and "IMIDS®" (Celgene Corporation) encompasses small organic molecules that markedly inhibit TNF-α, LPS induced monocyte IL-1β and IL-12, and partially inhibit IL-6 production. Specific immunomodulatory compounds are discussed below.

Specific examples of such immunomodulatory compounds, include, but are not limited to, cyano and carboxy derivatives of substituted styrenes such as those disclosed in U.S. Pat. No. 5,929,117; 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), including, but not limited to, those disclosed in U.S. Pat. Nos. 5,635,517, 6,476,052, 6,555,554, and 6,403,613; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; and isoindole-imide compounds such as those described in U.S. patent application Ser. No. 09/972,487 filed on Oct. 5, 2001, U.S. patent application Ser. No. 10/032,286 filed on Dec. 21, 2001, and International Application No. PCT/US01/50401 (International Publication No. WO 02/059106). The entireties of each of the patents and patent applications identified herein are incorporated herein by reference. Immunomodulatory compounds do not include thalidomide.

Other specific immunomodulatory compounds include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein by reference. These compounds have the structure I:

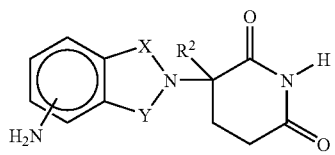

in which one of X and Y is C=O, the other of X and Y is C=O or $CH_2$, and $R^2$ is hydrogen or lower alkyl, in particular methyl. Specific immunomodulatory compounds include, but are not limited to:

1-oxo-2-(2,6-dioxopiperidin-3-yl)-4-aminoisoindoline;
1-oxo-2-(2,6-dioxopiperidin-3-yl)-5-aminoisoindoline;
1-oxo-2-(2,6-dioxopiperidin-3-yl)-6-aminoisoindoline;
1-oxo-2-(2,6-dioxopiperidin-3-yl)-7-aminoisoindoline;
1,3-dioxo-2-(2,6-dioxopiperidin-3-yl)-4-aminoisoindoline; and
1,3-dioxo-2-(2,6-dioxopiperidin-3-yl)-5-aminoisoindoline.

Other specific immunomodulatory compounds belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

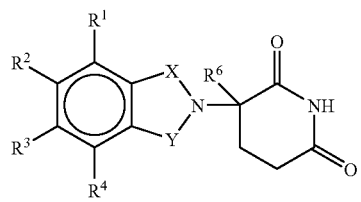

in which:
one of X and Y is C=O and the other of X and Y is C=O or $CH_2$;

(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;

$R^5$ is hydrogen or alkyl of 1 to 8 carbon atoms;

$R^6$ is hydrogen, alkyl of 1 to 8 carbon atoms, benzyl, or halo;

provided that $R^6$ is other than hydrogen if X and Y are C=O and (i) each of $R^1$, $R^2$, $R^3$, and $R^4$ is fluoro or (ii) one of $R^1$, $R^2$, $R^3$, or $R^4$ is amino.

Compounds representative of this class are of the formulas:

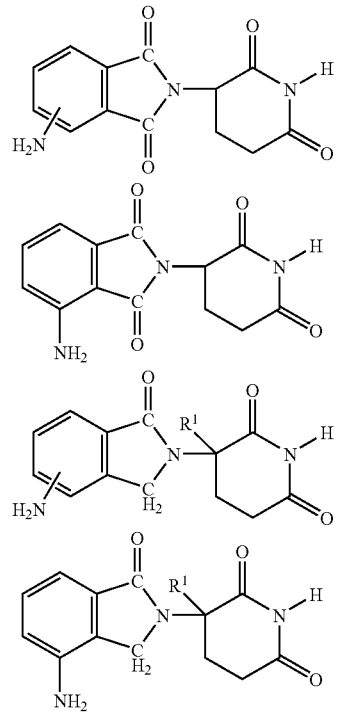

wherein $R^1$ is hydrogen or methyl. In a separate embodiment, the invention encompasses the use of enantiomerically pure forms (e.g., optically pure (R) or (S) enantiomers) of these compounds.

Still other specific immunomodulatory compounds belong to a class of isoindole-imides disclosed in U.S. Patent Application Publication Nos. US 2003/0096841 and US 2003/0045552, and International Application No. PCT/US01/50401 (International Publication No. WO 02/059106), each of which are incorporated herein by reference. Representative compounds are of formula II:

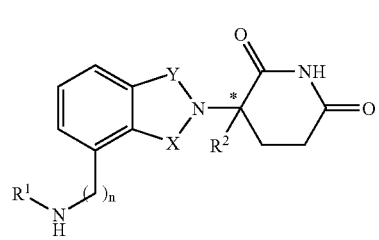

and pharmaceutically acceptable salts, hydrates, solvates, clathrates, enantiomers, diastereomers, racemates, and mixtures of stereoisomers thereof, wherein:

one of X and Y is C=O and the other is CH$_2$ or C=O;

R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$) alkyl-C(O)OR$^5$, C(O)NHR$^3$, C(S)NHR$^3$, C(O)NR$^3$R$^{3'}$, C(S) NR$^3$R$^{3'}$ or (C$_1$-C$_8$)alkyl-O(CO)R$^5$;

R$^2$ is H, F, benzyl, (C$_1$-C$_8$)alkyl, (C$_2$-C$_8$)alkenyl, or (C$_2$-C$_8$)alkynyl;

R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-C$_1$-C$_6$)heterocycloalkyl, (C$_0$-C$_4$)alkyl-C$_2$-C$_5$)heteroaryl, (C$_0$-C$_8$)alkyl-N(R$^6$)$_2$, (C$_1$-C$_8$)alkyl-OR$^5$, (C$_1$-C$_8$) alkyl-C(O)OR$^5$, (C$_1$-C$_8$)alkyl-O(CO)R$^5$, or C(O)OR$^5$;

R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-C$_2$-C$_5$)heteroaryl;

R$^5$ is (C$_1$-C$_8$)alkyl, (C$_2$-C$_8$)alkenyl, (C$_2$-C$_8$)alkynyl, benzyl, aryl, or (C$_2$-C$_5$)heteroaryl;

each occurrence of R$^6$ is independently H, (C$_1$-C$_8$)alkyl, (C$_2$-C$_8$)alkenyl, (C$_2$-C$_8$)alkynyl, benzyl, aryl, (C$_2$-C$_5$)heteroaryl, or (C$_0$-C$_8$)alkyl-C(O)O—R$^5$ or the R$^6$ groups can join to form a heterocycloalkyl group;

n is 0 or 1; and

* represents a chiral-carbon center.

In specific compounds of formula II, when n is 0 then R$^1$ is (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(S)NHR$^3$, or (C$_1$-C$_8$)alkyl-O(CO)R$^5$;

R$^2$ is H or (C$_1$-C$_8$)alkyl; and

R$^3$ is (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-C$_2$-C$_5$)heteroaryl, (C$_5$-C$_8$)alkyl-N (R$^6$)$_2$; (C$_0$-C$_8$)alkyl-NH—C(O)O—R$^5$; (C$_1$-C$_8$)alkyl-OR$^5$, (C$_1$-C$_8$)alkyl-C(O)OR$^5$, (C$_1$-C$_8$)alkyl-O(CO)R$^5$, or C(O) OR$^5$; and the other variables have the same definitions.

In other specific compounds of formula II, R$^2$ is H or (C$_1$-C$_4$)alkyl.

In other specific compounds of formula II, R$^1$ is (C$_1$-C$_8$) alkyl or benzyl.

In other specific compounds of formula II, R$^1$ is H, (C$_1$-C$_8$)alkyl, benzyl, CH$_2$OCH$_3$, CH$_2$CH$_2$OCH$_3$, or

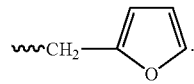

In another embodiment of the compounds of formula II, R$^1$ is

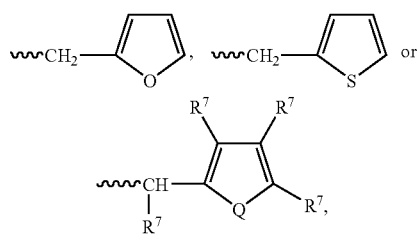

wherein Q is O or S, and each occurrence of R$^7$ is independently H, (C$_1$-C$_8$)alkyl, (C$_3$-C$_7$)cycloalkyl, (C$_2$-C$_8$)alkenyl, (C$_2$-C$_8$)alkynyl, benzyl, aryl, halogen, (C$_0$-C$_4$)alkyl-(C$_1$-C$_6$) heterocycloalkyl, (C$_0$-C$_4$)alkyl-(C$_2$-C$_5$)heteroaryl, (C$_0$-C$_8$) alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$, or adjacent occurrences of R$^7$ can be taken together to form a bicyclic alkyl or aryl ring.

In other specific compounds of formula II, R$^1$ is C(O)R$^3$.

In other specific compounds of formula II, R$^3$ is (C$_0$-C$_4$) alkyl-C$_2$-C$_5$)heteroaryl, (C$_1$-C$_8$)alkyl, aryl, or (C$_0$-C$_4$)alkyl-OR$^5$.

In other specific compounds of formula II, heteroaryl is pyridyl, furyl, or thienyl.

In other specific compounds of formula II, R$^1$ is C(O)OR$^4$.

In other specific compounds of formula II, the H of C(O) NHC(O) can be replaced with (C$_1$-C$_4$)alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl))-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2, 6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl) methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1, 3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl] methyl}(octylamino)carboxamide; and N-{[2-(2,6-dioxo(3-piperidyl))-1,3-dioxoisoindolin-4-yl]methyl}(benzylamino) carboxamide.

Still other specific immunomodulatory compounds belong to a class of isoindole-imides disclosed in U.S. Patent Application Publication Nos. US 2002/0045643, International Publication No. WO 98/54170, and U.S. Pat. No. 6,395,754, each of which is incorporated herein by reference. Representative compounds are of formula III:

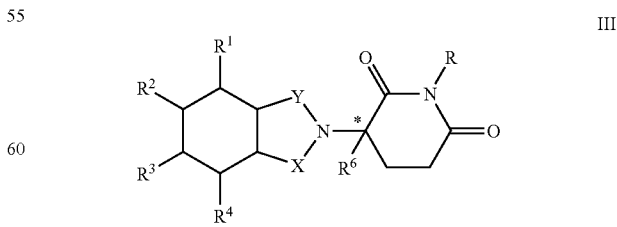

and pharmaceutically acceptable salts, hydrates, solvates, clathrates, enantiomers, diastereomers, racemates, and mixtures of stereoisomers thereof, wherein:

one of X and Y is C=O and the other is CH₂ or C=O;

R is H or CH₂OCOR';

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —NHR⁵ and the remaining of $R^1$, $R^2$, $R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7$—$CHR^{10}$—$N(R^8R^9)$;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —CH₂CH₂X₁CH₂CH₂— in which $X_1$ is —O—, —S—, or —NH—;

$R^{10}$ is hydrogen, alkyl of to 8 carbon atoms, or phenyl; and

* represents a chiral-carbon center.

Other representative compounds are of formula:

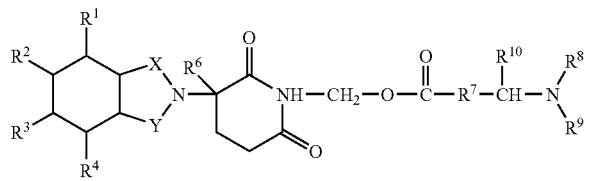

wherein:

one of X and Y is C=O and the other of X and Y is C=O or CH₂;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, and $R^4$ is —NHR⁵ and the remaining of $R^1$, $R^2$, $R^3$, and $R^4$ are hydrogen;

$R^5$ is hydrogen or alkyl of 1 to 8 carbon atoms;

$R^6$ is hydrogen, alkyl of 1 to 8 carbon atoms, benzo, chloro, or fluoro;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —CH₂CH₂X¹CH₂CH₂— in which $X^1$ is —O—, —S—, or —NH—;

$R^{10}$ is hydrogen, alkyl of to 8 carbon atoms, or phenyl.

Other representative compounds are of formula:

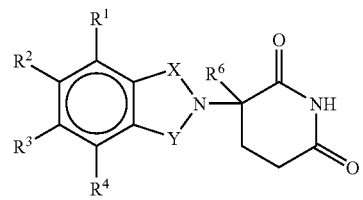

in which:

one of X and Y is C=O and the other of X and Y is C=O or CH₂;

each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is nitro or protected amino and the remaining of $R^1$, $R^2$, $R^3$, and $R^4$ are hydrogen; and $R^6$ is hydrogen, alkyl of 1 to 8 carbon atoms, benzo, chloro, or fluoro.

Other representative compounds are of formula:

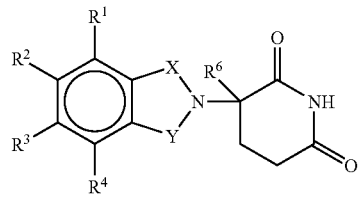

in which:

one of X and Y is C=O and the other of X and Y is C=O or CH₂; (i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —NHR⁵ and the remaining of $R^1$, $R^2$, $R^3$, and $R^4$ are hydrogen;

$R^5$ is hydrogen, alkyl of 1 to 8 carbon atoms, or CO—$R^7$—$CH(R^{10})NR^8R^9$ in which each of $R^7$, $R^8$, $R^9$, and $R^{10}$ is as herein defined; and $R^6$ is alkyl of 1 to 8 carbon atoms, benzo, chloro, or fluoro.

Specific examples of the compounds are of formula:

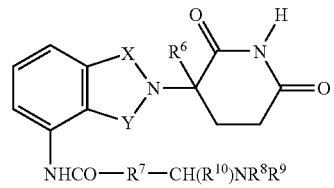

in which:

one of X and Y is C=O and the other of X and Y is C=O or CH₂;

$R^6$ is hydrogen, alkyl of 1 to 8 carbon atoms, benzyl, chloro, or fluoro;

$R^7$ is m-phenylene, p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —CH₂CH₂X¹CH₂CH₂— in which $X^1$ is —O—, —S— or —NH—; and $R^{10}$ is hydrogen, alkyl of 1 to 8 carbon atoms, or phenyl.

Preferred immunomodulatory compounds are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Warren, N.J. 4-(Amino)-2-(2,6-dioxo(3-piperidyl))-isoindoline-1,3-dione has the following chemical structure:

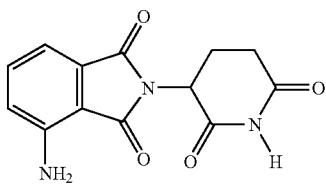

The compound 3-(4-amino-1-oxo-1,3-dihydro-isoindol-2-yl)-piperidine-2,6-dione has the following chemical structure:

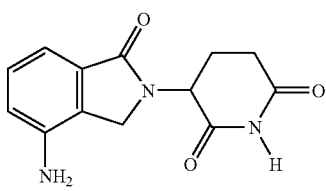

In another embodiment, specific immunomodulatory compounds encompass polymorphic forms of 3-(4-amino-1-oxo-1,3 dihydro-isoindol-2-yl)-piperidene-2,6-dione such as Form A, B, C, D, E, F, G and H, disclosed in U.S. provisional application no. 60/499,723 filed on Sep. 4, 2003, and U.S. non-provisional application Ser. No. 10/934,863, filed Sep. 3, 2004, both of which are incorporated herein by reference. For example, Form A of 3-(4-amino-1-oxo-1,3 dihydro-isoindol-2-yl)-piperidene-2,6-dione is an unsolvated, crystalline material that can be obtained from non-aqueous solvent systems. Form A has an X-ray powder diffraction pattern comprising significant peaks at approximately 8, 14.5, 16, 17.5, 20.5, 24 and 26 degrees 2θ, and has a differential scanning calorimetry melting temperature maximum of about 270° C. Form A is weakly or not hygroscopic and appears to be the most thermodynamically stable anhydrous polymorph of 3-(4-amino-1-oxo-1,3 dihydro-isoindol-2-yl)-piperidine-2,6-dione discovered thus far.

Form B of 3-(4-amino-1-oxo-1,3 dihydro-isoindol-2-yl)-piperidene-2,6-dione is a hemihydrated, crystalline material that can be obtained from various solvent systems, including, but not limited to, hexane, toluene, and water. Form B has an X-ray powder diffraction pattern comprising significant peaks at approximately 16, 18, 22 and 27 degrees 2θ, and has endotherms from DSC curve of about 146 and 268° C., which are identified dehydration and melting by hot stage microscopy experiments. Interconversion studies show that Form B converts to Form E in aqueous solvent systems, and converts to other forms in acetone and other anhydrous systems.

Form C of 3-(4-amino-1-oxo-1,3-dihydro-isoindol-2-yl)-piperidene-2,6-dione is a hemisolvated crystalline material that can be obtained from solvents such as, but not limited to, acetone. Form C has an X-ray powder diffraction pattern comprising significant peaks at approximately 15.5 and 25 degrees 2θ, and has a differential scanning calorimetry melting temperature maximum of about 269° C. Form C is not hygroscopic below about 85% RH, but can convert to Form B at higher relative humidities.

Form D of 3-(4-amino-1-oxo-1,3-dihydro-isoindol-2-yl)-piperidene-2,6-dione is a crystalline, solvated polymorph prepared from a mixture of acetonitrile and water. Form D has an X-ray powder diffraction pattern comprising significant peaks at approximately 27 and 28 degrees 2θ, and has a differential scanning calorimetry melting temperature maximum of about 270° C. Form D is either weakly or not hygroscopic, but will typically convert to Form B when stressed at higher relative humidities.

Form E of 3-(4-amino-1-oxo-1,3 dihydro-isoindol-2-yl)-piperidene-2,6-dione is a dihydrated, crystalline material that can be obtained by slurrying 3-(4-amino-1-oxo-1,3 dihydro-isoindol-2-yl)-piperidene-2,6-dione in water and by a slow evaporation of 3-(4-amino-1-oxo-1,3 dihydro-isoindol-2-yl)-piperidene-2,6-dione in a solvent system with a ratio of about 9:1 acetone:water. Form E has an X-ray powder diffraction pattern comprising significant peaks at approximately 20, 24.5 and 29 degrees 2θ, and has a differential scanning calorimetry melting temperature maximum of about 269° C. Form E can convert to Form C in an acetone solvent system and to Form G in a THF solvent system. In aqueous solvent systems, Form E appears to be the most stable form. Desolvation experiments performed on Form E show that upon heating at about 125° C. for about five minutes, Form E can convert to Form B. Upon heating at 175° C. for about five minutes, Form B can convert to Form F.

Form F of 3-(4-amino-1-oxo-1,3 dihydro-isoindol-2-yl)-piperidene-2,6-dione is an unsolvated, crystalline material that can be obtained from the dehydration of Form E. Form F has an X-ray powder diffraction pattern comprising significant peaks at approximately 19, 19.5 and 25 degrees 2θ, and has a differential scanning calorimetry melting temperature maximum of about 269° C.

Form G of 3-(4-amino-1-oxo-1,3 dihydro-isoindol-2-yl)-piperidene-2,6-dione is an unsolvated, crystalline material that can be obtained from slurrying forms B and E in a solvent such as, but not limited to, tetrahydrofuran (THF). Form G has an X-ray powder diffraction pattern comprising significant peaks at approximately 21, 23 and 24.5 degrees 2θ, and has a differential scanning calorimetry melting temperature maximum of about 267° C.

Form H of 3-(4-amino-1-oxo-1,3 dihydro-isoindol-2-yl)-piperidene-2,6-dione is a partially hydrated (about 0.25 moles) crystalline material that can be obtained by exposing Form E to 0% relative humidity. Form H has an X-ray powder diffraction pattern comprising significant peaks at approximately 15, 26 and 31 degrees 2θ, and has a differential scanning calorimetry melting temperature maximum of about 269° C.

Other specific immunomodulatory compounds include, but are not limited to, 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

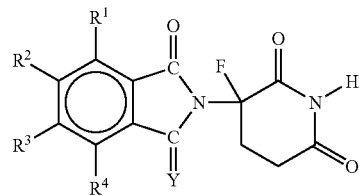

wherein Y is oxygen or $H_2$ and
each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds include, but are not limited to, the tetra substituted 2-(2,6-dioxopiperidin-3-yl)-1-oxoisoindolines described in U.S. Pat. No. 5,798,368, which is incorporated herein by reference. Representative compounds are of formula:

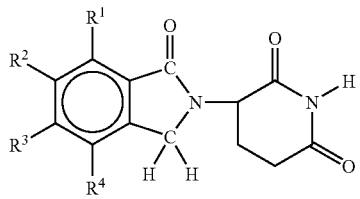

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds include, but are not limited to, 1-oxo and 1,3-dioxo-2-(2,6-dioxopiperidin-3-yl) isoindolines disclosed in U.S. Pat. No. 6,403,613, which is incorporated herein by reference. Representative compounds are of formula:

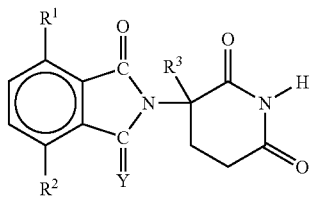

in which

Y is oxygen or $H_2$, a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and $R^3$ is hydrogen, alkyl, or benzyl.

Specific examples of the compounds are of formula:

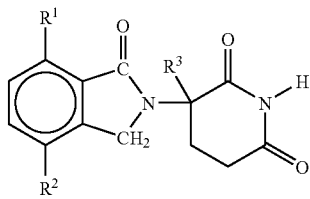

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and $R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

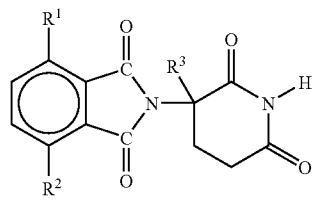

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and $R^3$ is hydrogen, alkyl of from 1 to 4 carbon atoms, or benzyl.

Specific examples include, but are not limited to, 1-oxo-2-(2,6-dioxopiperidin-3-yl)-4-methylisoindoline.

Other specific immunomodulatory compounds include, but are not limited to, 1-oxo and 1,3-dioxoisoindolines substituted in the 4- or 5-position of the indoline ring described in U.S. Pat. No. 6,380,239 and co-pending U.S. application Ser. No. 10/900,270, filed Jul. 28, 2004, which are incorporated herein by reference. Representative compounds are of formula:

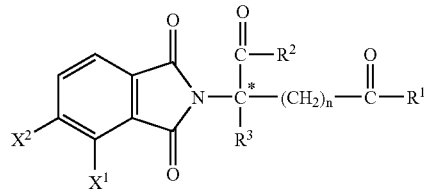

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

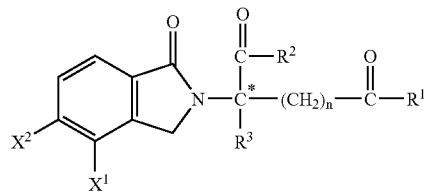

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-cabamoyl-butyric acid, which have the following structures, respectively, and pharmaceutically acceptable salts, solvates, prodrugs, and stereoisomers thereof:

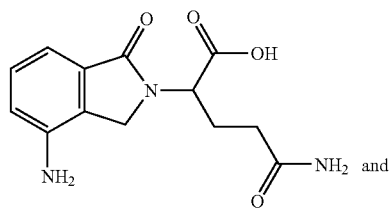
and

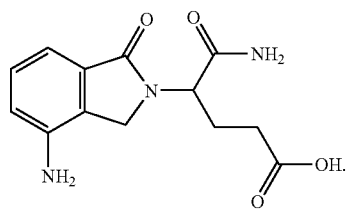

Other representative compounds are of formula:

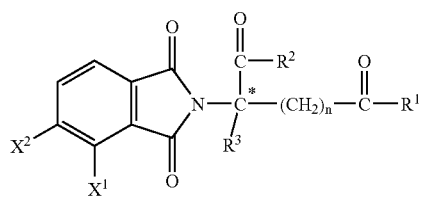

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

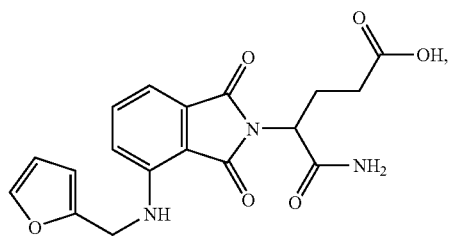

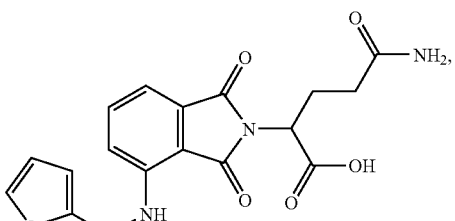

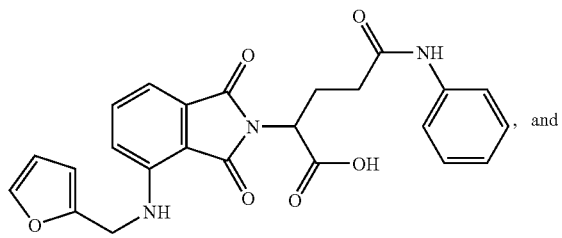
, and

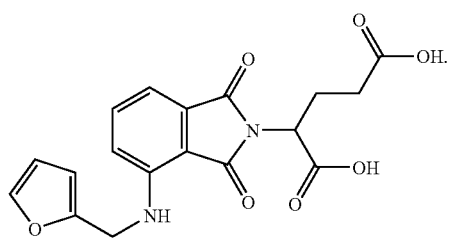

Other specific examples of the compounds are of formula:

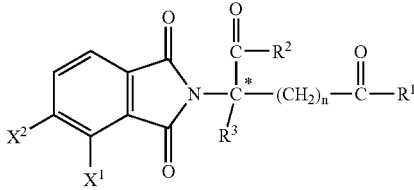

wherein one of $X^1$ and $X^2$ is nitro, or NH—Z, and the other of $X^1$ or $X^2$ is hydrogen;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2;

provided that if one of $X^1$ and $X^2$ is nitro, and n is 1 or 2, then $R^1$ and $R^2$ are other than hydroxy; and if —$COR^2$ and —$(CH_2)_nCOR^1$ are different, the carbon atom designated C* constitutes a center of chirality. Other representative compounds are of formula:

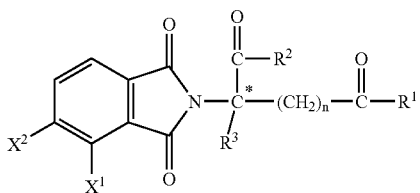

wherein one of $X^1$ and $X^2$ is alkyl of one to six carbons;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —$COR^2$ and —$(CH_2)_nCOR^1$ are different, the carbon atom designated C* constitutes a center of chirality.

Still other specific immunomodulatory compounds include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

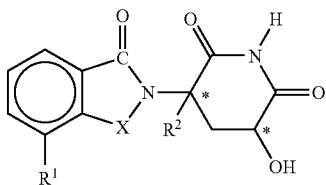

wherein:
the carbon atoms designated * constitute centers of chirality;
X is —C(O)— or —$CH_2$—;
$R^1$ is alkyl of 1 to 8 carbon atoms or —$NHR^3$;
$R^2$ is hydrogen, alkyl of 1 to 8 carbon atoms, or halogen; and
$R^3$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms,
benzyl, unsubstituted or substituted with alkyl of 1 to 8 carbon atoms, alkoxy of 1 to 8 carbon atoms, halo, amino, or alkylamino of 1 to 4 carbon atoms, or —$COR^4$ in which
$R^4$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms, or
benzyl, unsubstituted or substituted with alkyl of 1 to 8 carbon atoms, alkoxy of 1 to 8 carbon atoms, halo, amino, or alkylamino of 1 to 4 carbon atoms.

The immunomodulatory compounds disclosed herein can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein, and unless otherwise specified, the term "solvate" means a compound of the present invention or a salt thereof, that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the invention that comprise —NO, —$NO_2$, —ONO, or —$ONO_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elsevier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

As used herein, and unless otherwise specified, the term "stereoisomer" encompasses all enantiomerically/stereomerically pure and enantiomerically/stereomerically enriched compounds of this invention.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer. In certain cases, a compound of the invention is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds of this invention (e.g., R/S=30/70, 35/65, 40/60, 45/55, 55/45, 60/40, 65/35 and 70/30). Various immunomodulatory compounds of the invention contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E.L. Eliel, Ed., Univ. of Notre Dame Press, Notre Dame, Ind., 1972).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The amount of the bioactive compound coating or impregnating the umbilical cord biomaterial may vary, and will preferably depend upon the particular bioactive compound to be delivered, and the effect desired. For example, where the bioactive compound is an anti-inflammatory agent, the amount of the anti-inflammatory agent on or contained by the umbilical cord biomaterial is an amount sufficient to measurably reduce one or more symptoms or indicia of inflammation in a tissue contacted by, or proximal to, e.g., an umbilical cord biomaterial implant.

In various embodiments, the umbilical cord biomaterial of the invention may comprise, e.g., be coated or impregnated with, at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 100, 1250, 1500, 2000, 2500, 300, 3500, 4000, 4500, 5000, 5500, 6000, 6500, 7000, 7500, 8000, 8500, 9000, 9500, 10000, 20000, 30000, 40000, 50000, 60000, 70000, 80000, 90000, 100000, 200000, 300000, 400000, 500000, 600000, 700000, 800000, 900000 or at least 1000000 nanograms of a bioactive compound. In another embodiment, the umbilical cord biomaterial of the invention may be coated with, or impregnated with, no more than 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 100, 1250, 1500, 2000, 2500, 300, 3500, 4000, 4500, 5000, 5500, 6000, 6500, 7000, 7500, 8000, 8500, 9000, 9500, 10000, 20000, 30000, 40000, 50000, 60000, 70000, 80000, 90000, 100000, 200000, 300000, 400000, 500000, 600000, 700000, 800000, 900000 or at least 1000000 nanograms of a bioactive compound.

5.1.3 Conformation of the Umbilical Cord Biomaterial

The umbilical cord biomaterial may be formed into any shape or conformation that will facilitate its use in the methods of the invention. For example, the umbilical cord biomaterial can be formed into any shape or conformation that will facilitate, e.g., the occlusion of a tympanic membrane perforation, particularly in the context of a tympanoplasty or myringoplasty; repair of a joint, ligament or tendon; etc. The umbilical cord biomaterial may, for example, be provided as an extended membrane, e.g., the entire membrane from a single umbilical cord. The umbilical cord biomaterial can also be provided as square, rectangular, circular or oval shaped pieces, or may be cut to conform generally to the shape of, e.g., a tympanic membrane, tendon, or other bodily structure. The umbilical cord biomaterial can be tubular. In various embodiments, umbilical cord biomaterial may be provided as pieces measuring approximately 1×1 cm, 1.5×1.5 cm, 2×2 cm, 2.5×2.5 cm, 1×1.5 cm, 1×2 cm, 1×2.5 cm, 1×3 cm, 1×3.5 cm, 1×4 cm, 1×4.5 cm, 1×5 cm, 1×5.5 cm, 1×6 cm, 1×6.5 cm, 1×7 cm, 1.5×2 cm, 1.5×2.5 cm, 1.5×3 cm, 1.5×3.5 cm, 1.5×4 cm, 1.5×4.5 cm, 1.5×5 cm, 1.5×5.5 cm, 1.5×6 cm, 1.5×6.5 cm, 1.5×7 cm, 2×2.5 cm, 2×3 cm, 2×3.5 cm, 2×4 cm, 2×4.5 cm, 2×5 cm, 2×5.5 cm, 2×6 cm, 2×6.5 cm, 2×7 cm, 2.5×2.5 cm, 2.5×3 cm, 2.5×3.5 cm, 2.5×4 cm, 2.5×4.5 cm, 2.5×5 cm, 2.5×5.5 cm, 2.5×6 cm, 2.5×6.5 cm, 2.5×7 cm, 3×3 cm, 3×3.5 cm, 3×4 cm, 3×4.5 cm, 3×5 cm, 3×5.5 cm, 3×6 cm, 3×6.5 cm, 3×7 cm, 3.5×3.5 cm, 3.5×4 cm, 3.5×4.5 cm, 3.5×5 cm, 3.5×5.5 cm, 3.5×6 cm, 3.5×6.5 cm, 3.5×7 cm, 4×2.5 cm, 4×4 cm, 4×4.5 cm, 4×5 cm, 4×5.5 cm, 4×6 cm, 4×6.5 cm, or 4×7 cm in size, or may be no smaller, or no larger, than 1×1 cm, 1.5×1.5 cm, 2×2 cm, 2.5×2.5 cm, 1×1.5 cm, 1×2 cm, 1×2.5 cm, 1×3 cm, 1×3.5 cm, 1×4 cm, 1×4.5 cm, 1×5 cm, 1×5.5 cm, 1×6 cm, 1×6.5 cm, 1×7 cm, 1.5×2 cm, 1.5×2.5 cm, 1.5×3 cm, 1.5×3.5 cm, 1.5×4 cm, 1.5×4.5 cm, 1.5×5 cm, 1.5×5.5 cm, 1.5×6 cm, 1.5×6.5 cm, 1.5×7 cm, 2×2.5 cm, 2×3 cm, 2×3.5 cm, 2×4 cm, 2×4.5 cm, 2×5 cm, 2×5.5 cm; 2×6 cm, 2×6.5 cm, 2×7 cm, 2.5×2.5 cm, 2.5×3 cm, 2.5×3.5 cm, 2.5×4 cm, 2.5×4.5 cm, 2.5×5 cm, 2.5×5.5 cm, 2.5×6 cm, 2.5×6.5 cm, 2.5×7 cm, 3×3 cm, 3×3.5 cm, 3×4 cm, 3×4.5 cm, 3×5 cm, 3×5.5 cm, 3×6 cm, 3×6.5 cm, 3×7 cm, 3.5×3.5 cm, 3.5×4 cm, 3.5×4.5 cm, 3.5×5 cm, 3.5×5.5 cm, 3.5×6 cm, 3.5×6.5 cm, 3.5×7 cm, 4×2.5 cm, 4×4 cm, 4×4.5 cm, 4×5 cm, 4×5.5 cm, 4×6 cm, 4×6.5 cm, or 4×7 cm, though the biomaterial may be cut to different dimensions. In preferred embodiments, wherein the umbilical cord biomaterial is used as a wound covering, the biomaterial is about 2.5 cm×2.5 cm to 3.5 cm×3.5 cm, or, more preferably, about 3×3 cm². Longer and/or wider pieces can be formed by laminating two or more smaller pieces, as described elsewhere herein. Further, the biomaterial may be provided as a sheet from which an end user may cut two or more pieces, or may be provided as a roll or strip.

The biomaterial may be provided to the end user either dry, or pre-wetted in a suitable physiologically-compatible, medically-useful liquid, such as a saline solution. In one embodiment, the solution comprises one or more bioactive compounds, as described in Section 5.1.2, above. Preferably, said bioactive compound is disposed onto or within the umbilical cord biomaterial such that the majority of the bioactive compound contacts the tympanic membrane at some point during the time the umbilical cord biomaterial contacts the tympanic membrane.

5.1.4 Methods of Making Umbilical Cord Biomaterial

The umbilical cord biomaterial of the invention can be made in a number of ways. For example, the biomaterial is preferably produced by any means that preserves the biochemical and structural characteristics of the membrane's components—chiefly collagen, elastin, laminin, and fibronectin. That is, the biomaterial can be made so as to preserve, or substantially preserve, the native structure of the protein components of the biomaterial. The biomaterial may also be altered, e.g., the proteins of the biomaterial can be crosslinked, so as to improve the strength (e.g., tensile strength) of the biomaterial. The biomaterial can be completely, or substantially completely, decellularized prior to use, that is, can comprise only, or substantially only, an umbilical cord outer membrane, or can be made to retain other components of the umbilical cord (e.g., Wharton's jelly, umbilical vessel(s), umbilical cord cells, and the like). Generally, an umbilical cord is separated from a placenta obtained by normal birth. The umbilical cord is then cleaned and disinfected, and optionally stored for further processing, e.g., decellularization and/or drying.

In one embodiment, the umbilical cord is separated from the placenta as soon as possible after delivery of the newborn. The umbilical cord may be used immediately, or may be stored for 2-5 days from the time of delivery prior to any further treatment. Preferably, the expectant mother is screened prior to the time of birth, using standard techniques known to one skilled in the art, for communicable diseases including but not limited to, HIV, HBV, HCV, HTLV, syphilis, CMV, and other viral pathogens known to contaminate umbilical cord tissue. One exemplary method for preparing the umbilical cord biomaterial of the invention comprises the following steps:

The umbilical cord is separated from the placental disc, and is typically massaged to remove umbilical cord blood. Optionally, the umbilical cord is sectioned into pieces of about 10 cm to about 15 cm in length. The umbilical cord or umbilical cord sections can then be stored for up to about 72 hours in a sterile, preferably buffered, saline solution, such as 0.9% sterile NaCl solution. Preferably, the umbilical cord is stored under refrigeration, at a temperature of about 1° C. to about 5° C.

At this time, the umbilical cord can be slit or cut longitudinally using, e.g., a scalpel and forceps, grooved director, or the like. This allows the umbilical cord membrane to be laid flat, allowing, e.g., removal of the Wharton's jelly, and/or one or more of the umbilical cord arteries, e.g., with a forceps. The umbilical cord membrane can also be processed further without cutting and opening the membrane. An umbilical cord vessel, for example, can be removed from the cord by grasping the vessels with a forceps and gently pulling and massaging until the vessel is removed, leaving the umbilical cord membrane as an intact tube. In a preferred embodiment of deveining, the umbilical vein of a fresh (less than 48 hours after delivery) umbilical cord is canalized using the blunt probe of a vein stripper. The blunt probe is replaced with a small bullet probe, and the vein is tied to the probe with thread. The stripper is then removed, and the process is repeated with the umbilical arteries.

The umbilical cord can be further processed "as is", wherein the cord comprises the umbilical cord membrane, vessels, and Wharton's jelly.

Continuing the embodiment, the umbilical cord biomaterial can be substantially decellularized; that is, substantially all cellular material and cellular debris (e.g., all visible cellular material and cellular debris) can removed from the biomaterial. Any decellularizing process known to one skilled in the art may be used, however, generally the process used for decellularizing the umbilical cord biomaterial of the invention does not disrupt the native conformation of the proteins making up the biomaterial. "Substantially decellularized," as used herein, means removal of at least 90% of the cells, more preferably at least 95% of the cells, and most preferably at least 99% of the cells associated with the umbilical cord membrane. Decellularization can leave cellular material on the umbilical cord biomaterial; for example, decellularization can leave nuclear material detectable by 4',6-diamidino-2-phenylindole (DAPI) and still be considered decellularized.

Decellularization can comprise physical scraping, for example, with a sterile cell scraper, in combination with rinsing with a sterile solution. The decellularization technique employed preferably does not result in gross disruption of the anatomy of the umbilical cord membrane or alter the biomechanical properties of the umbilical cord membrane.

The decellularization of the umbilical cord biomaterial can comprise contacting the membrane with a detergent-containing solution, such as one or more mild anionic or nonionic detergents, e.g., Triton X-100, sodium dodecyl sulfate, or the like, in an amount and for a time sufficient to decellularize the biomaterial. Any mild detergent, i.e., a non-caustic, low-foaming detergent, with a pH of about 6 to about 8, can be used to decellularize the umbilical cord biomaterial. In a specific embodiment, the biomaterial is contacted with about 0.01-1% deoxycholic acid (e.g., deoxycholic acid sodium salt monohydrate) for about 30 minutes to about 480 hours, preferably about 1 hour to about 240 hours, to decellularize the umbilical cord biomaterial. In a preferred embodiment, the umbilical cord biomaterial is decellularized in about 1% for about 20 days without scraping, followed by heat drying.

The biomaterial can be decellularized by any other method known to those in the art, including freezing to form intracellular ice (including, e.g., vapor phase freezing). Where freezing is used to decellularize the biomaterial, preferably a cryoprotectant is used, e.g., polyvinylpyrollidone at, e.g., 10% w/v, or dialyzed hydroxyethyl starch at, e.g., 10% w/v, added to standard cryopreservation solutions such as, in a non-limiting example, DMEM comprising 10% DMSO and 10% fetal bovine serum.

Preferably, any native or exogenous protease activity is inhibited or prevented in the preparation of the biomaterial. Additives to the decellularization, rinse and/or storage solutions such as metal ion chelators, for example 1,10-phenanthroline and ethylenediaminetetraacetic acid (EDTA), create an environment unfavorable to many proteolytic enzymes. Providing sub-optimal conditions for proteases (e.g., collagenase) assists in protecting umbilical cord biomaterial components such as collagen from degradation during the cell lysis step. Suboptimal conditions for proteases may be achieved by formulating the decellularization solution to eliminate or limit the amount of available calcium and zinc ions. Many proteases are active in the presence of calcium and zinc ions and lose much of their activity in calcium and zinc ion free environments. Preferably, the decellularization solution is prepared, in part, by selecting conditions of pH, reduced availability of calcium and zinc ions, presence of metal ion chelators and the use of proteolytic inhibitors specific for collagenase, such that the solution will optimally lyse the native umbilical cord cells while protecting the umbilical cord biomaterial from proteolytic degradation. For example, a decellularization solution can include a buffered solution of water, pH 5.5 to 8, preferably pH 7 to 8, free from calcium and zinc ions and including a metal ion chelator such as EDTA. Decellularization can take place at, e.g., between 0° C. and 25° C., preferably below about 10° C., to reduce protease activity.

It is preferred that the decellularization treatment also limits the generation of new immunological sites. Since enzymatic degradation of, e.g., collagen is believed to lead to heightened immunogenicity, the invention encompasses treatment of the umbilical cord biomaterial with enzymes, e.g., nucleases, that are effective in inhibiting cellular metabolism, protein production and cell division, that minimize proteolysis of the components of the umbilical cord biomaterial thus preserving the underlying architecture of the amniotic biomaterial. Examples of nucleases that can be used in accordance with the methods of the invention are those effective in digestion of native cell DNA and RNA including both exonucleases and endonucleases. A non-limiting example of nucleases that can be used in accordance with the methods of the invention include exonucleases that inhibit cellular activity, e.g., DNase I (SIGMA Chemical Company, St. Louis, Mo.) and RNase A (SIGMA Chemical Company, St. Louis, Mo.) and endonucleases that inhibit cellular activity, e.g., EcoRI (SIGMA Chemical Company, St. Louis, Mo.) and HindIII (SIGMA Chemical Company, St. Louis, Mo.). It is preferable that the selected nucleases are applied in a physiological buffer solution which contains ions, e.g., magnesium, calcium, which are optimal for the activity of the nuclease. Preferably, the ionic concentration of the buffered solution, the treatment temperature and the length of treatment are selected by one skilled in the art by routine experimentation to assure the desired level of nuclease activity. The buffer is preferably hypotonic to promote access of the nucleases to cell interiors.

In another embodiment of the invention, the umbilical cord biomaterial is not decellularized prior to drying.

In another embodiment of the above steps, the umbilical cord, after initial processing, is briefly rinsed in saline to remove blood from the umbilical cord surface. The umbilical cord is then immersed in a cold deoxycholic acid solution at a concentration of about 0.1% to about 10%, and, in a specific embodiment, about 0.1% to about 2.0%. The umbilical cord is then incubated in this solution at between about 1° C. to about 8° C. for about 5 days to about 6 months. In specific embodiments, the umbilical cord is immersed, for example, for about 5 to about 15 days; about 5 to about 30 days, about 5 to about 60 days, or for up to about one year. Typically, the deoxycholic acid solution is replaced during incubation every 2-5 days. In another specific embodiment, the umbilical cord is immersed in a deoxycholic acid solution at a concentration of about 1% at a temperature of 0° C. to about 8° C. for about 5 days to about 15 days. This incubation serves two purposes. First, it allows time for serological tests to be performed on the umbilical cord and/or umbilical cord blood, so that umbilical cords failing to meet serological criteria are not processed further. Second, the longer incubation improves the removal of epithelial cells and fibroblasts, which allows for a significant reduction in the amount of time spent decellularizing the umbilical cord membrane by physically scraping. The umbilical cord biomaterial can then be dried as described below.

Following decellularization, the umbilical cord biomaterial is generally washed to assure removal of cellular debris (e.g., cellular proteins, cellular lipids, cellular nucleic acids, extracellular debris such as extracellular soluble proteins, lipids and proteoglycans, and the like). The wash solution can be de-ionized water or an aqueous hypotonic buffer. Preferably, the umbilical cord biomaterial is gently agitated, e.g., for 15-120 minutes in the detergent, e.g., on a rocking platform, to assist in the decellularization. The umbilical cord biomaterial, after detergent decellularization, can again be physically decellularized as described above; the physical and detergent decellularization steps may be repeated as necessary, as long as the integrity of the umbilical cord biomaterial is maintained, until no visible cellular material and cellular debris remain.

In certain embodiments, the umbilical cord biomaterial is dried immediately (i.e., within 30 minutes) after decellularization and/or washing. Alternatively, when further processing is not done immediately, the umbilical cord biomaterial may be refrigerated, e.g., stored at a temperature of about 1° C. to about 20° C., preferably from about 2° C. to about 8° C., for up to 28 days prior to drying. When the umbilical cord biomaterial, e.g., decellularized umbilical cord biomaterial, is stored for more than three days, the sterile solution covering the umbilical cord biomaterial is preferably changed periodically, e.g., every 1-3 days.

In certain embodiments, when the umbilical cord biomaterial is not refrigerated after washing, the biomaterial can be washed, e.g., washed at least 3 times, prior to proceeding to the next step of the preparation. In other embodiments, when the umbilical cord biomaterial has been refrigerated and the sterile solution has been changed once, the umbilical cord biomaterial can be washed at least twice prior to the next step of the preparation. In yet other embodiments, when the umbilical cord biomaterial has been refrigerated and the sterile solution has been changed twice or more, the umbilical cord biomaterial can be washed at least once prior to proceeding to the next step.

The final step in this embodiment comprises drying the decellularized umbilical cord membrane to produce the umbilical cord biomaterial of the invention. Any method of drying the umbilical cord membrane can be used. For example, the membrane can be dried using heat, one or more hygroscopic compounds, freeze-drying, vacuum, microwaving, simple evaporation, and the like, or combinations of these methods. Preferably, the biomaterial is dried under vacuum.

The umbilical cord biomaterial can be dried in any useful conformation. Preferably, the umbilical cord biomaterial is dried so as to produce a flat, dry sheet. The biomaterial can also be dried as a tube, strip, spiral, string or rope, or the like. For three-dimensional shapes, the biomaterial can be placed onto, or into, a form and dried, so that the dried biomaterial assumes the shape of the form or a part thereof. In a specific embodiment, for example, the umbilical cord membrane can be supported by rubber hose or tubing inserted from one end, and freeze-dried to form a dried tube of the umbilical cord biomaterial. At this point, the umbilical cord biomaterial can be, e.g., part of a complete umbilical cord that has been washed and rinsed; an umbilical cord biomaterial comprising Wharton's jelly but lacking vessels, an umbilical cord biomaterial that has had the interior components of the umbilical cord removed, and has been decellularized, etc. In each case, the biomaterial can be dried.

In a specific embodiment, an exemplary method for drying the umbilical cord biomaterial comprises the following steps:

Assembly of the umbilical cord biomaterial for drying. The umbilical cord biomaterial is removed from the sterile solution, and the excess fluid is gently squeezed out. The umbilical cord biomaterial is then gently stretched until it is flat with the epithelial side facing in a downward position, e.g., on a tray. The umbilical cord biomaterial is then placed on a drying frame, preferably a plastic mesh drying frame (e.g., QUICK COUNT® Plastic Canvas, Uniek, Inc., Waunakee, Wis.). In other embodiments, the drying frame may be any autoclavable material, including but not limited to a stainless steel mesh. Once the umbilical cord biomaterial is positioned on the drying frame, a sterile gauze can be placed on the drying platform of a heat dryer (or gel-dryer) (e.g., Model 583, Bio-Rad Laboratories, Hercules, Calif.), so that an area slightly larger than the umbilical cord biomaterial resting on the plastic mesh drying frame is covered. Preferably, the total thickness of the gauze layer does not exceed the thickness of one folded 4×4 gauze. Any heat drying apparatus may be used that is suitable for drying sheet-like material. The drying frame is placed on top of the gauze on the drying platform so that the edges of the plastic frame extend above beyond the gauze edges, preferably between 0.1-1.0 cm, more preferably 0.5-1.0 cm. In some embodiments, another plastic framing mesh is placed on top of the umbilical cord biomaterial. In another embodiments, a sheet of thin plastic (e.g., SW 182, clear PVC, AEP Industries Inc., South Hackensack, N.J.) or a biocompatible silicone is placed on top of the biomaterial covered mesh so that the sheet extends well beyond all of the edges. In this embodiment, the second mesh frame is not needed.

In an alternative embodiment, the umbilical cord biomaterial is placed one or more sterile sheets of TYVEK® material (e.g., a sheet of TYVEK® for medical packaging, DuPont TYVEK®, Wilmington, Del.), optionally, with one sheet of TYVEK® on top of the biomaterial (prior to placing the plastic film). This alternate process will produce a smoother version of the biomaterial (i.e., without the pattern of differential fiber compression regions along and perpendicular to the axis of the material), which may be advantageous for certain applications, such as for example for use as a matrix for expansion of cells.

Drying the umbilical cord biomaterial. In a preferred embodiment, the invention encompasses heat drying the umbilical cord biomaterial of the invention under vacuum. While the drying under vacuum may be accomplished at any temperature from about 0° C. to about 60° C., the umbilical cord biomaterial is preferably dried at between about 35° C. and about 50° C., and most preferably at about 50° C. It should be noted that some degradation of the collagen is to be expected at temperatures above 50° C. The drying temperature is preferably set and verified using a calibrated digital thermometer using an extended probe. Any amount of vacuum that can be conveniently generated can be used, but preferably, the vacuum pressure is set to about −22 inches of Hg. The drying step is continued until the umbilical cord biomaterial is substantially dry, that is, contains less than 20% water by weight, and preferably, about 3-12% water by weight as determined for example by a moisture analyzer. To accomplish this, the umbilical cord biomaterial may be heat-vacuum dried, e.g., for approximately 60 minutes to achieve a dehydrated umbilical cord biomaterial. In some embodiments, the umbilical cord biomaterial is dried for about 30 minutes to 2 hours, preferably about 60 minutes. Although not intending to be bound by any mechanism of action, it is believed that low (e.g., <50° C.) heat coupled with vacuum pressure allows the umbilical cord biomaterial to achieve the dehydrated state without denaturing collagen in the biomaterial. After completion of the drying process in accordance with the invention, the umbilical cord biomaterial can be cooled down, e.g., for approximately two minutes, with the vacuum pump running.

Packaging and Storing of the Umbilical Cord Biomaterial. Once the umbilical cord biomaterial is dried, the biomaterial is gently lifted off the drying frame. Preferably, handling of the umbilical cord biomaterial at this stage is done with sterile gloves. The umbilical cord biomaterial can be placed in a sterile container, e.g., peel pouch. When dried, the umbilical cord biomaterial produced in accordance with the methods of the invention may be stored at room temperature for an extended period of time as described supra.

In another embodiment, the umbilical cord biomaterial is prepared as above, but is not decellularized. That is, the umbilical cord membrane is obtained and dried, but the cells associated with the umbilical cord membrane are not removed. The final, dried product thus comprises, e.g., the umbilical cord membrane and/or umbilical cord vessel(s), as well as cellular components.

The umbilical cord biomaterial can be dehydrated by other methods in place of, or in addition to, the vacuum-drying method outlined above. For example, in one embodiment, the biomaterial can be freeze dried. Typically, umbilical cord biomaterial can be frozen at a temperature between about −170° C. and about 0° C. for time sufficient for the biomaterial to completely freeze. The frozen biomaterial is freeze-dried process during which the ice crystals will be removed or avoided by sublimation under vacuum.

In another embodiment, the biomaterial can be dehydrated using a solvent. For example, umbilical cord biomaterial can be dehydrated using, e.g., ethanol and acetone. In this specific embodiment, the biomaterial can be, e.g., soaked for a time in a series of ethanol-acetone mixtures (e.g., 20%, 40%, 60%, 80% and 100% ethanol, or a similar progression of equivalent solvents that act to extract water) such that the water inside the biomaterial is gradually replaced by the organic solvent. After the final soak, the biomaterial can be placed in a well-ventilated place at room temperature (about 23° C.) for a time sufficient for the solvent to evaporate. The biomaterial can alternately be vacuum-dried after the solvent soak.

In another embodiment, the biomaterial can also be dehydrated by freeze drying. For example, in a specific embodiment in a combination of the above two processes, the processed membrane can be first frozen and then transferred to a water miscible organic solvent. Ice crystals inside the membrane tissue may then be dissolved and replaced by the organic solvent using a series of progressive solvent soaks as described above. After the final soak, the biomaterial can be placed in a well-ventilated place at room temperature (e.g., about 20° C. to about 25° C.) for a time sufficient for the ethanol to evaporate. The biomaterial can alternately be vacuum-dried after the 100% ethanol soak.

Non-heat drying processes may be preferred if the porous structure of the biomaterial and/or bioactivity of the biological substances within the umbilical cord membrane need to be preserved, for example, if the biomaterial is to be used as a substrate or matrix for the transport of stem cells to a graft site, or if, e.g., the biomaterial is to be preloaded with a heat-sensitive drug as a drug release device, or if, e.g., the biomaterial is preloaded with a heat sensitive drug as a drug release device.

When the above steps are complete, the membrane generally primarily comprises collagen (types I, III, IV, V, VI and VII), glycosaminoglycans (particularly hyaluronic acid); and growth factors, particularly fibroblast growth factor (FGF), basic fibroblast growth factor (b-FGF), epidermal growth factor (EGF), insulin-like growth factor I (IGF-I), platelet-derived growth factor (PDGF) and transforming growth factor beta (TGF-β).

5.1.5 Storage and Handling of Umbilical Cord Biomaterial

Dehydrated umbilical cord biomaterial may be stored, e.g., as dehydrated sheets, at room temperature (e.g., 25° C.) prior to use. In certain embodiments, the umbilical cord biomaterial can be stored at a temperature of at least 10° C., at least 15° C., at least 20° C., at least 25° C., or at least 29° C. Preferably, umbilical cord biomaterial, in dehydrated form, is not refrigerated. In some embodiments, the umbilical cord biomaterial may be refrigerated at a temperature of about 2° C. to about 8° C. The umbilical cord biomaterial produced according to the methods of the invention can be stored at any of the specified temperatures for 12 months or more with no alteration in biochemical or structural integrity (e.g., no degradation), without any alteration of the biochemical or biophysical properties of the umbilical cord biomaterial. The biomaterial can be stored for several years with no alteration in biochemical or structural integrity (e.g., no degradation), without any alteration of the biochemical or biophysical properties of the biomaterial. The biomaterial can be stored in any container suitable for long-term storage. Preferably, the umbilical cord biomaterial of the invention is stored in a sterile double peel-pouch package.

The umbilical cord biomaterial, in embodiments in which the material has been dried, may be hydrated prior to use, using, e.g., a sterile physiological buffer. In a specific embodiment, the sterile saline solution is a 0.9% NaCl solution. In some embodiments the sterile saline solution is buffered. In certain embodiments, the hydration of the umbilical cord biomaterial requires at least 2 minutes, at least 5 minutes, at least 10 minutes, at least 15 minutes, or at least 20 minutes. In a preferred embodiment, the hydration of the umbilical cord biomaterial is complete within 5 minutes. In yet another preferred embodiment, the hydration of the umbilical cord biomaterial of the invention is complete within 10 minutes. In yet another embodiment, the hydration of the umbilical cord biomaterial takes no more than 10 minutes. Once hydrated, the umbilical cord biomaterial can be maintained in solution, e.g., in sterile 0.9% NaCl solution, for up to six months, with a change of solution, e.g., every three days.

5.1.6 Sterilization

Sterilization of the umbilical cord biomaterial may be accomplished by any medically-appropriate means, preferably means that do not significantly alter the tertiary and quaternary structure of the biomaterial proteins. Sterilization can be accomplished, for example, using gas, e.g., ethylene dioxide. Sterilization can be accomplished using radiation, for example, gamma radiation, and is preferably done by electron beam irradiation using methods known to one skilled in the art, e.g., Gorham, D. Byrom (ed.), 1991, *Biomaterials*, Stockton Press, New York, 55-122. Any dose of radiation sufficient to kill at least 99.9% of bacteria or other potentially contaminating organisms is within the scope of the invention. In a preferred embodiment, a dose of at least 18-25 kGy is used to achieve the terminal sterilization of the biomaterial.

5.1.7 Laminates

The umbilical cord biomaterial may be laminated to provide greater load-bearing capacity and durability during the healing process. Laminates of the umbilical cord biomaterial can comprise biomaterial from a single umbilical cord, wherein the composition is folded once, or a plurality of times, longitudinally or laterally, or both. Laminates of the biomaterial can also comprise two or more sheets of biomaterial.

The umbilical cord biomaterial, being anisotropic, has two orientations, longitudinal (that is, along the length of the umbilical cord membrane) and lateral (that is, around the width of the umbilical cord). Where a laminate comprises two sheets of the umbilical cord biomaterial, the sheets can be laminated so that each sheet is oriented the same way (e.g., each sheet oriented longitudinally), or such that at least one sheet is oriented laterally and one longitudinally. In other embodiments, each of the layers of umbilical cord biomaterial can be laminated in any orientation with respect to any other layer of the biomaterial in the laminate.

The umbilical cord has a sidedness; that is, the umbilical cord biomaterial has an epithelial side (that is, the side towards the interior of the umbilical cord) and a mesothelial side (that is, the side towards the exterior of the umbilical cord). Laminates can comprise two or more layers of the umbilical cord biomaterial in any sidedness configuration. For example, laminates can comprise layers of umbilical cord biomaterial in which only the endothelial sides of the layers are in contact; only the mesothelial sides of the layers are intact; or a combination of both. In one embodiment, a laminate comprises four layers, wherein two sets of two layers, contacted endothelial to mesothelial sides, are contacted by the exposed mesothelial side such that the two faces of the laminate show the endothelial sides.

Umbilical cord biomaterial can be laminated, e.g., by folding a single sheet of biomaterial, or by stacking 2 or more layers of the biomaterial one atop the other, and sealing or drying. The biomaterial may be laminated either dry or after rehydration. Alternatively, two or more layers of, e.g., umbilical cord biomaterial, or composition comprising an umbilical cord biomaterial, can be laminated prior to initial drying after cell removal, e.g., after a cell scraping step (see Examples, below). If laminated prior to the initial drying, 2 or more biomaterial layers can be stacked one atop the other and subsequently dried, using, for example, a freeze-drying process, or drying under moderate heat with or without vacuum. The heat applied preferably is not so intense as to cause breakdown or decomposition of the protein components, especially the collagen, of the umbilical cord biomaterial. Typically, the heat applied is less than about 70° C., preferably less than about 60° C., and, more preferably, is approximately 50° C. Lamination time varies with, e.g., the number of layers being laminated, but typically takes 1-2 hours at 50° C. Thus, a method of preparing a laminate using a composition comprising umbilical cord membrane comprises layering a plurality of said membranes in contact with each other to form a laminate. In some embodiments, each of said membranes comprises less than 20% water by weight prior to said layering. In certain embodiments, said laminate is dried to less than 20% water by weight after said layering.

The biomaterial may also be laminated using an adhesive applied between 2 or more layers of biomaterial or umbilical cord biomaterial or composition comprising an umbilical cord biomaterial. Such an adhesive is preferably appropriate for medical applications, and can comprise a natural biological adhesive, for example fibrin glue, a synthetic adhesive, or combinations thereof. The adhesive may further be chemically converted from precursors during the lamination process.

Laminates of the umbilical cord biomaterial can comprise, for example, umbilical cord biomaterial that has been decellularized, biomaterial that retains the cellular material (that is, where the cells have been killed, but not removed), or biomaterial comprising living umbilical cord cells or cells of another type (e.g., where cells have been cultured on a sheet of umbilical cord biomaterial).

A laminate can comprise a second type of material, e.g., one or more layers of umbilical cord biomaterial can be layered with one or more layers of a second biologically-compatible material, e.g., a sheetlike material such as, e.g., amniotic membrane. Where the second material has a "grain" or orientation, the umbilical cord biomaterial can be laminated such that the biomaterial lies with its longitudinal direction along, or alternatively across, the grain of the second material. In a specific, preferred embodiment, the umbilical cord membrane biomaterial is laminated with at least one other layer of a second material that has a relatively high load-bearing capacity. The umbilical cord biomaterial can also be laminated with a non-biological material, e.g., plastic, e.g., TYVEK® or the like. In a preferred embodiment, the umbilical cord biomaterial laminate comprises two layers of the biomaterial and one layer of plastic, e.g., TYVEK®, such that the plastic is sandwiched between the two layers of umbilical cord biomaterial, and the endothelial sides of the biomaterial contact the plastic. In another preferred embodiment, one layer of umbilical cord membrane is placed on a plastic sheet with the epithelial side down, and a second piece of umbilical cord membrane is placed on the first epithelial side up. The resulting product is then heat-dried to produce an umbilical cord biomaterial laminate.

In various embodiments, the second material has a load-bearing capacity or tensile strength, for, e.g., a 2-centimeter wide section, of at least 25 milliPascals (mPa), 50 mPa, 75 mPa, 100 mPa, 125 mPa, 150 mPa, 175 mPa, 200 mPa, 225 mPa, 250 mPa, 275 mPa, 300 mPa, 325 mPa, 350 mPa, 375 mPa, 400 mPa, 425 mPa, 450 mPa, 475 mPa, 500 mPa, 750 mPa, 1000 mPa, 1250 mPa, 1500 mPa, 1750 mPa or 2000 mPa. Load-bearing capacities of sections that are wider or narrower would be accordingly more or less. Such a second material can be sheetlike, or can be formed into a shape suitable for a particular application, and the umbilical cord biomaterial molded to the shape of the second material. For example, the second material can be, e.g., a material suitable for, and shaped for, tendon or ligament repair. The umbilical cord biomaterial can be wrapped around such a second material so that the exterior of the laminate is biologically compatible, and the interior is load-bearing.

The load-bearing capacity of a particular umbilical cord biomaterial laminate, or piece of umbilical cord biomaterial, can be tested by standard methods known in the art, such as ASTM D1708 (Standard Test Method for Tensile Properties of Plastics).

In one embodiment, the laminate comprises at least two sheets of umbilical cord biomaterial approximately the same size and shape laid one atop the other so that the shape is substantially maintained. Such a laminate can be trimmed to finalize a particular shape. In another embodiment, the laminate comprises two or more sheets of umbilical cord biomaterial, wherein a portion of each of the sheets overlaps another. In this embodiment, several overlapping sheets of umbilical cord biomaterial can be laminated to form a larger sheet of the biomaterial than would be possible from a single umbilical cord. In a specific embodiment, such a laminate of overlapping sheets of the biomaterial can itself be laminated with another layer of a material, e.g., another overlapping biomaterial laminate; individual sheets of umbilical cord biomaterial; another type of biomaterial, e.g., an amniotic membrane-derived biomaterial; an artificial sheet or film; etc.

5.1.8 Stem Cells

The umbilical cord biomaterial as described herein can also comprise stem or progenitor cells. The umbilical cord biomaterial can comprise, e.g., mesenchymal or mesenchymal-like stem cells, for example, those described in U.S. Pat. Nos. 5,486,359, 6,261,549 and 6,387,367, or placental stem cells such as those described in U.S. Application Publication Nos. 2002/0123141, 2003/0032179 and 2003/0180269. However, the umbilical cord biomaterial may comprise stem or progenitor cells, preferably mammalian stem or progenitor cells, from any tissue source. The umbilical cord biomaterial can comprise embryonic stem cells or embryonic germ cells.

The umbilical cord biomaterial and stem or progenitor cells can be combined, e.g., in advance of a procedure in which the biomaterial is contacted with an individual having a disease, disorder or condition that would be amenable to treatment using an umbilical cord biomaterial. For example, stem cells can be contacted with, e.g., disposed onto, the biomaterial sufficiently in advance of such a procedure for a plurality, a majority, or substantially all of the stem cells to adhere to the biomaterial. The stem cells can be contacted with the biomaterial immediately before the biomaterial is contacted with the individual. The stem cells can also be contacted with the biomaterial in situ, after the biomaterial is contacted with the individual. The number of stem or progenitor cells disposed onto the surface of the umbilical cord biomaterial may vary, but may be at least about $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, or $1\times10^{12}$; or may be no more than $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, or $1\times10^{12}$ stem or progenitor cells.

The stem cells, at any of the times noted above, can be contacted with one or more differentiation-modulating agents, for example, the differentiation-modulating agents described in U.S. Application Publication Nos. 2003/0235909 and/or 2004/0028660, the disclosures of which are incorporated by reverence in their entireties herein, or International Application Publication No. WO 03/087333. Methods of differentiating stem cells to, for example, epidermal, mesodermal, and other cell types are known in the art, and are described, e.g., in U.S. Application Publication No. 2004/0028660.

5.2 Uses of Umbilical Cord Biomaterial

The umbilical cord biomaterial can be used in a variety of medical applications. The uses outlined in this section are non-limiting examples of such applications.

5.2.1 Repair of Joints, Ligaments, and Tendons

The umbilical cord biomaterial of the invention can be used, for example, to repair or replace ligaments, tendons and/or cartilage. The biomaterial can be contacted with a ligament, tendon or cartilage in any medically-acceptable manner that tends to facilitate healing of a defect in the ligament, tendon or cartilage.

The umbilical cord biomaterial can be used, for example, to repair a defect in a tendon, ligament or cartilage where the defect is a tear, that is, a defect that is less than a complete failure. The repair comprises contacting the tendon, ligament or cartilage with the umbilical cord biomaterial such that a part, or preferably all, of the defect is covered by the biomaterial. The umbilical cord biomaterial can be, for example, wrapped around a tendon or ligament at the site of the defect, or a patch of umbilical cord biomaterial of sufficient size to cover the defect can be placed on the defect. The biomaterial can be held in place using, e.g., a biologically-acceptable glue, e.g., a tissue glue, or can be sutured in place. Preferably, the umbilical cord biomaterial is held in place such that the biomaterial assumes at least part of the biomechanical load normally associated with the functional tendon, ligament or cartilage.

The umbilical cord biomaterial can be used, for example, to repair a defect in a tendon, ligament or cartilage where the defect is a complete rupture or failure of a tendon, ligament or cartilage. The repair comprises contacting the tendon, ligament or cartilage with the umbilical cord biomaterial so as to partially, or preferably completely, cover the defect. Preferably, the contacting is such that the biomaterial assumes some, or all of the biomechanical load normally assumed by the tendon, ligament or cartilage. For example, a rupture in a tendon can be repaired by contacting the tendon at the site of the rupture with the biomaterial and affixing the biomaterial in place. The two parts of the tendon at the site of the rupture are preferably brought into contact with each other, and the biomaterial is preferably wrapped around the site of the break. The biomaterial can be sutured to the two parts of the ruptured tendon such that it acts as a splint, holding the to ends of the rupture together. The biomaterial can be wrapped around such a rupture once, or preferably a plurality of times.

The umbilical cord biomaterial can be used, for example, to replace a tendon or ligament, or to support a joint where one or more of the native ligaments is weakened. In such an embodiment, the biomaterial attaches two bones, or a muscle and bone, in place of a damaged, diseased or ruptured tendon or ligament, e.g., an anterior cruciate ligament.

In a specific embodiment, for example, to replace a cruciate ligament, e.g., an anterior cruciate ligament, tunnels can be drilled onto the femoral and tibial heads adjoining the knee. The biomaterial, e.g., folded lengthwise a plurality of times into a rope-like conformation, can be drawn through the tunnels, and the ends fastened to the respective bones. Such fastening can be accomplished by any means known in the art, e.g., using screws, staples, or the like. In a specific embodiment, the ends of the umbilical cord biomaterial are folded over to provide a portion of the biomaterial of greater thickness for fastening. Such replacement can comprise removing the native ligament during replacement, or can comprise adding the biomaterial and allowing the native ligament to remain. In preferred embodiments, the umbilical cord biomaterial is laminated with a load-bearing material, such as plastic sheeting, e.g., TYVEK® prior to folding into the rope-like conformation.

In another embodiment, the umbilical cord biomaterial can be used to repair a tendon in the hand. In a specific embodiment, for example, the umbilical cord biomaterial is inserted between one or more extensor tendons in the hand and bones to provide a gliding surface or a shield between tendon and bone, e.g., to prevent adhesion formation.

Preferably, the umbilical cord biomaterial is stretched prior to repair or replacement of a ligament or tendon. For example, a weight, bearable by the particular piece of biomaterial, can be suspended from the biomaterial for a time sufficient to allow up to, e.g., about 10%, 15%, or about 20% elongation. Such stretching tends to prevent loosening of the biomaterial after application.

The umbilical cord biomaterial, in another embodiment, can also be used to repair or reinforce a rotator cuff tendon having a defect, e.g., a tear. In a preferred embodiment, a piece of the umbilical cord biomaterial is used to completely cover the rotator cuff tendon defect.

5.2.2 Tympanic Membrane Repair and Other Aural Applications

In another embodiment, the present invention provides methods and compositions for repair of a tympanic membrane using an umbilical cord biomaterial. In one embodiment, the present invention provides a method of repairing a perforated tympanic membrane, comprising contacting said tympanic membrane with a umbilical cord biomaterial. Said contacting can comprise shaping a flat piece of the biomaterial into the shape of an entire, or a portion of, a tympanic membrane, and contacting the biomaterial with the tympanic membrane. In another specific embodiment, said perforation has not healed spontaneously within two months of the appearance of the perforation. As with other applications, the biomaterial can be contacted with the tympanic membrane while hydrated, or, preferably, while substantially dry (e.g., comprising less than 20% water by weight). The biomaterial can be a single layer, or can be a laminate of two or more layers. In another embodiment, the umbilical cord biomaterial (whether a single layer or a laminate) contacted with the tympanic membrane is at least about 70 microns in thickness.

In one embodiment of repairing a tympanic membrane, a tympanic membrane having a perforation is contacted with an umbilical cord biomaterial such that the biomaterial partially or totally occludes the perforation. The perforation to be occluded may be a central perforation, that is, a perforation of any size that does not involve the margin of the tympanic membrane (i.e., the periphery seated in the auditory canal), or a marginal perforation (i.e., a perforation touching upon, or largely involving, the margin of the tympanic membrane). In another embodiment, only the tympanic membrane is perforated, and no other ear structure is perforated or damaged. In another embodiment, occlusion of the perforation is an adjunct to at least one other surgical procedure involving the outer, middle, or inner ear. In another embodiment, the repair of the tympanic membrane is a tympanoplasty. In another embodiment, the repair of the tympanic membrane is a myringoplasty.

The benefits of closing a tympanic membrane perforation include prevention of water entering the ear while showering, bathing or swimming (which could cause ear infection), improved hearing, and diminished tinnitus. Closure also helps to prevent the development of cholesteatoma (skin cyst in the middle ear), which can cause chronic infection and destruction of ear structures.

Tympanoplasty and myringoplasty are generally outpatient procedures. The otolaryngologist may approach repair of a tympanic membrane perforation either through the auditory canal (trans-canal approach), or via a post-auricular incision followed by folding the ear forward to expose the tympanic membrane (post-auricular approach).

Before attempting any correction of the perforation, a hearing test is generally performed, and the patient is evaluated for Eustachian tube function, as partial or complete loss of Eustachian tube function can exacerbate a tympanic membrane puncture and interfere with the adherence of a graft to the tympanic membrane. Repair of a perforated tympanic membrane generally comprises placing an occluding material on the membrane. The patient is evaluated for complications, such as extension of squamous epithelium through the perforation and into the middle ear space. In such instances, tympanoplasty or myringoplasty is preferably accompanied, where possible, by remediation of the complication.

The present invention encompasses repair of a tympanic membrane with an umbilical cord biomaterial either as a first or subsequent therapy. That is, the biomaterial may be used to repair a tympanic membrane deformity, such as a perforation, before other remedial measures are tried. Alternatively, repair of a tympanic membrane with biomaterial may be performed after one or more other remedial measures have been tried and failed.

In one embodiment, repair of a tympanic membrane with biomaterial may additionally comprise applying an anti-infective agent to the graft and/or surrounding ear canal. Thus, in one embodiment, the invention provides a method of repairing a tympanic membrane comprising contacting the tympanic membrane with an umbilical cord biomaterial and an anti-infective agent, e.g., one of the anti-infective agents listed in Section 5.1.2, above. The anti-infective agent can be contacted either prior to, concurrently with, or subsequent to contacting the tympanic membrane with the umbilical cord biomaterial. The anti-infective agent can be present separate from, or as an integral part of, the biomaterial. For example, the anti-infective agent can be present on the surface of the biomaterial, or can be impregnated in the biomaterial. In a specific example, the anti-infective agent is an antibiotic, a bacteriostatic agent, antiviral compound, a virustatic agent, antifungal compound, a fungistatic agent, or an antimicrobial compound. In a specific embodiment, the anti-infective agent is ionic silver. In a more specific embodiment, the ionic silver is contained within a hydrogel. Ionic silver hydrogel is a preferred anti-infective agent because it is broad spectrum, with no known bacterial resistance; its application and removal are pain-free, and the hydrogel supports autolytic debridement. In a preferred embodiment, the umbilical cord biomaterial is impregnated with silver ions prior to application to the tympanic membrane. In another embodiment, the umbilical cord biomaterial is impregnated with silver ions after application of the biomaterial to the tympanic membrane, for example, by application of ear drops.

The invention further provides that the use of an umbilical cord biomaterial to repair a tympanic membrane deformity may be the sole treatment of the tympanic membrane, or may be in addition to another therapies or treatment used simultaneously in the course of treating or repairing a tympanic membrane. For example, the invention provides for the repair of a tympanic membrane comprising contacting the tympanic membrane with an umbilical cord biomaterial, and treating the tympanic membrane using an additional therapy not comprising contacting the tympanic membrane with an umbilical cord biomaterial, where the contacting and the additional therapy individually or together cause a measurable improvement in, maintenance of, or lessening of the worsening of, at least one aspect of a tympanic membrane deformity, as compared to a tympanic membrane not contacted with an umbilical cord biomaterial.

The invention further provides for the use of umbilical cord biomaterial to repair an ear condition in conjunction with repair of a tympanic membrane. For example, the umbilical cord biomaterial can be used to reconstruct or repair the outer or middle ear structures, including the auditory canal and middle ear chamber. The umbilical cord biomaterial, for example, may be used to repair or line the mastoid cavity, particularly where mastoid reconstruction is indicated in addition to tympanoplasty. In one embodiment, the umbilical cord biomaterial may be used to line the mastoid cavity where the mastoid cavity comprises exposed bone, that is, bone with no covering epithelial cell layer. In another embodiment, the umbilical cord biomaterial may be used as a oval window graft in stapes surgery, either alone or in conjunction with tympanoplasty or myringoplasty.

5.2.3 Soft Tissue Repair

In another non-limiting embodiment, the invention further provides for the use of umbilical cord biomaterial to repair a soft tissue injury or defect in an individual. In one embodiment, the soft tissue defect is an abdominal wall defect. Such an abdominal wall defect, e.g., hernia, is repaired by suturing one or more sheets of umbilical cord biomaterial, either a single sheet or a laminate of sheets as disclosed elsewhere herein, either dried or hydrated, to the soft tissue such that the defect is repaired or ameliorated. In a specific embodiment, the soft tissue defect is a hernia or abdominal wall defect in which the abdominal wall allows exit of at least part of an organ from the abdominal cavity. In this embodiment, the defect, e.g., discontinuity or hernia, is preferably completely covered with one or more sheets of umbilical cord biomaterial, whether or not the discontinuity or hernia has been surgically closed. Typically, the umbilical cord biomaterial is sutured, stapled, or otherwise fastened to the defect such that repair is effected. In other specific embodiments, said soft tissue defect is a defect in the pelvic floor, an enteroceles, a rectoceles, or a cystoceles. In embodiments in which the abdominal wall defect is an opening of the abdominal wall to the exterior of the body, it is generally preferred that the defect be contacted with the mesothelial surface of the umbilical cord biomaterial.

In another specific embodiment, the defect is incontinence, and the umbilical cord biomaterial is used as an adjunct to a suburethral sling procedure to assist in the repair of gracilis muscle flaps sutured beneath the urethra.

In another specific embodiment, the soft tissue defect is a leg ulcer such as, e.g., a venous leg ulcer, arterial leg ulcer, diabetic ulcer or decubitus ulcer. Repair of a leg ulcer can comprise contacting a portion, or the entirety, of the leg ulcer with one or more pieces of umbilical cord biomaterial, either a single sheet or a laminate thereof, either dried or hydrated, such that the umbilical cord biomaterial becomes affixed to the leg ulcer. Typically, the biomaterial becomes affixed to the leg ulcer without fastening; however, the biomaterial can be sutured, stapled or glued to the skin surrounding the ulcer, or can be held in place by, e.g., a bandage or compression boot, or by any other method known to those of skill in the art.

In another specific embodiment, the soft tissue defect is a surgical adhesion. In a more specific embodiment, the surgical adhesion is an adhesion resulting from, e.g., gynecological surgery. It is estimated that approximately 97% of surgical patients develop adhesions after surgery and of these, between 5% and 8% develop complications. Without being bound by theory, the umbilical cord biomaterial would be an effective barrier to adhesions in that the amnion epithelial cells on one side of the biomaterials would occupy cell binding sites, making it difficult for host cells, such as fibroblasts, to attach and penetrate. Thus, the umbilical cord biomaterial can be used to prevent surgical adhesion by placing the biomaterial between two tissues that would ordinarily be expected to form a post-surgical adhesion.

In another specific embodiment, the soft tissue defect is a nasal septal perforation. The septal perforation may arise from any cause, e.g., inherited defect, trauma, drug use, etc. A piece of umbilical cord biomaterial, suitably shaped, can be placed along the septum in order to partially or completely occlude the perforation, and can be held in place by one or several sutures or tissue glue.

5.2.4 Ocular Plugs

In another non-limiting embodiment, the invention further provides for the use of umbilical cord biomaterial in the formation of an ocular plug. An ocular plug at least partially, or, preferably, completely, occludes a hole in, e.g., the sclera, that is, e.g., caused by an injection, formed as a part of a surgical procedure to, e.g., allow insertion of a surgical tool into the lumen of the eye; caused by trauma; etc. Ocular plugs may be configured in any shape to accomplish the particular purpose at hand, e.g., occluding injection or ocular surgery-related holes in the sclera, prevention of leakage, drug delivery, anchoring of the plug, etc.

In one, preferred, embodiment, the invention provides an ocular plug that comprises a shaft attached to and extending from a cap. Typically, the cap is circular when viewed from the upper face. However, the cap may be oval, square, rectangular, polygonal, irregular, or may appear as a plurality of flanges extending substantially perpendicularly from the shaft. The upper face of the cap distal to the shaft, may be hemispherical, curved to a degree other than completely hemispherical, or may be substantially flat. Preferably, the surface of the upper face of the cap is shaped to approximate the curvature of the eye to promote comfort and reduce the possibility of inflammation or irritation associated with the eyelid moving over the face of the cap. The lower face of the cap proximal to the shaft may be substantially flat, but is preferably shaped to approximate the curvature of the eye. Preferably, the cap tapers towards the edges so that a smooth transition is made from sclera to cap when the eyelid passes over the cap. However, the cap need not taper from center towards the edges, and may have a discernibly blunt edge.

The cap is preferably of a sufficient diameter to promote seating and maintenance of position of the plug within the hole in the sclera, and to reduce the possibility of the shaft from passing completely through the sclera during or after insertion of the plug into the sclera. The outer diameter of the cap may be from 1-10 times the diameter of the shaft; preferably, the outer diameter of the cap is between 1-3 times the diameter of the shaft.

The shaft, as the remainder of the plug, may be configured to accomplish occlusion of an injection- or ocular surgery-related scleral hole. The shaft may be thin enough, for example, to occlude the hole made by a 33 gauge, or thinner, needle after intravitreous injection, or may be as thick as 1-2 mm in diameter, or more, to occlude holes created during, for example, macular hole surgery. The shaft may be of any size appropriate to occlude a particular discontinuity in the sclera. The shaft is preferably at least as long as a sclera is thick, but may be shorter than the thickness of a sclera, or may be longer. A typical sciera is 0.35-0.55 mm thick, but may be thicker or thinner. The thickness depends upon the particular individual, as well as the position of the discontinuity in the sclera; for example, the sclera tends to thin away from the iris and towards the retina. Where the shaft is longer than the thickness of a sclera, the shaft, when the plug comprising it is fully inserted, projects through the sclera an into the vitreous humor.

The surface of the shaft may be smooth or textured. For example, the surface of the shaft may be rough, ribbed or knurled so as to enhance contact between the plug and sclera, thereby reducing the potential for the plug to work its way out of the scleral hole. Particularly where the plug comprises a cap, the shaft may be ribbed or knurled directionally; that is, ribbed or knurled to promote insertion of the plug into the scleral hole and to discourage passage of the plug in the opposite direction, i.e., back out of the scleral hole.

In a preferred embodiment, the shaft is substantially cylindrical. In another embodiment, the shaft is substantially cylindrical along its entire length. In other embodiments, the shaft is ovoid, square, rectangular, square or rectangular with rounded edges, polygonal, or irregular in cross-section. In another embodiment, the shaft comprises a narrow portion and a wide portion. Typically, the shaft is attached to the cap through the narrow portion; the wide portion, distal to the cap, facilitates anchoring of the plug into the sclera. In one embodiment, the cross-sectional area of the wide portion is greater than that of the narrow portion. The wide portion of the shaft may be manufactured in a variety of configurations. For example, the shaft may flare. Such a flare may be substantially continuous along the length of the shaft, or may begin at any point along the length of the shaft. In another embodiment, the wide portion is a flange or protrusion from a portion of the main body of the shaft, e.g., from one side of the shaft. Such a flange or protrusion may have any shape that facilitates maintenance of the plug within the scleral hole while not substantially increasing the difficulty of insertion or the potential for scleral damage during insertion. In another embodiment, the wide portion comprises a flange or other protrusion that substantially encircles the shaft. For example, the wide portion may be an inverted cone or frustum, wherein the larger radius of the frustum is wider than the diameter of the shaft. In another embodiment, the wider portion of the shaft is a cylinder having a radius larger than the radius of the shaft. In another embodiment, the wider portion of the shaft has substantially the same cross-sectional shape as the shaft, but a cross-sectional area larger than the cross-sectional area of the shaft. There is no need, however, for the wide portion of the shaft to have a particular shape relative to the cross-sectional shape of the shaft, and the wide portion need not have the same cross-sectional shape as the shaft. In another embodiment, the shaft comprises a thread spirally disposed along a portion or all of the length of the shaft, so that the shaft of the plug functions as a screw. In this embodiment, the thread may proceed clockwise or counterclockwise along the shaft.

In another embodiment, the plug may be constructed so that the portion of the shaft distal to the cap comprises one or more flaps that may be folded against the shaft during insertion of the plug into the sclera, and which open, or fold away, from the shaft once the flap has been pushed completely through the sclera. The one or more flaps would act as an anchor.

In one embodiment, the wider portion of the shaft extends into the sclera itself, and serves as an anchor. In another embodiment, part or all of the wide portion of the shaft extends into the vitreous humor.

The end of the shaft distal to the cap may be flat, rounded, or tapered, or may be irregular. The surface of the end may be substantially perpendicular to the longitudinal axis of the shaft, or may be tilted, giving the end of the shaft a barbed appearance.

In one embodiment, the ocular plug comprises an opening extending at least the portion of the cap distal to the shaft, and, optionally, into the shaft. The opening can be used, for example, to receive a wire of fixed gauge. The wire is used to pick up the ocular plug and guide the ocular plug into a scleral discontinuity.

In another embodiment, the ocular plug does not comprise a cap. For example, the ocular plug may comprise a shaft only. In this embodiment, the shaft may be formed in any of the configurations as for the shafts of a plug with a cap as discussed above. For example, in its simplest form, the plug may simply be a cylinder, with a smooth, ribbed, knurled or textured surface, or may comprise one or more wide portions that can act as anchors. In one embodiment, the shaft (that is, the plug) comprises two wide portions. In a specific embodiment, the shaft is dumbbell-shaped. The dumbbell shape may be accomplished, for example, by thickening the ends of the shaft so that the change in thickness from center of the shaft to either end is continuous; alternatively, the change in thickness from center of the shaft to either end is discontinuous. Preferably, in this embodiment, the length of the shaft between the wide portions (e.g., the ends of the dumbbell) is at least the thickness of the sclera.

Ocular plugs may be pre-made to standard sizes, or may be custom-made to fill particular scleral holes or discontinuities, whether anticipated (as in the case of surgery) or unanticipated. In one embodiment, therefore, the invention provides an ocular plug, wherein said ocular plug has a shaft of a reproducible, standard size. The ocular plug may also be custom-made for a particular discontinuity. In specific embodiments, the standard or custom-made diameter size of a shaft for said ocular plug is a diameter sufficient to substantially occlude a scleral hole caused by passage of a 33, 32, 31, 30, 29, 28, 27, 26, 25, 24, 23, 22, 21, 20, 19, 18, 17, 16, 15, 14, 13, 12 or larger gauge needle. In other specific embodiments, the standard or custom-made diameter of a shaft for said ocular plug is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 millimeters, or wider. In other specific embodiments, the standard length of the shaft of said plug is 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45 or 1.50 millimeters.

Ocular plugs may be made from umbilical cord biomaterial by any method used to create or produce molded devices. Preferably, the umbilical cord biomaterial used to make an ocular plug is a dried, decellularized biomaterial.

Ocular plugs may be made, for example, by stamping the plugs from a sheet of the biomaterial using a shaped stamp. Alternatively, the plugs may be cut from a sheet of the biomaterial, or may be formed by removal of unwanted material from a block of the biomaterial. In a preferred embodiment, an ocular plug is formed using a mold. Where the ocular plug is formed using a mold, the biomaterial is preferably first made into a liquid, slurry, paste, or similar material amenable to forming in a mold.

In an exemplary embodiment of a method of making the ocular plug, umbilical cord biomaterial is first reduced to a collection of particles; that is, the biomaterial is micronized. The biomaterial may be micronized to a particle size of anywhere from about 1 micron to about 1 millimeter. Generally, the larger the particle size, the more porous the plug. Any method may be used to micronize the biomaterial, for example, ultrasound, physical shearing, homogenization, etc. Such micronization may be done dry (that is, by micronizing the biomaterial without any additional liquid), or may be done using a micronization liquid or carrier. If micronization with a liquid is performed, the liquid may be any physiologically acceptable liquid or solution that does not significantly degrade the biodegradable material, e.g., the tertiary structure of the proteins comprising the biomaterial. Typically, the ratio of biomaterial to liquid is 25 mg/ml to 300 mg/ml, but more or less of the biomaterial may be used. Determination that a desired particle size has been achieved may be accomplished by any means known in the art, e.g., microscopic examination, comparison to bead size standards, etc.

Once the desired micronized biomaterial is obtained, whether in wet or dry form, the micronized biomaterial is injected or otherwise forced into the mold and allowed to set. In one embodiment, the wet micronized biomaterial is forced into the mold and is then frozen, e.g., at a temperature of from −5° C. to −160° C. (though higher or lower temperatures would also work) for a time sufficient to allow ice crystals to form and grow, e.g., 2 hours to several days. The frozen plug is then freeze dried to substantial dryness, that is, to a water content of about 20% by weight or less. Preferably, any plugs formed using the biomaterial are freeze-dried to substantial dryness. Freeze-drying is particularly preferred as the process allows for the development of pores in the biomaterial constituting the plug. Plugs may also be heat-dried, but heat applied to dry the plugs is preferably not heat that would cause the breakdown of any component of the biomaterial. For example, in various embodiments, an ocular plug formed from biomaterial may be dried at about 70° C., about 65° C., about 60° C., about 55° C., about 50° C. or about 45° C., or less than about 70° C., less than about 65° C., less than about 60° C., less than about 55° C., less than about 50° C. or less than about 45° C.

Once the plugs are freeze-dried, or dried by other method, the biomaterial is preferably cross-linked to provide mechanical stability and integrity. Crosslinking may be accomplished by any method known in the art; particularly preferred are radiation, chemical, or heat crosslinking. Radiation crosslinking is preferred. Radiation used may be any known in the art to be useful for such a purpose, for example, electron-beam or e-beam radiation, gamma radiation or ultraviolet radiation. E-beam radiation is preferred. See, e.g., Odland, U.S. Pat. No. 5,989,498 "E-beam Sterilization of Biological Materials," The intensity of radiation used may be that ordinarily used for the sterilization of medical instruments. The biomaterial may also be chemically crosslinked using any chemical crosslinking methodology known in the art, for example, thiol-thiol crosslinking, amide-amide crosslinking, amine-thiol crosslinking, amine-carboxylic acid and thiol-carboxylic acid crosslinking, etc., as appropriate for the material from which the plug is made. The plug may also be heat crosslinked, typically using a thermal dehydration process. Most preferably the heat used for such crosslinking does not significantly degrade or structurally weaken the material in any way. Plugs may be heat crosslinked, for example, by placing the plugs in a vacuum oven at 105° C. for 1-5 hours, or until the desired structural integrity or degree of crosslinking is achieved.

5.2.5 Other Uses

The umbilical cord biomaterial can be used in any other medical application in which like materials are used, e.g., as a patch for wound repair.

In one embodiment, the umbilical cord biomaterial is used as a wrapping or covering for a replacement eye orb, e.g., a hydroxyapatite sphere.

In another embodiment, the umbilical cord biomaterial can be used to repair or ameliorate a cardiac defect. Such defects include, but are not limited to, cardiac wall defects, areas of necrosis due, e.g., to ischemia; repair of a cardiac valve; repair of patent foramen ovale, and the like. In another embodiment, the umbilical cord biomaterial is seeded or inoculated with cardiomyocytes. Immediately, or following culture to allow proliferation of the cardiomyocytes, the umbilical cord biomaterial is implanted into a cardiac defect as a living patch. In preferred embodiments, the umbilical cord biomaterial is placed so as to cover the defect completely.

5.3 Kits

The present invention further provides kits comprising one or more pieces of umbilical cord membrane biomaterial. Preferably, each of the one or more pieces the biomaterial is individually sterilely wrapped, e.g., in a peel-pouch.

In a more specific embodiment, the kit comprises a piece of umbilical cord biomaterial that is at least about 2×8 cm. In another embodiment, said kit comprises a piece of umbilical cord biomaterial approximately the size of an eardrum. The kit may comprise one or more pieces of umbilical cord biomaterial and any other medical device, disposable or drug that would facilitate treatment of a disease, disorder or condition treatable using the biomaterial. Preferably, each piece of the umbilical cord biomaterial in the kit is provided as a single sheet or patch in a sterile container or wrapping separate from the remainder of kit contents. In another embodiment, the kit comprises two or more pieces of umbilical cord biomaterial, separately wrapped or contained. In another embodiment, said kit comprises a support for the umbilical cord biomaterial. In specific embodiments, the support may be a natural or a synthetic material. In other specific embodiments, said support is a plastic film, plastic sheet, or a stretchable plastic wrap. In another embodiment, said kit comprises one or more disposables, e.g., paper tissues or towels, mats, cotton swabs, plastic or rubber gloves, disposable forceps, or the like. In a specific embodiment, said disposables are bandages, means for sterilizing skin, swabs, gloves, or sterile sheets. In another embodiment, said kit comprises an anti-infective agent, for example, an antibiotic ointment, cream, or spray. In another embodiment, said kit comprises a piece of umbilical cord biomaterial and one or more wound healing agents. In a specific embodiment, said wound healing agent is PDGF, TGF, hyaluronic acid, fibrin, or fibronectin. In another embodiment, said kit comprises umbilical cord biomaterial and a means for applying compression to a part of the body. In a specific embodiment, of any of the kits above, the kit comprises an instruction sheet suitable for use by a non-medical end user; an instruction sheet suitable for use by an end user in a medical profession; or a materials safety data sheet; or a combination thereof.

6. EXAMPLES

6.1 Example 1

Production of Umbilical Cord Biomaterial

The following example demonstrates one method of preparing umbilical cord biomaterial.
Materials and Equipment
The following items were obtained and, where appropriate, sterilized: human placenta (less than 48 hours old at the start of processing); surgical clamps/hemostats; scissors; scalpels; tweezers; Halsted mosquito; Adson bayonet forceps; grooved directors; cell scraper; autoclaved gauze; stainless steel rinsing trays; stainless steel cups; stainless steel processing trays. 0.9% NaCl solution; sterile water; specimen containers; personal protective equipment (including sterile and non-sterile gloves); certified clean room; decellularizing solution (0.5% deoxycholic acid solution); rocking platform (VWR Model 100); timer (VWR TRACEABLE® model); disinfected silicone grid; PVC wrap film; vacuum pump (Schuco-Vac 5711-130); heat dryer (BioRad Model 583); sterile cutting board; pouches for packaging (COT-360, 361, 362); stainless steel ruler; TRACEABLE® Digital Thermometer (Model 61161-364, Control Company); Accu-Seal Automatic Sealer (Accu-Seal, Model 630-1 B6 or 730-16B) with air compressor; and waterproof resealable bags (CCT-03S).
Procedure
A sterile field was set. The placenta was removed from the transport container and placed into a sterile stainless steel tray. Using surgical damps and scissors, the umbilical cord was cut off approximately 2 inches from the placental disc. The umbilical cord was rinsed with sterile 0.9% NaCl solution as many times as necessary to remove as much blood as possible; optionally, fingers were used to squeeze remaining blood from vessels. The umbilical cord was optionally placed in a separate sterile container cup prefilled with sterile 0.9% NaCl solution, if the cord did not have to be processed immediately. The harvested umbilical cord was placed in a refrigerator at 4° C. until use. The placental disk was placed back into the transport container to be utilized for other projects, or discarded.

The umbilical cord was processed as follows. The umbilical cord was removed from the specimen container, and squeezed to remove any remaining blood from vessels prior to introducing the umbilical cord to a processing tray. The umbilical cord was placed into a sterile stainless steel processing tray, and cut into segments 12 to 15 cm in length. The umbilical cord vein was then located for each segment, and canalized using an Adson bayonet forceps or grooved director. The vein and umbilical cord were then cut longitudinally, using scissors, until both the vein and umbilical cord were fully open. The umbilical cord, was placed on the processing tray with the opened vein side facing upward. The umbilical cord and vein were then bluntly dissected longitudinally between the vein wall and the umbilical cord wall with sterile tweezers or mosquito clamps. When both sides were separated, the vein was carefully removed. After vein removal, the two arteries were located and removed in the same manner. Depending on the purpose of the study, the resulting umbilical cord membrane (biomaterial) was placed in either in saline solution or in 1% deoxycholic acid solution (a decellularizing solution) and stored at 4° C. until serological testing results become available.
Storage and Quarantine of Umbilical Cord Membrane
The umbilical cord membrane, obtained as outlined above, was kept in sterile 0.9% saline solution or 1% deoxycholic acid solution for 10-20 days at 4° C. until serological test results, if ordered, were available. Saline solution, where used, was changed every 3 days. 1% deoxycholic acid solution, when used, was changed every 5 days.
Umbilical Cord Membrane Cleaning and Rinsing
A sterile field was set with a new set of sterilized trays as above. The Umbilical cord membrane was removed from the refrigerator and placed into a stainless steel processing tray. Sterile 0.9% saline solution is added to cover the bottom of the tray. All, or substantially all, residual deoxycholic solution, where used, was removed, and remaining cells and debris were removed from both sides of the tissue using a cell scraper and sterile tweezers. Sterile 0.9% saline solution was used as needed to aid in removal of the cells and debris. The umbilical cord membrane was rinsed three times in a separate stainless steel rinsing tray filled with sterile 0.9% saline solution. The saline solution was changed between each cleaning step. The umbilical cord membrane was then placed into a new sterile specimen container containing about 150 mL saline solution, and placed on a rocking platform for agitation for 5 minutes at setting #6. The scraping and rinsing steps were repeated once as necessary. The umbilical cord membrane was then placed into a sterile specimen container containing 150 mL sterile water, and placed on a rocking platform for agitation for 20 minutes at setting #6. This rinsing step was repeated three times.
Drying The Umbilical Cord Membrane
A TYVEK® sheet was placed onto a stainless steel processing tray. The cleaned umbilical cord membrane segments were removed from the specimen container one piece at a time, and excess fluid was gently squeezed out. The membrane segments were then placed on the surface of the TYVEK® sheet, epithelium side up, and gently stretched until flat. The membrane was then dried at about 50° C.±1.0° C. in a vacuum dryer. Sterile gauze was placed on the drying platform of the vacuum dryer, covering an area slightly larger than the area of the TYVEK® sheet. The total thickness of the gauze layer did not exceed the thickness of one folded 4×4 gauze. A sheet of silicone framing mesh was placed on top the gauze, smooth side up. The TYVEK® sheet with the tissue was then placed on the heat dryer platform on top of the silicone mesh. Another TYVEK® sheet was then placed on top of the tissue. A piece of PVC wrap film was then cut large enough to cover the entire drying platform, and pulled so that the film pulled tightly against the TYVEK® sheet (that is, was "sucked in" by vacuum) and so that there were no air leaks and no wrinkles over the tissue area). The vacuum pump was then set to approximately −22 inches Hg, and heat/vacuum drying was allowed to proceed for a total of about 120 minutes. Approximately 30-45 minutes into the drying process, the sterile gauze layer was replaced.

A new sterile field was set with a sterilized drying kit and cutting board. With the pump still running, the plastic film was removed from the TYVEK®, and the sheet and tissue were placed on a cutting board with the epithelium side of the tissue facing upward. The dried membrane (now umbilical cord biomaterial) was then gently removed from the TYVEK® sheet. The biomaterial segments were then cut with a scalpel into segments of a specified size, typically 2×2 cm or 1×1 cm. The dried, sized umbilical cord biomaterial was then placed and sealed into a peel-pouch package.

6.2 Example 2

Production of Umbilical Cord Biomaterial Laminate

Objective: To increase the size of a sheet of umbilical cord biomaterial for hernia repair.

Materials and Methods: All cited dimensions are approximate. Umbilical cord membrane from a 23.5 hour-old placenta was collected and processed as in Example 1 up to the point of drying. The final size of the membrane was approximately 35 cm by 4 cm. The membrane was cut into three pieces approximately 10 cm long. The pieces were arranged so as to overlap by about 2 cm on the long edge, and were dried at 50° C. between two sheets of TYVEK®.

Results: The biomaterial comprising laminated membrane thus obtained was approximately 10 cm by 10 cm. The sections did not separate upon rehydration in saline for 72 hours.

Umbilical cord membrane can also be laminated by placing two or more pieces of the biomaterial, interior (of the umbilical cord) side down, on a substrate in a mounting frame. The laminated membrane is then placed in a gel dryer and dried to substantial dryness (≦about 20% water content by weight) to produce a laminated umbilical cord biomaterial.

Another method of constructing a thicker biomaterial is to laminate intact umbilical cord (including Wharton's jelly but lacking arteries and vein). The intact cord is then processed, e.g., by rinsing, soaking in a solution such as a buffered saline solution, e.g., phosphate buffered saline, or a mild ionic or nonionic detergent solution. The cord is dried in a vacuum dryer to create an intact, double-layer biomaterial. Two or more layers of this double-layer material can be laminated by layering the biomaterials and drying further in a heated vacuum dryer. The drying/dehydration process can be heat drying or any other processes as described below.

6.3 Characterization of Dried Umbilical Cord Biomaterial

A study was undertaken to examine biomaterial made of heat dried human umbilical cord membrane (HUC) after sterilization by different doses of gamma irradiation. Samples of HUC were sterilized with 0, 20, 25, 30, or 40 kGy and then examined for water uptake (mass and thickness change), denaturation temperature, and tensile mechanical properties. HUC samples had been incubated for either 10 or 20 days in 1% D-cell (deoxycholic acid) solution during preparation.

6.3.1 Water Uptake

Individual samples of HUC for each condition (n=3) were weighed on a microbalance. Samples were then incubated in 10 mL of phosphate buffered saline at 37° C. for 1 hour. Samples were removed from the PBS and blotted dry a minimum of three times with a KIMWIPE® tissue. The samples were again weighed on a microbalance. The percentage water uptake ([wet weight (Ww)−dry weight (Wd)]/Wd*100) and equilibrium water content ([Ww−Wd]/Ww*100) were calculated.

Figure 1A:
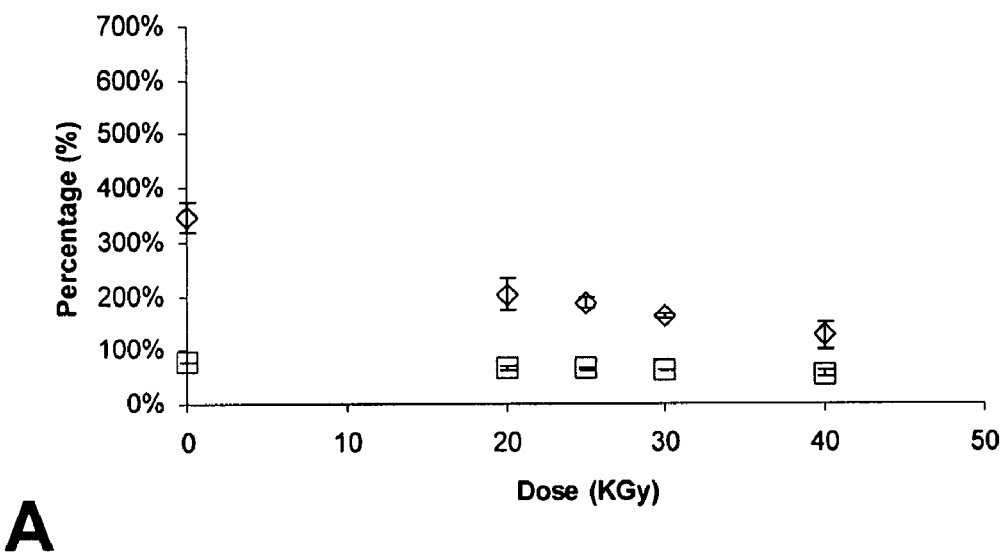
FIGS. 1A and 1B depict the effect of radiation dose on water uptake [$\Diamond$, (Ww−Wd)/Wd*100] and equilibrium water content [$\Box$, (Ww−Wd)/Ww*100] for human umbilical cord biomaterial incubated for 10 (A) and 20 (B) days in 1% D-cell solution.
Figure 1B:
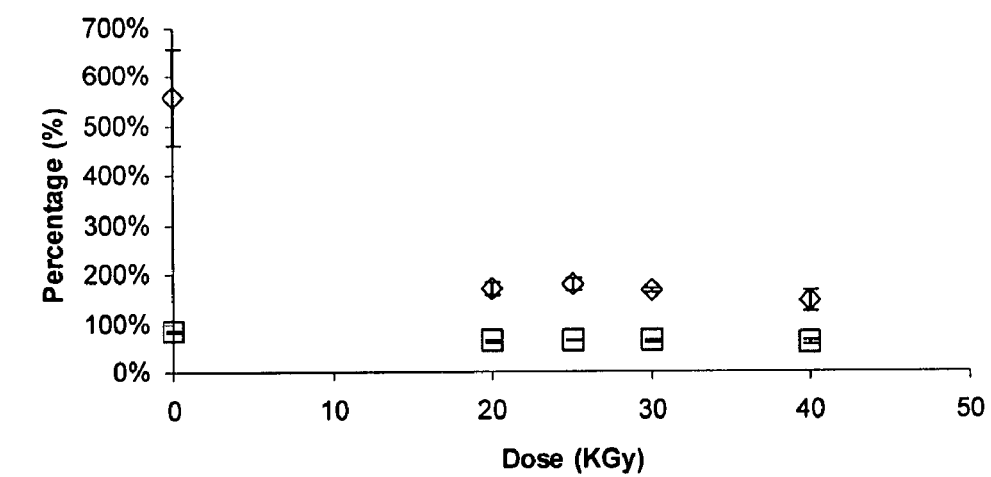

FIG. 1 summarizes the results of the rehydration for HUC incubated for 10 and 20 days. The initial water uptake of the control (nonsterilized samples) was much higher for HUC incubated for 20 days than for HUC incubated for 10 days, possibly due to the loosening of the membrane proteins by the detergent effect of the deoxycholic acid in the D-cell solution. Water uptake and equilibrium water content closely matched for the 10 and 20 days samples that were sterilized at all radiation doses. There was a linear decrease in the water uptake and the equilibrium water content of both sets of samples with increasing radiation dose. Even at the highest radiation dose, the membranes took up at least their own weight in water.

6.3.2 Changes in Thickness

Individual dog bone shaped (see, e.g., FIG. 4) samples of HUC for each condition (n=8) were mounted in squares of vellum paper so that the membrane could be easily handled during and after hydration. The thickness was measured in three locations for each sample and averaged. Samples were then incubated in 10 mL of phosphate buffered saline at 37° C. for 1 hour. Thickness measurements were repeated after hydration.

Overall, the average dry thickness of the HUC was ~70 μm, with the 10 and 20 day samples having average thickness of 57 and 86 μm respectively (Table 1 and Table 2). There appeared to be no correlation between radiation dose and dry thickness of the HUC. After rehydration, there was a marked difference in thickness between the sterilized and non-sterilized samples. There was little difference in the rehydrated thickness between the 10 and 20 day samples. Without wishing to be bound by any theory or mechanism, the difference observed can be due to cross-linking of collagen molecules caused by irradiation. There appeared to be a decrease in the magnitude of the thickness change upon rehydration with increasing dose; this effect was more pronounced with the 10 day samples.

TABLE 1

Changes in thickness of 10 day incubated HUC during hydration

| Dose (KGy) | dry (um) | SD | wet (um) | SD | increase (%) | SD |
|---|---|---|---|---|---|---|
| 0 | 61 | 23 | 243 | 82 | 316% | 109% |
| 20 | 44 | 10 | 107 | 20 | 147% | 19% |
| 25 | 58 | 24 | 132 | 40 | 134% | 28% |
| 30 | 67 | 22 | 125 | 45 | 87% | 32% |
| 40 | 57 | 23 | 106 | 46 | 91% | 36% |

TABLE 2

Changes in thickness of 20 day incubated HUC during hydration

| Dose (KGy) | dry (um) | SD | wet (um) | SD | increase (%) | SD |
|---|---|---|---|---|---|---|
| 0 | 88 | 22 | 279 | 51 | 240% | 123% |
| 20 | 76 | 22 | 149 | 26 | 106% | 48% |
| 25 | 85 | 50 | 130 | 21 | 83% | 61% |
| 30 | 61 | 23 | 138 | 51 | 125% | 31% |
| 40 | 121 | 32 | 209 | 46 | 77% | 36% |

Figure 2A:
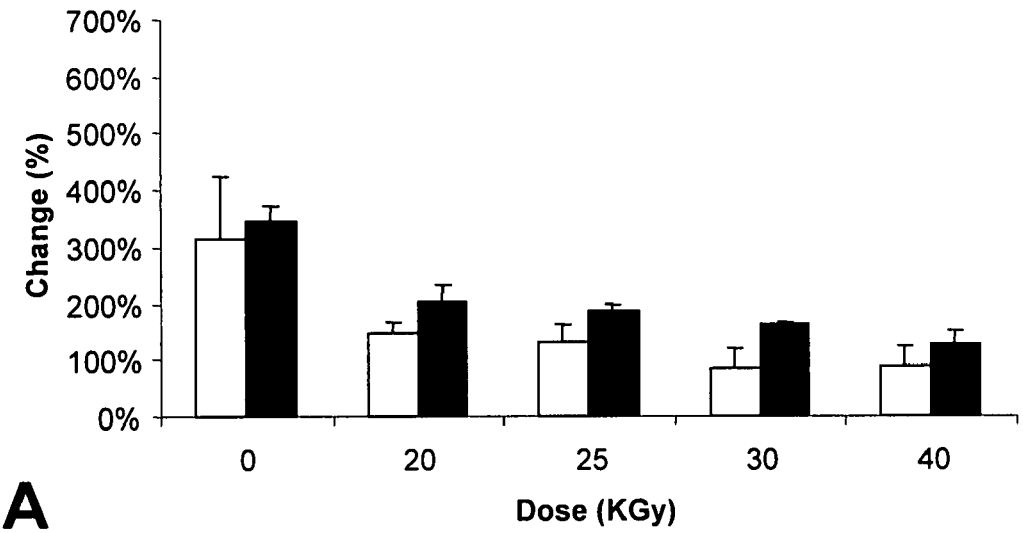
FIGS. 2A and 2B depict a comparison of the change in thickness ($\Box$) and water uptake ($\blacksquare$) during rehydration of gamma sterilized human umbilical cord biomaterial incubated for 10 (A) and 20 (B) days in 1% D-cell solution. Error bars indicate standard deviation.
Figure 2B:
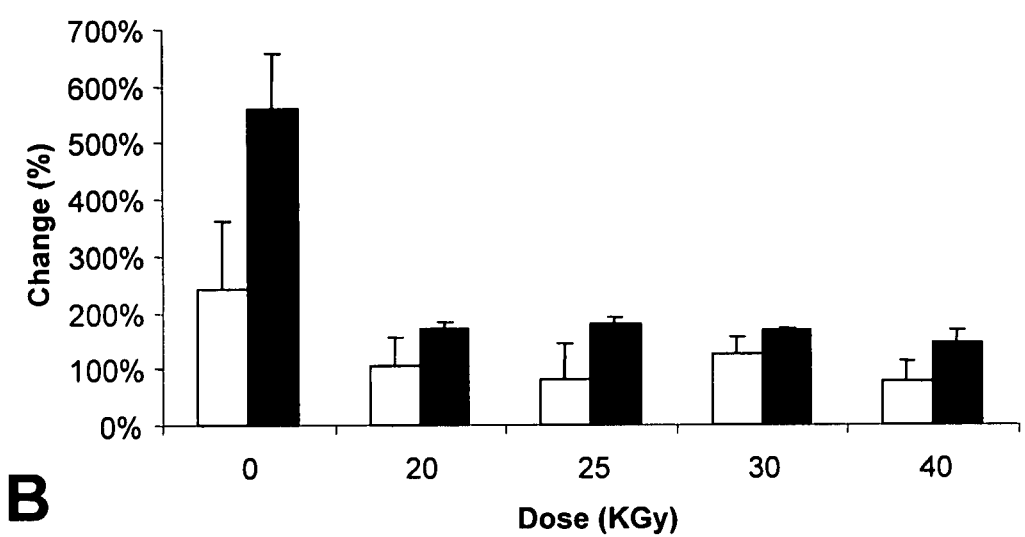

When the change in thickness of the membranes was compared to the water uptake (FIG. 2), there was a loose correlation between the amount of water taken up and the increase in thickness. The magnitude of the water uptake and the change in thickness both decreased with increasing gamma radiation dose. There was a stronger correlation between water uptake and thickness change for samples incubated for 10 days than those incubated for 20 days. This is due partially to the fact that the samples incubated for 20 days showed less difference between samples, but greater variability within a set of samples.

6.3.3 Denaturation Temperature

Individual samples of HUC for each condition (n=3) were incubated in 10 mL of phosphate buffered saline at 37° C. for 1 hour. Samples were removed from the PBS and blotted dry a minimum of three times with a KIMWIPE® tissue. The samples were sealed in aluminum hermetic differential scanning calorimeter (DSC) pans and tested in a TA Instruments modulated DSC (Q1000) in standard mode from 5-110° C. at 10° C./min. TA Instruments' "Universal Analysis" software was used to calculate the onset and peak values of the denaturation point of the membranes.

Figure 3:
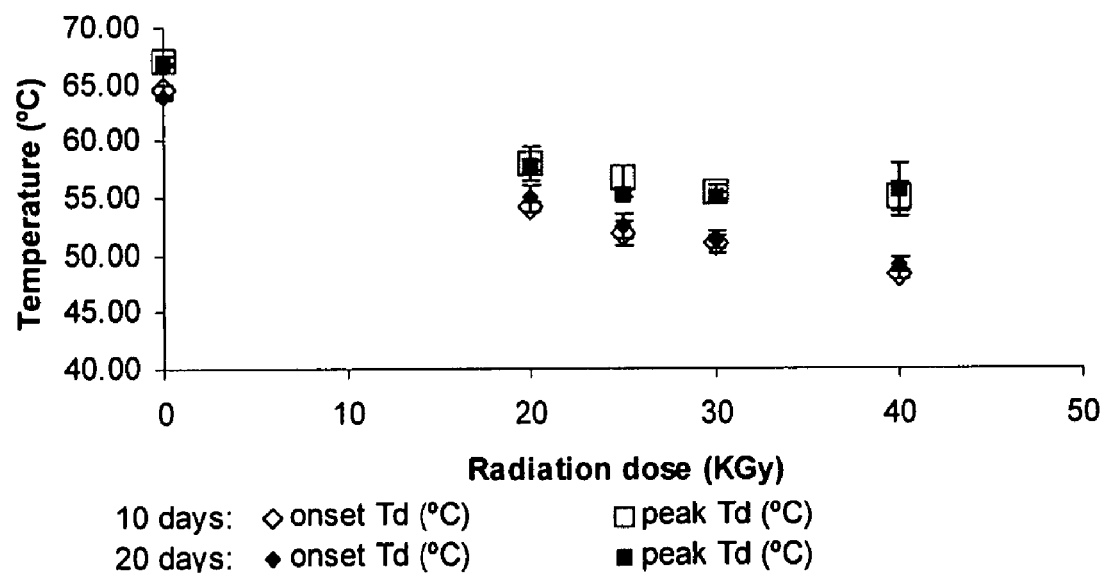
FIG. 3 depicts a comparison of the denaturation temperature of rehydrated human umbilical cord membrane that had previously been incubated in 1% D-cell solution for 10 or 20 days. There is essentially no difference between the different incubation times and there is a linear decrease in denaturation temperature with increasing radiation dose.

FIG. 3 graphically summarizes the denaturation temperature results for the HUC samples. The results are identical for samples incubated for 10 and 20 days. Onset and peak temperatures were only a few degrees different for each of the samples, and both onset and peak temperatures decreased linearly with increasing radiation dose. There was very low variability in the results.

Time of incubation in D-cell solution did not affect the denaturation temperature. There was a linear decrease in the onset and peak denaturation temperatures with increasing radiation dose for both the 10 and 20 day samples. From the denaturation data, there appeared to be no difference between soaking HUC for 10 or 20 days in 1% D-cell solution.

6.3.4 Tensile Properties

Individual dog bone shaped samples of human umbilical cord membrane for each condition (n=8) were mounted in squares of vellum paper so that the membrane could be easily handled during and after hydration. Samples were then incubated in 10 mL of phosphate buffered saline at 37° C. for 1 hour. The tensile properties of the membranes were evaluated based on American Society for Testing and Materials protocol D1708 (ASTM D1708); see FIG. 4 for more details of testing. Samples that had been cut along the long axis of the cord (longitudinal sections) and samples that had been cut perpendicular to the long axis (cross section) were tested where samples were available for each condition.

No differences were found between 10 and 20 day samples. Tests on the unsterilized human umbilical cord membrane determined the tissue to be anisotropic, with the tensile properties being different depending on the direction in which the samples were oriented (Table 3). Longitudinal samples had a higher stress at break and a higher modulus than cross section samples, and cross sectional samples had a greater range of values for the extension at break (how far the tissue stretched before breaking). In all cases, when the load was removed from the unsterilized samples, the tissue appeared by visual inspection to return to its original shape with no obvious distortions. Force was applied at a rate of 33 mm/min.

TABLE 3

Tensile testing results for non-sterilized HUC (10 and 20 day samples)

| Orientation | Stress at break (MPa) | Modulus (MPa) | Extension at break (%) |
|---|---|---|---|
| Longitudinal | 2.3-8.8 | 14.2-27.5 | 135-270 |
| Cross | 0.1-3.5 | 0.5-8.9 | 60-480 |

While there were no differences between the tensile properties of the 10 and 20 day samples or the different radiation doses, there were striking differences in how unsterilized and sterilized samples failed. Nonsterilized samples failed by breakage of the sample, while the sterilized samples failed mostly by delamination of layers of tissue. Additionally, the sterilized tissue was noticeably deformed after the load had been removed.

The tensile properties of HUC most closely resembled skin (Table 4). This was true of both the sterilized and non-sterilized tissue.

TABLE 4

Comparison of tensile properties of HUC (10 and 20 day samples) and other tissues

| | Tensile strength (MPa) | Tensile modulus (MPa) | Extension at break (%) |
|---|---|---|---|
| Tendon/ligament | 100-2,000 | 50-150 | 5-50 |
| Articular cartilage | | 1-10 | |
| Skin | 10-40 | 2-20 | 50-200 |
| Compact bone | 10,000-20,000 | | 2-3 |
| HUC (long) non-sterile | 2.3-8.8 | 14.2-27.5 | 135-270 |
| HUC (long) (sterile) | 1.1-12.4 | 7.4-51.4 | 60-258 |

6.3.5 Suture Pull-Out Strength

The umbilical cord biomaterial was determined to have a superior suture pull-out strength compared to dried human amniotic membrane. In a test similar to that described in Section 6.3.4, above, one short side of a 1×2 section of umbilical cord biomaterial was glued to vellum paper, and the other short side sutured to a second piece of vellum paper, as depicted in FIG. 5A. The pieces of vellum paper were held by grips, and a load was applied to the suture at a rate of about 12.7 mm/min. The umbilical cord biomaterial demonstrated an average pull-out resistance of about 1.4 Newtons (N), with a range of about 0.75 N to about 2.4 N, while the dried amniotic membrane demonstrated a pull-out resistance averaging about 0.3 N. See FIG. 5B.

6.4 Example 4

Biocompatibility of Umbilical Cord Biomaterial

This study evaluated the host response to an implant made of umbilical cord biomaterial during absorption following subcutaneous implantation in a rat model.

6.4.1 Materials and Methods

Test materials for implantation consisted of umbilical cord biomaterial or high density polyethylene (HDPE; control).

Umbilical cord biomaterial was provided as dried umbilical cord membrane measuring approximately 1 cm×1 cm sections prepared in either 0.9% NaCl (Test article A; non-decellularized) or 1% deoxycholic acid (Test articles B and C; decellularized).

The 16 rats used in the experiments were ten week old male *Rattus norvegicus* strain H1A®:(SD)CVF® (Hilltop Lab Animals, Inc.). Animal weight at the time of implantation ranged from 344 grams to 392 grams. Maintenance of animals during the experiment conformed to Standard Operating Procedures based on the "Guide for the Care and Use of Laboratory Animals".

On the day of the implant, each rat was identified and weighed. Groups of four animals were arbitrarily assigned to be terminated 1 week, 3 weeks, 6 weeks or eight weeks after implantation (Table 5).

TABLE 5

Implantation of test articles:

| Animal Number | Bilateral Implantation Left | Right | Termination Interval |
|---|---|---|---|
| 1 | C | A | 1 week |
| 2 | C | A | |
| 3 | B | A | |
| 4 | B | A | |
| 5 | C | A | 3 weeks |
| 6 | C | A | |
| 7 | B | A | |
| 8 | B | A | |
| 9 | C | A | 6 weeks |
| 10 | C | A | |
| 11 | B | A | |
| 12 | B | A | |
| 13 | C | A | 8 weeks |
| 14 | C | A | |
| 15 | B | A | |
| 16 | B | A | |

For implantation, the animals were anesthetized by intraperitoneal injection of ketamine hydrochloride and xylazine (66 mg/kg and 9 mg/kg, respectively) dosed at 2.25 ml/kg. The implant region was scrubbed with a germicidal soap and wiped with 70% alcohol. Separate incisions were made on each side of the back through the skin and parallel to the lumbar region of the vertebral column. A pocket was formed by blunt dissection in the subcutaneous tissue on each side of the back. One section of the test material was implanted into each pocket such that it lay as flat in the pocket as reasonably possible. A nonsorbable suture was cut into approximately 1 cm length sections and placed at each test article implantation site as a location marker. One section of the negative control article (HDPE) was similarly implanted caudally to the sections of the test article. The skin was closed with wound clips.

Following implantation, the animals were observed daily for general health, and the incisions were examined for adverse reactions until wound clip removal. Detailed examinations for clinical signs of disease or abnormality were conducted weekly and at termination.

At 1, 3, 6 and 8 weeks after implantation, the designated animals were weighed and euthanized by carbon dioxide inhalation. Macroscopic observation of the viscera was conducted. The general appearance of the skin at the implantation sites was recorded. The implant sites were exposed by incision along the midline from the proximal to the distal end of the rat, and the skin was gently pulled away from the implantation site. The implanted materials were measured to the nearest millimeter (length and width) and the color and consistency of the surrounding tissue was documented. The sites were also photographed. The implant sites and any abnormal tissues were excised and preserved in 10% neutral buffered formalin (NBF) until further processing. After fixation, the implant sites and any abnormal tissues were histologically processed (embedded, sectioned and stained with hematosylin and eosin) for microscopic evaluation by a pathologist.

Implantation sites were evaluated to assess any change in the integrity of the form of the test material. The local tissue response was evaluated and compared to the reactions at the negative control article sited. The evaluation included characterization of the test material in regard to acute inflammation, chronic inflammation, granulation tissue formation, foreign body reaction, and foreign body giant cell formation. In addition, the formation and the thickness change of the fibrous capsule around the implants, the change in implants' characteristics at degradation (e.g., size and shape, formation of particles, fibers and amorphous gel, etc.) were also evaluated. Microscopic cellular changes were graded according to severity on a scale of 0 to 4.

6.4.2 Results

Clinical observations. All animals appeared clinically normal throughout the study, Minor scabs or ulcerations were noted at the anesthetic injection sites; these areas resolved without treatment.

Body weight data. In general, all rats gained weight over the course of the study, and weight gains were considered acceptable.

Macroscopic observations. Generally, all animals, and the appearance of the skin, appeared macroscopically normal following termination. In general, the color and consistency of the tissue surrounding the implant appeared normal for all animals from three week termination interval. At the one week termination interval, some signs of surgical trauma was still evident, which is typical. For each animal, symptoms arising from implantation of the test articles (umbilical cord biomaterial) were mild enough that the biomaterial was considered a nonirritant.

Implant absorption. Implant size at the various termination points is presented in Tables 6 and 7. In several cases, the implant was found to have been completely absorbed by the host. Average implant sizes for the test articles at each of the terminations points is shown in Table 8.

TABLE 6

Measurements of implanted materials at termination - left side

| Group | Animal # | Site | Length (mm) | Width (mm) | Presence/Absence of Test Material |
|---|---|---|---|---|---|
| 1 Week | 1 | Test | 9.8 | 7.8 | Present |
| | | Control | 11.8 | 10.0 | Present |
| | 2 | Test | 8.6 | 8.9 | Present |
| | | Control | 13.5 | 10.7 | Present |
| | 3 | Test | 10.5 | 10.9 | Present |
| | | Control | 13.8 | 10.7 | Present |
| | 4 | Test | 10.0 | 8.8 | Present |
| | | Control | 14.1 | 11.4 | Present |
| 3 Weeks | 5 | Test | 5.3 | 8.3 | Present |
| | | Control | 11.0 | 13.6 | Present |
| | 6 | Test | 4.2 | 6.2 | Present |
| | | Control | 12.2 | 15.6 | Present |
| | 7 | Test | 7.2 | 5.0 | Present |
| | | Control | 10.9 | 13.1 | Present |
| | 8 | Test | 8.2 | 7.6 | Present |
| | | Control | 11.4 | 14.0 | Present |
| 6 Weeks | 9 | Test | 6.9 | 6.9 | Present |
| | | Control | 8.9 | 10.9 | Present |

TABLE 6-continued

Measurements of implanted materials at termination - left side

| Group | Animal # | Site | Length (mm) | Width (mm) | Presence/Absence of Test Material |
|---|---|---|---|---|---|
| | 10 | Test | 5.9 | 4.6 | Present |
| | | Control | 10.5 | 13.5 | Present |
| | 11 | Test | 6.1 | 6.2 | Present |
| | | Control | 10.6 | 11.8 | Present |
| | 12 | Test | 6.2 | 6.9 | Present |
| | | Control | 11.4 | 10.5 | Present |
| 8 Weeks | 13 | Test | 8.4 | 6.0 | Present |
| | | Control | 12.1 | 12.1 | Present |
| | 14 | Test | NA | NA | Absent |
| | | Control | 14.8 | 12.0 | Present |
| | 15 | Test | NA | NA | Absent |
| | | Control | 12.7 | 14.0 | Present |
| | 16 | Test | 9.3 | 8.1 | Present |
| | | Control | 12.5 | 13.5 | Present |

TABLE 7

Measurements of implanted materials at termination - right side

| Group | Animal # | Site | Length (mm) | Width (mm) | Presence/Absence of Test Material |
|---|---|---|---|---|---|
| 1 Week | 1 | Test | 10.4 | 9.9 | Present |
| | | Control | 12.2 | 12.2 | Present |
| | 2 | Test | 7.5 | 10.1 | Present |
| | | Control | 12.1 | 11/2 | Present |
| | 3 | Test | 7.8 | 6.8 | Present |
| | | Control | 10.8 | 11.6 | Present |
| | 4 | Test | 8.3 | 6.6 | Present |
| | | Control | 11.7 | 12.2 | Present |
| 3 Weeks | 5 | Test | 5.5 | 8.0 | Present |
| | | Control | 12.3 | 13.2 | Present |
| | 6 | Test | 6.1 | 5.5 | Present |
| | | Control | 11.5 | 10.9 | Present |
| | 7 | Test | NA | NA | Absent |
| | | Control | 10.7 | 10.2 | Present |
| | 8 | Test | 7.6 | 5.5 | Present |
| | | Control | 10.3 | 11.7 | Present |
| 6 Weeks | 9 | Test | NA | NA | Absent |
| | | Control | 10.6 | 9.5 | Present |
| | 10 | Test | NA | NA | Absent |
| | | Control | 10.4 | 14.9 | Present |
| | 11 | Test | NA | NA | Absent |
| | | Control | 11.4 | 10.5 | Present |
| | 12 | Test | NA | NA | Absent |
| | | Control | 10.2 | 12.7 | Present |
| 8 Weeks | 13 | Test | 7.8 | 5.6 | Present |
| | | Control | 12.3 | 11.6 | Present |
| | 14 | Test | 11.2 | 5.9 | Present |
| | | Control | 14.4 | 12.6 | Present |
| | 15 | Test | NA | NA | Absent |
| | | Control | 13.5 | 12.2 | Present |
| | 16 | Test | NA | NA | Absent |
| | | Control | 11.7 | 13.8 | Present |

TABLE 8

Average length and width of test articles

| | Average Length and Width of the Test Articles | | | | | |
|---|---|---|---|---|---|---|
| | 4830 | | 4825 | | 4838 | |
| Interval | Length (mm) | Width (mm) | Length (mm) | Width (mm) | Length (mm) | Width (mm) |
| 1 weeks | 9.2 | 8.4 | 10.3 | 9.9 | 8.5 | 8.4 |
| 3 weeks | 4.8 | 7.3 | 7.7 | 6.3 | 4.8 | 4.8 |
| 6 weeks | 6.4 | 5.8 | 6.2 | 6.6 | Absorbed | Absorbed |
| 8 weeks | 4.2 | 3.0 | 4.7 | 4.1 | 4.8 | 5.8 |

Further results indicated that both decellularized and non-decellularized umbilical cord biomaterial have excellent biocompatibility. Animal responses to both biomaterials was similar to control USP grade HDPE. No fibrous tissue encapsulations developed during the course of the implantation study, whereas HDPE implants developed fibrosis at later stages of the study. While both decellularized and non-decellularized biomaterials were biodegradable, it was noted that implanted decellularized membranes lasted longer (e.g., 6 to 8 weeks) than non-decellularized biomaterials (about 3 to 6 weeks).

EQUIVALENTS

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. An umbilical cord-derived biomaterial comprising an isolated mammalian umbilical cord membrane, from which the vessels have been removed, and Wharton's jelly, wherein said biomaterial comprises less than 20% water by weight.

2. The biomaterial of claim 1 comprising an exogenous bioactive molecule.

3. The biomaterial of claim 2, wherein said bioactive molecule is a cytokine or a growth factor.

4. The biomaterial of claim 2, wherein said bioactive molecule is an extracellular matrix protein.

5. The biomaterial of claim 4, wherein said extracellular matrix protein is collagen, fibronectin, elastin, vitronectin, or hyaluronic acid.

6. The biomaterial of claim 2, wherein said bioactive molecule is hyaluronic acid.

7. The biomaterial of claim 6, wherein said hyaluronic acid is crosslinked to said umbilical cord membrane.

8. The biomaterial of claim 2, wherein the bioactive molecule is an antibiotic, a hormone, a growth factor, an anti-tumor agent, an anti-fungal agent, an anti-viral agent, a pain medication, an anti-histamine, an anti-inflammatory agent, an anti-infective agent, a wound healing agent, a wound sealant, a cellular attractant, a scaffolding reagent, or a small molecule.

9. The biomaterial of claim 8, further comprising a hydrogel composition.

10. The biomaterial of claim 1, comprising an exogenous polymer.

11. The biomaterial of claim 10, wherein said exogenous polymer is a synthetic biodegradable polymer or an anionic polymer.

12. An umbilical cord-derived biomaterial comprising an isolated mammalian umbilical cord membrane and Wharton's jelly, wherein said biomaterial comprises less than 20% by weight, and wherein the biomaterial is decellularized.

13. The biomaterial of claim 12, additionally comprising an exogenous stem cell.

14. An umbilical cord-derived biomaterial comprising an isolated mammalian umbilical cord membrane and Wharton's jelly, wherein said biomaterial comprises less than 20% water by weight, and wherein the biomaterial additionally comprising an exogenous stem cell.

15. The biomaterial of claim 14, wherein said exogenous stem cell is a placental stem cell, a mesenchymal stem cell, an embryonic stem cell, or a somatic stem cell.

16. The biomaterial of claim 15, wherein said somatic stem cell is a neural stem cell, a hepatic stem cell, a pancreatic stem cell, an endothelial stem cell, a cardiac stem cell, or a muscle stem cell.

17. A laminate comprising a plurality of layers, wherein at least one of the layers comprises an umbilical cord-derived biomaterial comprising an isolated mammalian umbilical cord membrane and Wharton's jelly, wherein said biomaterial comprises less than 20% water by weight.

18. A method of delivering a therapeutic agent to a subject comprising contacting the subject with the composition of claim 1, wherein said composition comprises a therapeutic agent.

* * * * *